(12) United States Patent
Kawaoka et al.

(10) Patent No.: US 8,043,856 B2
(45) Date of Patent: Oct. 25, 2011

(54) ADENOVIRAL VECTORS FOR INFLUENZA VIRUS PRODUCTION

(75) Inventors: Yoshihiro Kawaoka, Middleton, WI (US); Makoto Ozawa, Tokyo (JP)

(73) Assignee: Wisconsin Alumni Research Foundation, Madison, WI (US)

( * ) Notice: Subject to any disclaimer, the term of this patent is extended or adjusted under 35 U.S.C. 154(b) by 143 days.

(21) Appl. No.: 12/139,183

(22) Filed: Jun. 13, 2008

(65) Prior Publication Data

US 2009/0047728 A1     Feb. 19, 2009

Related U.S. Application Data

(60) Provisional application No. 60/944,025, filed on Jun. 14, 2007.

(51) Int. Cl.
*C12N 15/00* (2006.01)
*C12N 5/10* (2006.01)
*C12N 7/02* (2006.01)
*A61K 39/187* (2006.01)

(52) U.S. Cl. ............... 435/456; 424/209.1; 424/206.1; 435/325; 435/239

(58) Field of Classification Search ................... None
See application file for complete search history.

(56) References Cited

U.S. PATENT DOCUMENTS 7,601,356 B2 * 10/2009 Jin et al. .................. 424/209.1
2008/0187557 A1 * 8/2008 Sambhara et al. ......... 424/233.1

FOREIGN PATENT DOCUMENTS

| WO | WO-0104333 A1 | 1/2001 |
|----|---------------|--------|
| WO | WO-0125462 A1 | 4/2001 |
| WO | WO-03080846 A1 | 10/2003 |
| WO | WO-2008156681 A2 | 12/2008 |
| WO | WO-2008156681 A3 | 12/2008 |

OTHER PUBLICATIONS

Kovesdi et al. Adenoviral vectors for gene transfer, 1997, Current Opinion in Biotechnology, vol. 8, pp. 583-589.*
Alonso-Caplen et al., Efficient Transcription, Not Translation, Is Dependent on Adenovirus Tripartite Leader Sequences at Late Times of Infection, 1988, Journal of Virology, vol. 62, No. 5, pp. 1606-1616.*
Hatta et al., The NB Protein of Influenza B Virus Is Not Necessary for Virus Replication In Vitro, 2003, Journal of Virology, vol. 77, No. 10, pp. 6050-6054.*
Watanabe et al., Influenza A Virus Can Undergo Multiple Cycles of Replication without M2 Ion Channel Activity, 2001, Journal of Virology, vol. 75, No. 12, pp. 5656-5662.*
Tang et al., Recombinant adenovirus encoding the HA gene from swine H3N2 influenza virus partially protects mice from challenge with heterologous virus: A/HK/1/68 (H3N2), 2002, Archives of Virology, vol. 147, pp. 2125-2141.*
"International Application Serial No. PCT/US2008/007417, International Search Report mailed Jan. 30, 2009".
"International Application Serial No. PCT/US2008/007417, Written Opinion mailed Jan. 30, 2009".
Hoffmann, E., et al., "A DNA Transfection System for Generation of Influenza A Virus from Eight Plasmids", *Proceedings of the National Academy of Sciences of USA, National Academy of Science*, 97(11), May 23, 2000, 6108-6113.
Ozawa, M., et al., "An adenovirus vector-mediated reverse genetics system for Influenza A virus generation", *Journal of Virology, The American society for Microbiology*, US vol. 81 (17), XP002471230, ISSN: 0022-538X, (Jun. 27, 2007), 9556-9559.

* cited by examiner

*Primary Examiner* — Mary E Mosher
*Assistant Examiner* — Benjamin P Blumel
(74) *Attorney, Agent, or Firm* — Schwegman, Lundberg & Woessner, P.A.

(57) ABSTRACT

The invention provides adenovirus and retrovirus vectors useful to prepare influenza virus. Also provided is a canine RNA polymerase I promoter and vectors having that promoter.

29 Claims, 6 Drawing Sheets

Figure 1A:
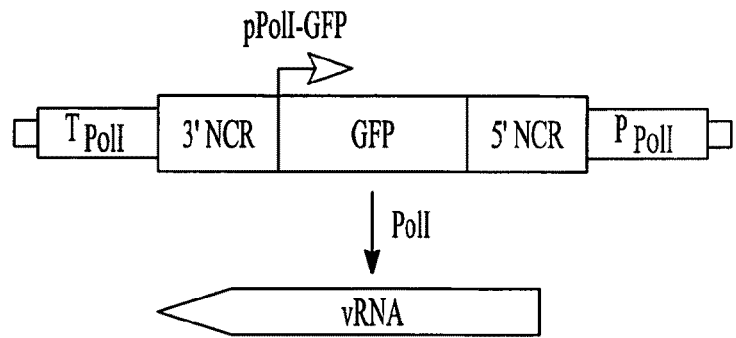

```
A A C T A C T A T A G G T A G G C A G        DROSOPHILA

C A G G A A G G T A G G G G A A G A C        XENOPUS

T T C G T C T G T A G G A G C G A G T        CHICKEN

G A G A T A T A T G C T G A C A C G C        RAT

G A G A T A G G T A C T G A C A C G C        MOUSE

G G G T T A T A T G C T G A C A C G C        HUMAN

C A G G T A G G T G C T G A C A C G T        DOG
```

```
                      ──────────────────▶
NW_878945 28608:GCTGCCTCTGCCGCGCGTGGCCCTCCACCTCCCCTGGCCCGAGCCGGGGT   28559
MDCK -457      1:GCTGCCTCTGCCGCGCGTGGCCCTCCACCTCCCCTGGCCCGAGCCGGGGT      50
                 **************************************************

NW_878945 28558:TGGGGACGGCGGTAGGCACGGGGCGGTCCTGAGGGCCGCGGGGGACGGCC   28509
MDCK -457     51:TGGGGACGGCGGTAGGCACGGGGCGGTCCTGAGGGCCGCGGGGGACGGCC     100
                 **************************************************

NW_878945 28508:TCCGCACGGTGCCTGCCTCCGGAGAACTTTGATGATTTTTCAAAGTCTCC   28459
MDCK -457    101:TCCGCACGGTGCCTGCCTCCGGAGAACTTTGATGATTTTTCAAAGTCTCC     150
                 **************************************************

NW_878945 28458:TCCCGGAGATCACTGGCGTGGCGGCGTGGCGGCGTGGCGGCGTGGCGGCG   28409
MDCK -457    151:TCCCGGAGATCACTGGCGTGGCGGCGTGGCGGCGTGGCGGCGTGGCGGCG     200
                 **************************************************
                     ─ ─ ─ ─ ─ ─ ─ ─ ─ ─ ─ ─ ─ ─▶
NW_878945 28408:-----------------TGGCGTCTCCACCGACCGCGTATCGCCCCTCCTC   28375
MDCK -457    201:TGGCGGCGTGGCGGCGTGGCGTCTCCACCGACCGCGTATCGCCCCTCCTC     250
                                  *********************************

NW_878945 28374:ACCCCCCCCCCCCCCCGGGTTACCTGGGGCGACCAGAAAGCCCTGGGGGC   28325
MDCK -457    251:ACCCCCCCCCCCCCCCGGTTTCCCTGGGTCGACCAGATAGCCCTGGGGGC     300
                 ****************** ** ****** ******* ************

NW_878945 28324:NGGGGGCTCCGTGGGGTGGGGGTGGGGGGGCGCCGTGGGGCAGGTTTTGG   28275
MDCK -457    301:-------TCCGTGGGGTGGGGGTGGGGGGGCGCCGTGGGGCAGGTTTTGG     343
                        *******************************************

NW_878945 28274:GTACAGTTGGCCGTGTCACGGTCCCGGGAGGTCGCGGTGACCTGTGGCTG   28225
MDCK -457    344:GTACAGTTGGCCGTGTCACGGTCCCGGGAGGTCGCGGTGACCTGTGGCTG     393
                 **************************************************
                                    ◀─ ─ ─ ─ ─ ─ ─ ─ ─ ─
NW_878945 28224:GTCCCCGCCGGCAGGCGCGGTTATTTTCTTGCCCGAAATGAACATTTTTT   28175
MDCK -457    394:GTCCCCGCCGGCAGGCGCGGTTATTTTCTTGCCCGAAATGAACATTTTTT     443
                 **************************************************
                ─ ─ ─ ─ ─ ─ ─
NW_878945 28174:GTTGCCAGGTAGGT   28161
MDCK -457    444:GTTGCCAGGTAGGT     457
                 **************
```

*FIG. 6C*

SEQUENCE LISTING

```
<160> NUMBER OF SEQ ID NOS: 16

<210> SEQ ID NO 1
<211> LENGTH: 19
<212> TYPE: DNA
<213> ORGANISM: Drosophila

<400> SEQUENCE: 1
aactactata ggtaggcag                                                   19

<210> SEQ ID NO 2
<211> LENGTH: 19
<212> TYPE: DNA
<213> ORGANISM: Xenopus

<400> SEQUENCE: 2
caggaaggta ggggaagac                                                   19

<210> SEQ ID NO 3
<211> LENGTH: 19
<212> TYPE: DNA
<213> ORGANISM: Chicken

<400> SEQUENCE: 3
ttcgtctgta ggagcgagt                                                   19

<210> SEQ ID NO 4
<211> LENGTH: 19
<212> TYPE: DNA
<213> ORGANISM: Rat

<400> SEQUENCE: 4
gagatatatg ctgacacgc                                                   19

<210> SEQ ID NO 5
<211> LENGTH: 19
<212> TYPE: DNA
<213> ORGANISM: Mouse
```

<400> SEQUENCE: 5
gagataggta ctgacacgc                                                    19

<210> SEQ ID NO 6
<211> LENGTH: 19
<212> TYPE: DNA
<213> ORGANISM: Human

<400> SEQUENCE: 6
gggttatatg ctgacacgc                                                    19

<210> SEQ ID NO 7
<211> LENGTH: 19
<212> TYPE: DNA
<213> ORGANISM: Dog

<400> SEQUENCE: 7
caggtaggtg ctgacacgt                                                    19

<210> SEQ ID NO 8
<211> LENGTH: 448
<212> TYPE: DNA
<213> ORGANISM: Canine
<220> FEATURE:
<221> NAME/KEY: misc_feature
<222> LOCATION: 285
<223> OTHER INFORMATION: n = A,T,C or G

<400> SEQUENCE: 8
gctgcctctg ccgcgcgtgg ccctccacct ccctggccc gagccggggt tggggacggc         60
ggtaggcacg gggcggtcct gagggccgcg ggggacggcc tccgcacggt gcctgcctcc       120
ggagaacttt gatgattttt caaagtctcc tcccggagat cactggcgtg cggcgtggc       180 ggcgtggcgg cgtggcggcg tggcgtctcc accgaccgcg tatcgcccct cctcaccccc       240 ccccccccc gggttacctg gggcgaccag aaagccctgg gggcngggg ctccctgggg         300 tgggggtggg gggcgccgt ggggcaggtt ttgggtacag ttggccgtgt cacggtcccg        360
ggaggtcgcg gtgacctgtg gctggtcccc gccggcaggc gcggttattt tcttgcccga      420
aatgaacatt ttttgttgcc aggtaggt                                         448

<210> SEQ ID NO 9
<211> LENGTH: 8
<212> TYPE: PRT
<213> ORGANISM: Artificial Sequence
<220> FEATURE:
<223> OTHER INFORMATION: A synthetic polypeptide

<400> SEQUENCE: 9

Arg Glu Arg Arg Arg Lys Lys Arg
1               5

<210> SEQ ID NO 10
<211> LENGTH: 4
<212> TYPE: PRT
<213> ORGANISM: Artificial Sequence
<220> FEATURE:
<223> OTHER INFORMATION: A synthetic polypeptide

<400> SEQUENCE: 10

Arg Glu Thr Arg
1

```
<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15
<211> LENGTH: 302
<212> TYPE: DNA
<213> ORGANISM: Canine

<400> SEQUENCE: 15
cgtggcgtct ccaccgaccg cgtatcgccc ctcctcaccc cccccccccc cggtttccct      60
gggtcgacca gatagccctg ggggctccgt ggggtggagg tggggggggcg ccgtggggca    120 ggttttgggt acagttggcc gtgtcacggt cccgggaggt cgcggtgacc tgtggctggt    180
ccccgccggc aggcgcggtt attttcttgc ccgaaatgaa cattttttgt tgccaggtag    240
gtccgccggc aggcgcggtt attttcttgc ccgaaatgaa cattttttgt tgccaggtag    300
gt                                                                  302

<210> SEQ ID NO 16
<211> LENGTH: 457
<212> TYPE: DNA
<213> ORGANISM: Canine

<400> SEQUENCE: 16
gctgcctctg ccgcgcgtgg ccctccacct ccctggccc gagccggggt tggggacggc       60
ggtaggcacg gggcggtcct gagggccgcg ggggacggcc tccgcacggt gcctgcctcc    120
ggagaacttt gatgattttt caaagtctcc tcccggagat cactggcgtg gcggcgtggc    180
ggcgtggcgg cgtggcggcg tggcggcgtg gcggcgtggc gtctccaccg accgcgtatc    240
gcccctcctc accccccccc cccccggtt tccctgggtc gaccagatag ccctgggggc    300
tccgtggggt gggggtgggg gggcgccgtg gggcaggttt tgggtacagt tggccgtgtc    360
acggtcccgg gaggtcgcgg tgacctgtgg ctggtccccg ccggcaggcg cggttatttt    420
cttgcccgaa atgaacattt tttgttgcca ggtaggt                             457
```

ADENOVIRAL VECTORS FOR INFLUENZA VIRUS PRODUCTION

CROSS-REFERENCE TO RELATED APPLICATIONS

This application claims the benefit of the filing date of U.S. application Ser. No. 60/944,025, filed on Jun. 14, 2007, the disclosure of which is incorporated by reference herein.

STATEMENT REGARDING FEDERALLY SPONSORED RESEARCH OR DEVELOPMENT

This invention was made with United States government support awarded by the National Institutes of Health AI047446, AI069274. The United States government has certain rights in this invention.

BACKGROUND

Influenza epidemics and pandemics continue to claim human lives and impact the global economy. In the United States alone, influenza causes an estimated 50,000 deaths annually (Thompson et al., 2003), while global pandemics can result in millions of influenza-related deaths. A classic example is the so-called 'Spanish influenza', which killed an estimated 40-50 million people worldwide in 1918-1919 (Potter, 1998). The threat imposed by influenza virus has been further elevated with the recent introductions of avian influenza viruses into the human population. Avian influenza viruses were long thought not to be directly transmissible to humans and cause lethal outcomes. However, this perception changed in 1997, when 18 Hong Kong residents were infected by a wholly avian influenza virus of the H5N1 subtype, that resulted in 6 deaths (Subbarao et al., 1998; Claas et al., 1998). Over the next few years, several other cases of direct avian-to-human transmission were reported (Peiris et al., 2004; Fouchier et al., 2004; Koopsman et al., 2004), including the ongoing outbreak of highly pathogenic H5N1 influenza viruses in several Asian countries that has claimed 41 lives of 54 infected individuals as of Jan. 26, 2005 (WHO, 2004). The increasing numbers of human H5N1 virus infections, together with a high mortality rate and possible human-to-human transmission, make the development of vaccines to these viruses essential.

In the United States, two influenza vaccines are licensed for human use: an inactivated vaccine and a live attenuated vaccine virus. The production of influenza virus vaccines relies on reassortment (Gerdil, 2003), which requires coinfection of cells with a circulating wild-type strain that provides the hemagglutinin (HA) and neuraminidase (NA) segments and either A/PR/8/34 (PR8) virus (an attenuated human virus that provides high-growth properties in eggs) or a live attenuated virus that provides the attenuated phenotype. The selection of the desired "6+2" reassortants (i.e., those containing the HA and NA gene segments of the circulating wild-type strain in the genetic background of PR8 or live attenuated virus) is time-consuming and cumbersome. Moreover, the need for reassortment and selection, as well as the inability of some reassortant viruses to grow to high titers, have resulted in delays in vaccine production.

The artificial generation of influenza A and B viruses entirely from cloned cDNA in plasmid-transfected cells, the so-called "plasmid-based reverse genetics system" (Fodor et al., 1999; Neumann et al., 1999; Neumann et al., 2004; Neumann et al., 2002; Neumann et al., 1999; Hoffmann et al., 2002; Fodor et al., 1999; Hoffmann et al., 2000), represents an important advance for influenza virology. This technology has advanced both basic and applied research of influenza virus; most notably, the development of vaccine seed strains for highly pathogenic influenza viruses, including the currently circulating H5N1 viruses (Horimoto et al., 2006; Subbarao et al., 2003; Takada et al., 1999; Webby et al., 2004; Wood et al., 2004).

In one system (Neumann et al., 1999), eight plasmids encoding the eight influenza viral RNA segments under the control of the RNA polymerase I (PolI) promoter and terminator sequences are transfected into eukaryotic cells together with four RNA polymerase II (PolII)-driven plasmids for the expression of the three viral polymerase subunits and the nucleoprotein NP; these four proteins are required to initiate viral replication and transcription. An alternative system has been developed (Hoffmann et al., 2000) that relies on eight plasmids in which the viral cDNAs are flanked by an RNA polymerase I promoter on one site and an RNA polymerase II promoter on the other site, which permits the vRNA and mRNA to be derived from the same template. These systems have allowed 6+2 reassortants to be engineered without the need for reassortment and screening procedures.

Since at least eight plasmids have to be transfected into a single cell for virus generation, the limiting factor for plasmid-based reverse genetics is the transfection efficiency of the cells. In general, 293T cells, which are readily transfected with plasmids (Goto et al., 1997), have been used for plasmid-based systems (Hoffmann et al., 2000; Neumann et al., 1999). However, 293T cells cannot be used for the development of human vaccine seed strains because they are not validated for such use. African green monkey kidney (Vero) cells, which have been used for the production of rabies and polio virus vaccines (Montagnon et al., 1999), are the WHO-recommended cell line for vaccine production (Wood et al., 2004). Although these cells are not readily transfected (Kistner et al., 1998; Kistner et al., 1999a; Kistner et al., 1999b; Bruhl et al., 2000), the generation of influenza virus in Vero cells has been demonstrated (Fodor et al., 1999; Nicolson et al., 2005). Madin-Darby canine kidney (MDCK) cells (Brands et al., 1999; Palache et al., 1999; Halperin et al., 2002) are available for the production of influenza virus vaccine cells, but the cell line cannot be transfected with high efficiencies. It is, therefore, difficult to efficiently generate influenza viruses by using plasmid-based systems in influenza virus vaccine cells.

SUMMARY OF THE INVENTION

The invention provides a reverse genetics system for influenza virus generation that employs adenoviral vectors (AdVs), which achieves highly efficient gene transfer independent of cell transfection efficiency. As described hereinbelow, a reverse genetics system was established using adenovirus type 5-based gene transfer, a gene transfer system that has been safely administered in numerous clinical trials (see Young et al., 2006). An E1 and E3-deleted replication-incompetent adenoviral vector possessing the cDNAs of influenza viral RNA (vRNA) under the control of the human RNA polymerase I (PolI) promoter and the mouse PolI terminator, allowed efficient vRNA synthesis and led to a high virus yield in Vero cells. This AdV-mediated reverse genetics system is thus useful for generating vaccine seed strains and for basic influenza virus studies. In particular, the results suggest that the AdV-mediated system is valuable for the production of vaccine seed strains in pandemic situations. Moreover, the AdV-mediated system may be employed to generate other negative strand RNA viruses, including segmented negative strand RNA viruses.

In one embodiment, the invention provides a host cell infected with a plurality of recombinant adenovirus vectors having influenza virus sequences. The vectors include vectors for influenza virus vRNA production and vectors for influenza virus mRNA production. The vectors for influenza vRNA production comprise an adenovirus vector having a PolI promoter operably linked to an influenza virus PA DNA linked to a PolI transcription termination sequence (an adenovirus vector with an expression cassette), an adenovirus vector having a PolI promoter operably linked to an influenza virus PB1 DNA linked to a PolI transcription termination sequence, an adenovirus vector having a PolI promoter operably linked to an influenza virus PB2 DNA linked to a PolI transcription termination sequence, an adenovirus vector having a PolI promoter operably linked to an influenza virus HA DNA linked to a PolI transcription termination sequence, an adenovirus vector having a PolI promoter operably linked to an influenza virus NP DNA linked to a PolI transcription termination sequence, an adenovirus vector having a PolI promoter operably linked to an influenza virus NA DNA linked to a PolI transcription termination sequence, an adenovirus vector having a PolI promoter operably linked to an influenza virus M DNA linked to a PolI transcription termination sequence, and an adenovirus vector having a PolI promoter operably linked to an influenza virus NS DNA linked to a PolI transcription termination sequence. In one embodiment, separate adenovirus vectors for M1 and M2 vRNA, and/or for NS1 and NS2 vRNA, in place of adenovirus vectors for M vRNA and/or NS vRNA, are provided and employed in the compositions and methods of the invention. In one embodiment, one or more of the vectors for vRNA production, instead of having a PolI promoter, have a T7 RNA polymerase promoter (a "T7 promoter") and the host cell expresses T7 RNA polymerase. The host cell may stably or transiently express the T7 RNA polymerase, e.g., a construct expressing the T7 RNA polymerase may be integrated into the host cell genome or may be present on an extrachromosomal element, such as a plasmid. In one embodiment, where one or more of the vRNA vectors have a T7 promoter, the host cell may express a chimeric T7 RNA polymerase, e.g., one with a nuclear localization signal (see, e.g., de Wit et al., 2007). The vectors for mRNA production comprise an adenovirus vector having a PolII promoter operably linked to a DNA segment encoding influenza virus PA, an adenovirus vector having a PolII promoter operably linked to a DNA segment encoding influenza virus PB1, an adenovirus vector having a PolII promoter operably linked to a DNA segment encoding influenza virus PB2, and an adenovirus vector having a PolII promoter operably linked to a DNA segment encoding influenza virus NP. In one embodiment, the host cell is infected with all the adenovirus vectors except the NA vector, and the resulting virus is attenuated. In one embodiment, the host cell is infected with 11 adenovirus vectors, 4 for mRNA production and 7 for vRNA production where two of the expression cassettes are on the same adenovirus vector, e.g., NS DNA and M DNA are on the same vector.

The invention also provides a host cell infected with a plurality of adenovirus vectors for influenza virus production. The vectors comprise an adenovirus vector having a PolII promoter linked to a PolI transcription termination sequence linked to an influenza virus PA DNA linked to a PolI promoter linked to a PolII transcription termination sequence, an adenovirus vector having a PolII promoter linked to a PolI transcription termination sequence linked to an influenza virus PB1 DNA linked to a PolI promoter linked to a PolII transcription termination sequence, an adenovirus vector having a PolII promoter linked to a PolI transcription termination sequence linked to an influenza virus PB2 DNA linked to a PolI promoter linked to a PolII transcription termination sequence, an adenovirus vector having a PolII promoter linked to a PolI transcription termination sequence linked to an influenza virus HA DNA linked to a PolI promoter linked to a PolII transcription termination sequence, an adenovirus vector having a PolII promoter linked to a PolI transcription termination sequence linked to an influenza virus NP DNA linked to a PolI promoter linked to a PolII transcription termination sequence, an adenovirus vector having a PolII promoter linked to a PolI transcription termination sequence linked to an influenza virus NA DNA linked to a PolI promoter linked to a PolII transcription termination sequence, an adenovirus vector having a PolII promoter linked to a PolI transcription termination sequence linked to an influenza virus M DNA linked to a PolI promoter linked to PolII transcription termination sequence, and an adenovirus vector having a PolII promoter linked to a PolI transcription termination sequence linked to an influenza virus NS DNA linked to a PolI promoter linked to PolII transcription termination sequence. In one embodiment, separate adenovirus vectors for M1 and M2, and/or for NS1 and NS2, in place of adenovirus vectors for M and/or NS, in PolI and PolII transcription cassettes (bidirectional cassettes) are provided and employed in the compositions and methods of the invention. In one embodiment, the host cell is infected with all the adenovirus vectors except the NA vector. In one embodiment, instead of having a PolI promoter, one or more vRNA vectors have a T7 promoter. In one embodiment, where one or more of the vRNA vectors have a T7 promoter, the host cell may stably or transiently express the T7 RNA polymerase, e.g., express a chimeric T7 RNA polymerase.

In another embodiment, the invention provides a host cell infected with a plurality of recombinant adenovirus vectors with influenza virus sequences. The vectors include vectors for influenza virus vRNA production and vectors for influenza virus mRNA production. The vectors for influenza vRNA production comprise an adenovirus vector having a PolI promoter operably linked to an influenza virus PA DNA linked to a PolI transcription termination sequence, an adenovirus vector having a PolI promoter operably linked to an influenza virus PB1 DNA linked to a PolI transcription termination sequence, an adenovirus vector having a PolI promoter operably linked to an influenza virus PB2 DNA linked to a PolI transcription termination sequence, an adenovirus vector having a PolI promoter operably linked to an influenza virus HA DNA linked to a PolI transcription termination sequence, an adenovirus vector having a PolI promoter operably linked to an influenza virus NP DNA linked to a PolI transcription termination sequence, an adenovirus vector having a PolI promoter operably linked to an influenza virus NA and NB DNA linked to a PolI transcription termination sequence, an adenovirus vector having a PolI promoter operably linked to an influenza virus M DNA linked to a PolI transcription termination sequence, and an adenovirus vector having a PolI promoter operably linked to an influenza virus NS DNA linked to a PolI transcription termination sequence. In one embodiment, separate adenovirus vectors for NS1 and NS2 vRNA, in place of an adenovirus vector for NS vRNA, are provided and employed in the compositions and methods of the invention. In one embodiment, one or more of the vectors for vRNA production, instead of having a PolI promoter, have a T7 promoter. In one embodiment, where one or more of the vRNA vectors have a T7 promoter, the host cell expresses a T7 RNA polymerase, e.g., one with a nuclear localization signal. The host cell may stably or transiently express the T7 polymerase. The vectors for mRNA production include an adenovirus vector having a PolII promoter operably linked to a DNA segment encoding influenza virus PA, an adenovirus vector having a PolII promoter operably linked to a DNA segment encoding influenza virus PB1, an adenovirus vector having a PolII promoter operably linked to a DNA segment encoding influenza virus PB2, and an adenovirus vector having a PolII promoter operably linked to a DNA segment encoding influenza virus NP. In one embodiment, the host cell is infected with 11 adenovirus vectors, 4 for mRNA production and 7 for vRNA production where two of the expression cassettes are on the same adenovirus vector, e.g., NS DNA and M DNA are on the same vector.

Further provided is a host cell infected with a plurality of adenovirus vectors for influenza virus production. The vectors include an adenovirus vector having a PolII promoter linked to a PolI transcription termination sequence linked to an influenza virus PA DNA linked to a PolI promoter linked to a PolII transcription termination sequence, an adenovirus vector comprising a PolII promoter linked to a PolI transcription termination sequence linked to an influenza virus PB1 DNA linked to a PolI promoter linked to a PolII transcription termination sequence, an adenovirus vector having a PolII promoter linked to a PolI transcription termination sequence linked to an influenza virus PB2 DNA linked to a PolI promoter linked to a PolII transcription termination sequence, an adenovirus vector having a PolII promoter linked to a PolI transcription termination sequence linked to an influenza virus HA DNA linked to a PolI promoter linked to a PolII transcription termination sequence, an adenovirus vector having a PolII promoter linked to a PolI transcription termination sequence linked to an influenza virus NP DNA linked to a PolI promoter linked to a PolII transcription termination sequence, an adenovirus vector having a PolII promoter linked to a PolI transcription termination sequence linked to an influenza virus NA and NB DNA linked to a PolI promoter linked to a PolII transcription termination sequence, an adenovirus vector having a PolII promoter linked to a PolI transcription termination sequence linked to an influenza virus M DNA linked to a PolI promoter linked to PolII transcription termination sequence, and an adenovirus vector having a PolII promoter linked to a PolI transcription termination sequence linked to an influenza virus NS DNA linked to a PolI promoter linked to PolII transcription termination sequence. In one embodiment, separate adenovirus vectors for NS1 and NS2, in place of an adenovirus vector for NS, in PolI and PolII transcription cassettes are provided and employed in the compositions and methods of the invention. In one embodiment, instead of having a PolI promoter, one or more vRNA vectors have a T7 promoter. In one embodiment, where one or more of the vRNA vectors have a T7 promoter, the host cell stably or transiently expresses a T7 RNA polymerase.

Also provided is a recombinant adenovirus vector for vRNA production having a human or canine PolI promoter operably linked to an influenza virus PA DNA linked to a PolI transcription termination sequence; a recombinant adenovirus vector for vRNA production having a human or canine PolI promoter operably linked to an influenza virus PB1 DNA linked to a PolI transcription termination sequence; a recombinant adenovirus vector for vRNA production having a human or canine PolI promoter operably linked to an influenza virus PB2 DNA linked to a PolI transcription termination sequence; a recombinant adenovirus vector for vRNA production having a human or canine PolI promoter operably linked to an influenza virus NP DNA linked to a PolI transcription termination sequence; an adenovirus vector for vRNA production having a human or canine PolI promoter operably linked to an influenza virus HA DNA linked to a PolI transcription termination sequence; a recombinant adenovirus vector for vRNA production having a human or canine PolI promoter operably linked to an influenza virus NA DNA linked to a PolI transcription termination sequence; a recombinant adenovirus vector for vRNA production having a human or canine PolI promoter operably linked to an influenza virus M1 DNA linked to a PolI transcription termination sequence; a recombinant adenovirus vector for vRNA production having a human or canine PolI promoter operably linked to an influenza virus M2 DNA linked to a PolI transcription termination sequence; a recombinant adenovirus vector for vRNA production having a human or canine PolI promoter operably linked to an influenza virus NS2 DNA linked to a PolI transcription termination sequence; a recombinant adenovirus vector for vRNA production having a human or canine PolI promoter operably linked to an influenza virus NS1 DNA linked to a PolI transcription termination sequence; a recombinant adenovirus vector for vRNA production having a human or canine PolI promoter operably linked to an influenza virus M DNA linked to a PolI transcription termination sequence; and/or a recombinant adenovirus vector for vRNA production having a human or canine PolI promoter operably linked to an influenza virus NS DNA linked to a PolI transcription termination sequence. Further provided are bidirectional adenovirus vectors for influenza virus production, where an influenza virus DNA for a viral protein is flanked by a PolI promoter and a PolI transcription termination sequence and a PolII promoter and PolII transcription termination sequence. In one embodiment, one or more of the vectors for vRNA production, instead of having a PolI promoter, have a T7 promoter.

In one embodiment, the invention provides a host cell infected with a plurality of recombinant retrovirus vectors having influenza virus sequences. The vectors include vectors for influenza virus vRNA production and vectors for influenza virus mRNA production. The vectors for influenza vRNA production comprise a retrovirus vector having a PolI promoter operably linked to an influenza virus PA DNA linked to a PolI transcription termination sequence (a retrovirus vector with an expression cassette), a retrovirus vector having a PolI promoter operably linked to an influenza virus PB1 DNA linked to a PolI transcription termination sequence, a retrovirus vector having a PolI promoter operably linked to an influenza virus PB2 DNA linked to a PolI transcription termination sequence, a retrovirus vector having a PolI promoter operably linked to an influenza virus HA DNA linked to a PolI transcription termination sequence, a retrovirus vector having a PolI promoter operably linked to an influenza virus NP DNA linked to a PolI transcription termination sequence, a retrovirus vector having a PolI promoter operably linked to an influenza virus NA DNA linked to a PolI transcription termination sequence, a retrovirus vector having a PolI promoter operably linked to an influenza virus M DNA linked to a PolI transcription termination sequence, and a retrovirus vector having a PolI promoter operably linked to an influenza virus NS DNA linked to a PolI transcription termination sequence. In one embodiment, separate retrovirus vectors for M1 and M2 vRNA, and/or for NS1 and NS2 vRNA, in place of retrovirus vectors for M vRNA and/or NS vRNA, are provided and employed in the compositions and methods of the invention. In one embodiment, one or more of the vectors for vRNA production, instead of having a PolI promoter, have a T7 promoter and the host cell transiently or stably expresses a T7 RNA polymerase, e.g., one with a nuclear localization signal. The vectors for mRNA production comprise a retrovirus vector having a PolII promoter operably linked to a DNA segment encoding influenza virus PA, a retrovirus vector having a PolII promoter operably linked to a DNA segment encoding influenza virus PB1, a retrovirus vector having a PolII promoter operably linked to a DNA segment encoding influenza virus PB2, and a retrovirus vector having a PolII promoter operably linked to a DNA segment encoding influenza virus NP. In one embodiment, the host cell is infected with all the retrovirus vectors except the NA vector. In one embodiment, the host cell is infected with 11 retrovirus vectors, 4 for mRNA production and 7 for vRNA production where two of the expression cassettes are on the same retrovirus vector, e.g., NS DNA and M DNA are on the same vector.

The invention also provides a host cell infected with a plurality of retrovirus vectors for influenza virus production. The vectors comprise a retrovirus vector having a PolII promoter linked to a PolI transcription termination sequence linked to an influenza virus PA DNA linked to a PolI promoter linked to a PolII transcription termination sequence, a retrovirus vector having a PolII promoter linked to a PolI transcription termination sequence linked to an influenza virus PB1 DNA linked to a PolI promoter linked to a PolII transcription termination sequence, a retrovirus vector having a PolII promoter linked to a PolI transcription termination sequence linked to an influenza virus PB2 DNA linked to a PolI promoter linked to a PolII transcription termination sequence, a retrovirus vector having a PolII promoter linked to a PolI transcription termination sequence linked to an influenza virus HA DNA linked to a PolI promoter linked to a PolII transcription termination sequence, a retrovirus vector having a PolII promoter linked to a PolI transcription termination sequence linked to an influenza virus NP DNA linked to a PolI promoter linked to a PolII transcription termination sequence, a retrovirus vector having a PolII promoter linked to a PolI transcription termination sequence linked to an influenza virus NA DNA linked to a PolI promoter linked to a PolII transcription termination sequence, a retrovirus vector having a PolII promoter linked to a PolI transcription termination sequence linked to an influenza virus M DNA linked to a PolI promoter linked to PolII transcription termination sequence, and a retrovirus vector having a PolII promoter linked to a PolI transcription termination sequence linked to an influenza virus NS DNA linked to a PolI promoter linked to PolII transcription termination sequence. In one embodiment, the host cell is infected with all the retrovirus vectors except the NA vector. In one embodiment, separate retrovirus vectors for M1 and M2, and/or for NS1 and NS2, in place of retrovirus vectors for M and/or NS, in PolI and PolII transcription cassettes are provided and employed in the compositions and methods of the invention. In one embodiment, instead of having a PolI promoter, one or more vRNA vectors have a T7 promoter, and the host cell stably or transiently expresses a T7 RNA polymerase, e.g., one with a nuclear localization signal.

In another embodiment, the invention provides a host cell infected with a plurality of recombinant retrovirus vectors with influenza virus sequences. The vectors include vectors for influenza virus vRNA production and vectors for influenza virus mRNA production. The vectors for influenza vRNA production comprise a retrovirus vector having a PolI promoter operably linked to an influenza virus PA DNA linked to a PolI transcription termination sequence, a retrovirus vector having a PolI promoter operably linked to an influenza virus PB1 DNA linked to a PolI transcription termination sequence, a retrovirus vector having a PolI promoter operably linked to an influenza virus PB2 DNA linked to a PolI transcription termination sequence, a retrovirus vector having a PolI promoter operably linked to an influenza virus HA DNA linked to a PolI transcription termination sequence, a retrovirus vector having a PolI promoter operably linked to an influenza virus NP DNA linked to a PolI transcription termination sequence, a retrovirus vector having a PolI promoter operably linked to an influenza virus NA and NB DNA linked to a PolI transcription termination sequence, a retrovirus vector having a PolI promoter operably linked to an influenza virus M DNA linked to a PolI transcription termination sequence, and a retrovirus vector having a PolI promoter operably linked to an influenza virus NS DNA linked to a PolI transcription termination sequence. In one embodiment, separate retrovirus vectors for NS1 and NS2 vRNA, in place of a retrovirus vector for NS vRNA, are provided and employed in the compositions and methods of the invention. In one embodiment, one or more of the vectors for vRNA production, instead of having a PolI promoter, have a T7 promoter, and the host cell stably or transiently expresses a T7 RNA polymerase, e.g., one with a nuclear localization signal. The vectors for mRNA production include a retrovirus vector having a PolII promoter operably linked to a DNA segment encoding influenza virus PA, a retrovirus vector having a PolII promoter operably linked to a DNA segment encoding influenza virus PB1, a retrovirus vector having a PolII promoter operably linked to a DNA segment encoding influenza virus PB2, and a retrovirus vector having a PolII promoter operably linked to a DNA segment encoding influenza virus NP. In one embodiment, the host cell is infected with 11 retrovirus vectors, 4 for mRNA production and 7 for vRNA production where two of the expression cassettes are on the same retrovirus vector, e.g., NS DNA and M DNA are on the same vector.

Further provided is a host cell infected with a plurality of retrovirus vectors for influenza virus production. The vectors include a retrovirus vector having a PolII promoter linked to a PolI transcription termination sequence linked to an influenza virus PA DNA linked to a PolI promoter linked to a PolII transcription termination sequence, a retrovirus vector comprising a PolII promoter linked to a PolI transcription termination sequence linked to an influenza virus PB1 DNA linked to a PolI promoter linked to a PolII transcription termination sequence, a retrovirus vector having a PolII promoter linked to a PolI transcription termination sequence linked to an influenza virus PB2 DNA linked to a PolI promoter linked to a PolII transcription termination sequence, a retrovirus vector having a PolII promoter linked to a PolI transcription termination sequence linked to an influenza virus HA DNA linked to a PolI promoter linked to a PolII transcription termination sequence, a retrovirus vector having a PolII promoter linked to a PolI transcription termination sequence linked to an influenza virus NP DNA linked to a PolI promoter linked to a PolII transcription termination sequence, a retrovirus vector having a PolII promoter linked to a PolI transcription termination sequence linked to an influenza virus NA and NB DNA linked to a PolI promoter linked to a PolII transcription termination sequence, a retrovirus vector having a PolII promoter linked to a PolI transcription termination sequence linked to an influenza virus M DNA linked to a PolI promoter linked to PolII transcription termination sequence, and a retrovirus vector having a PolII promoter linked to a PolI transcription termination sequence linked to an influenza virus NS DNA linked to a PolI promoter linked to PolII transcription termination sequence. In one embodiment, separate retrovirus vectors for NS1 and NS2, in place of a retrovirus vector for NS, in PolI and PolII transcription cassettes are provided and employed in the compositions and methods of the invention. In one embodiment, instead of having a PolI promoter, one or more vRNA vectors have a T7 promoter, and the host cell stably or transiently expresses a T7 RNA polymerase, e.g., one with a nuclear localization signal.

Also provided is a recombinant retrovirus vector for vRNA production having a human or canine PolI promoter operably linked to an influenza virus PA DNA linked to a PolI transcription termination sequence; a recombinant retrovirus vector for vRNA production having a human or canine PolI promoter operably linked to an influenza virus PB1 DNA linked to a PolI transcription termination sequence; a recombinant retrovirus vector for vRNA production having a human or canine PolI promoter operably linked to an influenza virus PB2 DNA linked to a PolI transcription termination sequence; a recombinant retrovirus vector for vRNA production having a human or canine PolI promoter operably linked to an influenza virus NP DNA linked to a PolI transcription termination sequence; a retrovirus vector for vRNA production having a human or canine PolI promoter operably linked to an influenza virus HA DNA linked to a PolI transcription termination sequence; a recombinant retrovirus vector for vRNA production having a human or canine PolI promoter operably linked to an influenza virus NA DNA linked to a PolI transcription termination sequence; a recombinant retrovirus vector for vRNA production having a human or canine PolI promoter operably linked to an influenza virus M1 DNA linked to a PolI transcription termination sequence; a recombinant retrovirus vector for vRNA production having a human or canine PolI promoter operably linked to an influenza virus M2 DNA linked to a PolI transcription termination sequence; a recombinant retrovirus vector for vRNA production having a human or canine PolI promoter operably linked to an influenza virus NS2 DNA linked to a PolI transcription termination sequence; a recombinant retrovirus vector for vRNA production having a human or canine PolI promoter operably linked to an influenza virus M DNA linked to a PolI transcription termination sequence; a recombinant retrovirus vector for vRNA production having a human or canine PolI promoter operably linked to an influenza virus NS1 cDNA linked to a PolI transcription termination sequence; and/or a recombinant retrovirus vector for vRNA production having a human or canine PolI promoter operably linked to an influenza virus NS cDNA linked to a PolI transcription termination sequence. Further provided are bidirectional retrovirus vectors for influenza virus production where an influenza virus DNA for a viral protein is flanked by a PolI promoter and a PolI transcription termination sequence and a PolII promoter and PolII transcription termination sequence.

Further provided are methods of using the host cells of the invention, e.g., useful to produce influenza virus or screen for anti-virals. In the event of a new influenza pandemic, vaccines whose antigenicities match circulating strains must be rapidly produced. In one embodiment, the host cells of the invention are cell lines, e.g., Vero cells or MDCK cells, capable of being infected with adenovirus, retrovirus, or both.

As described hereinbelow, an alternative reverse genetics system for influenza virus was generated using the canine polymerase I (PolI) promoter sequence that is transcribed efficiently in the Madin-Darby canine kidney (MDCK) cell line, a cell line approved for human vaccine production. Using this system, H5N1 vaccine seed viruses were produced that were more robust than those generated with a system that uses the human PolI promoter in African green monkey Vero cells, thus improving pandemic vaccine production. Thus, for enhanced expression of vRNA sequences in MDCK cells, a canine PolI promoter (e.g., comprising 5'-CGTGGCGTCTC-CACCGACCGCGTATCGCCCCTCCTCAC-CCCCCCCCCCCC CGGTTTCCCTGGGTCGACCAGAT-AGCCCTGGGGGCTCCGTGGGGTGGAG GTGGGGGGGCGCCGTGGGGCAG-GTTTTGGGTACAGTTGGCCGTGTCACG GTCCCGG-GAGGTCGCGGTGACCTGTGGCTGGTC-CCCGCCGGCAGGCGCG GTTATTTTCTTGCCCGAAATGAA-CATTTTTTGTTGCCAGGTAGGTCCGCC GGCAG-GCGCGGTTATTTTCTTGCCCGAAATGAA-CATTTTTTGTTGCCAGG TAGGT-3' (SEQ ID NO:15) or a sequence with 80%, 85%, 90% or more, e.g., 95%, 97%, 98% or 99%, identity thereto, or a fragment thereof, e.g., a fragment of 50, 75, 100, 150, 200, 250, or 275 nucleotides, or a fragment of 50, 75, 100, 150, 200, 250, or 300 nucleotides of SEQ ID NO:16 (see FIG. 6C), or any integer between 50 and 300, that initiates transcription by canine RNA polymerase I, may be employed. The host cells of the invention may produce at least 10,000 pfu/mL, e.g., at least 50,000, 75,000 pfu/mL or more, for instance, over 100,000 pfu/mL.

The invention provides an isolated polynucleotide having a PolI promoter having at least 90% nucleic acid sequence identity to SEQ ID NO:15 or SEQ ID NO:16 and a chimeric expression cassette having the PolI promoter operably linked to nucleic acid having sequences corresponding to an open reading frame.

Host cells of the invention may be infected with one or more adenovirus vectors or retrovirus vectors of the invention and optionally transfected (stably or transiently) with another vector, e.g., a plasmid vector, having an expression cassette that expresses one or more influenza virus vRNAs or mRNAs. For example, a retrovirus vector may be employed to deliver HA and NA sequences from a circulating virus strain to a cell while one or more plasmids that produce vRNA or mRNA for the other viral segments may be introduced to the cell, so that influenza virus is produced from the cell. In another embodiment, a retrovirus vector may be employed to deliver HA sequences from a circulating virus strain to a cell while one or more plasmids that produce vRNA or mRNA for the other viral segments may be introduced to the cell, so that influenza virus is produced from the cell. In yet another embodiment, combinations of adenovirus and retrovirus vectors are employed to transduce a host cell. For instance, a host cell is transduced with retrovirus vectors for protein production of influenza virus PA, PB1, PB2, and NP, and retrovirus vectors for vRNA production of all genes but NA and HA. Such a host cell may then be transduced with adenovirus vectors expressing HA and NA.

BRIEF DESCRIPTION OF THE FIGURES

FIG. 1. Schematic diagrams of the transcription cassette of pPolI and AdVs for reporter vRNA synthesis. In pPolI-GFP (Neumann et al., 2000), the 3' noncoding region of NP vRNA (3' NCR), the GFP open reading frame in the negative sense, and the 5' noncoding region of NP vRNA (5' NCR) were inserted between the PolI promoter ($P_{PolI}$) and the PolI terminator ($T_{PolI}$). In cells transfected with pPolI-GFP, the reporter vRNA containing the GFP gene is synthesized by cellular PolI (A). AdV/PolI-GFP possessed the same transcription cassette of pPolI-GFP for reporter vRNA synthesis (B). The vRNA transcriptional region in AdV/CMV-PolI-GFP was flanked by the human cytomegalovirus immediate early promoter ($P_{CMV}$) and the herpes simplex virus thymidine kinase polyadenylation signal (TK pA). In cells transduced with AdV/CMV-PolI-GFP, the reporter vRNA and mRNA containing the GFP genes are synthesized by cellular PolI and PolII, respectively. The backbone of the adenoviral clones (Ad) was an E1 and E3-deleted adenovirus type 5 genome. The transcriptional initiation site and orientation is indicated by the white arrow.

Figure 2:
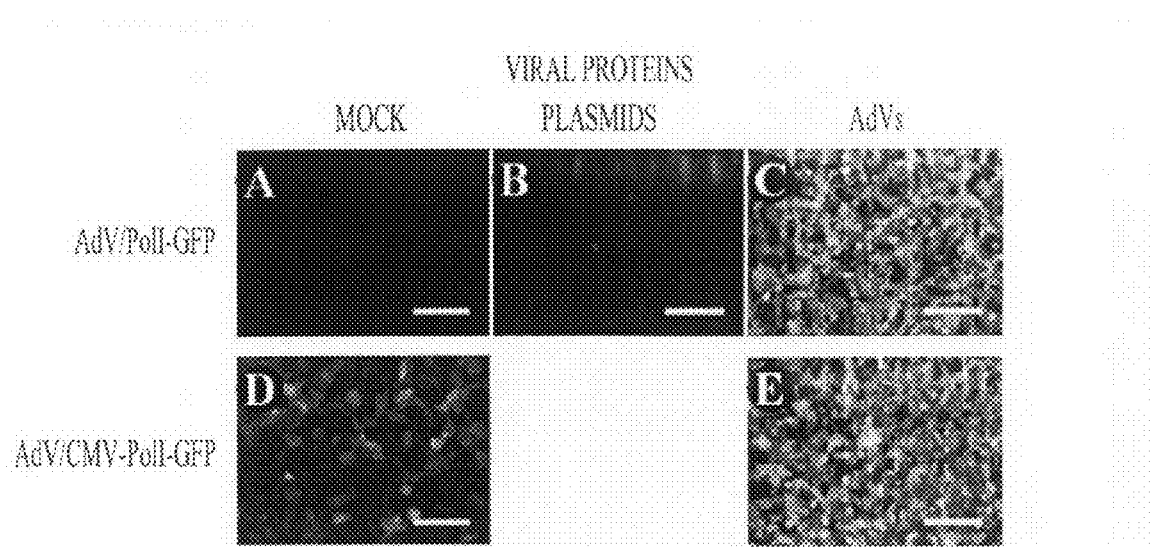

FIG. 2. GFP expression in Vero cells transduced with AdVs for reporter vRNA synthesis. Vero cells were transduced with AdV/PolI-GFP (A-C) and AdV/CMV-PolI-GFP (D and E). Simultaneously, the cells were transfected with plasmids (B) or transduced with AdVs for the expression of the polymerase subunits (PB2, PB1, and PA) and NP. Forty-eight hours later, GFP expression was examined by fluorescence microscopy. In each experiment, each AdV was transduced at an MOI of 50. The image in panel D was taken with a 10-fold longer exposure time than those in the other panels. Scale bar, 200 µm.

Figure 3:
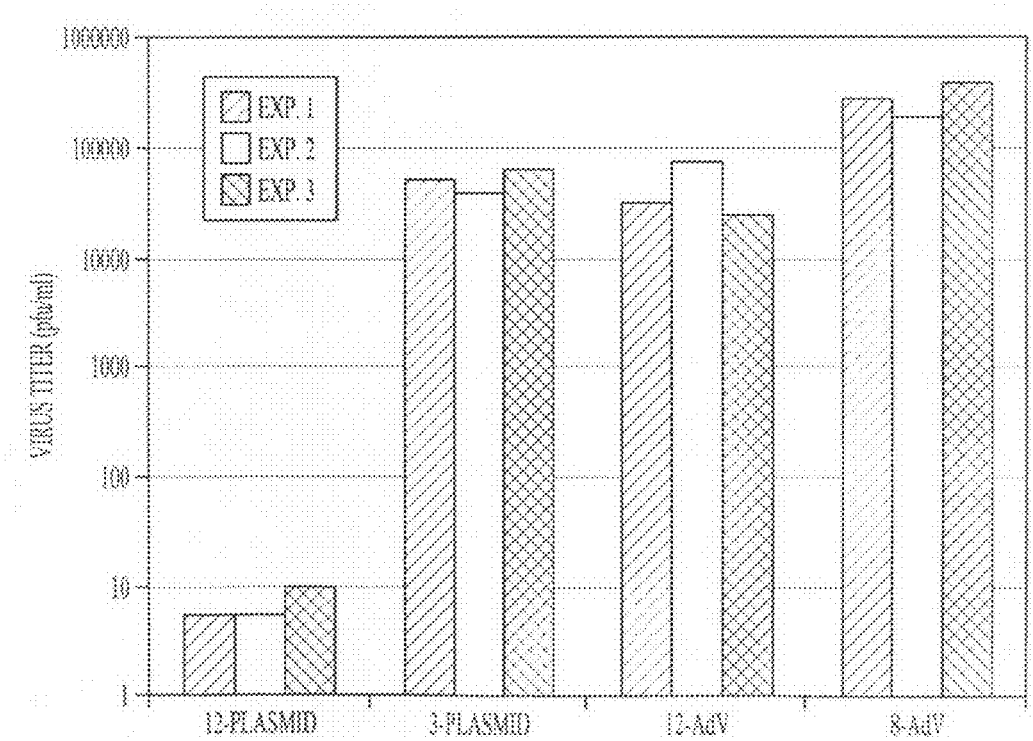

FIG. 3. Comparison of the virus generation efficiency of plasmid transfection systems and AdV transduction systems. Vero cells were transfected with 12-plasmids (Neumann et al., 2002), or 3-plasmids [pTM-PolI-WSN-All, pC-PolII-WSN-PB2-PB1-PA, and pCAWS-NP (Neumann et al., 2005)], or transduced with 12-AdVs (AdV/PolI-PB2, -PB1, -PA, -HA, -NP, -NA, -M, and -NS, and AdV/CMV-PB2, -PB1, -PA, and -NP) or 8-AdVs (AdV/CMV-PolI-PB2, -PB1, -PA, -HA, -NP, -NA, -M, and -NS). Seventy-two hours later, virus titers in culture supernatant were determined by plaque assay on MDCK cells. The results of three independent experiments are shown.

Figure 4:
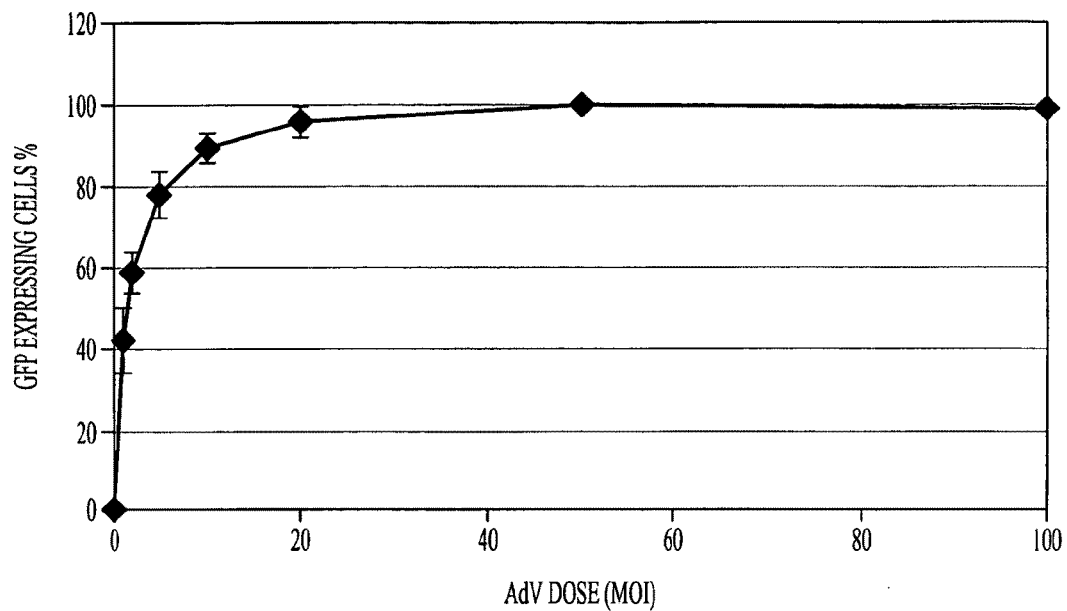

FIG. 4. Assessment of the optimal MOI of AdV for the expression of the reporter protein. Vero cells were transduced with AdV for the expression of GFP at different MOI. At 48 hours after transduction, the GFP expressing cells were assessed by fluorescence-activated cell sorter (FACS) analysis using FACScalibur (Becton Dickinson, Heidelberg, Germany) and the CellQuest software (Becton Dickinson). Error bars indicate the standard errors of the deviations (SDs) of three independent experiments.

Figure 5:
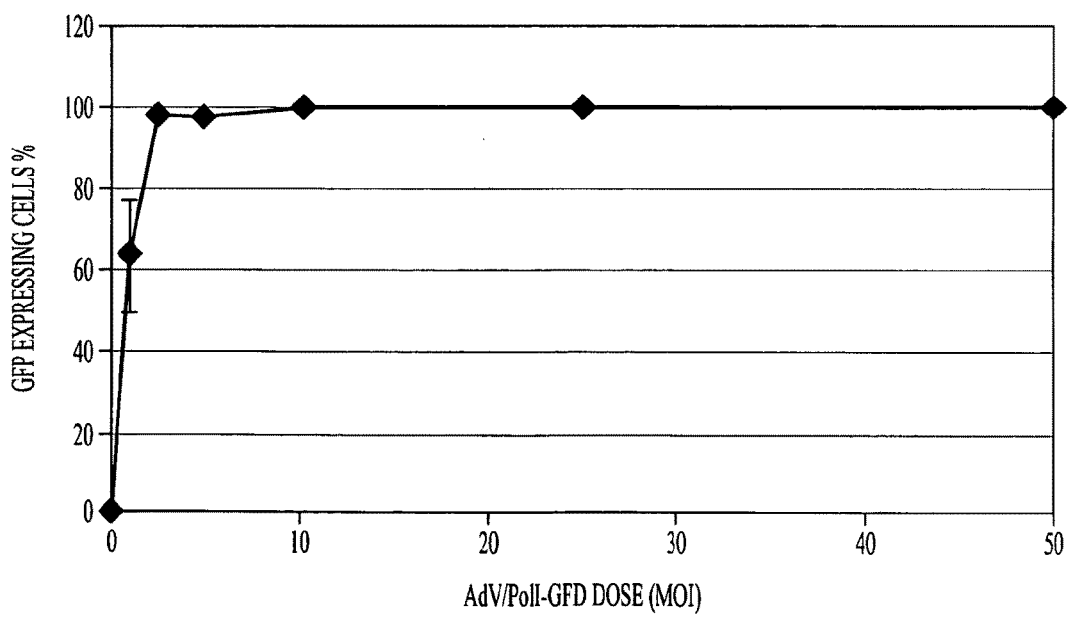

FIG. 5. Assessment of the optimal MOI of AdV for the synthesis of the reporter vRNA. Vero cells were cotransduced with AdV/PolI-GFP at different MOI and AdV/CMV-PB2, -PB1, -PA, and -NP. At 48 hours after transduction, the GFP expressing cells were assessed by FACS analysis using FACScalibur and the CellQuest software. Error bars indicate SDs of three independent experiments.

FIG. 6. Cloning of the canine PolI promoter. (A) Molecular map of the canine rDNA. Head to tail repeats of rRNA genes (18, 5.8, and 28S rRNA) are separated by intergenic spacers (IGS) containing the PolI promoter and terminator regions. The PolI promoter region is located directly upstream of the 5'-external transcribed spacer (5' ETS) and the terminator region is located downstream of the 3'-external transcribed spacer (3' ETS). The transcription initiation site is indicated as +1. (B) Alignment of the PolI transcription start regions (nt −8 to +11), as predicted by computer analysis, of canine (underlined) and other species (SEQ ID NOs:1-7). The transcription initiation site is indicated as +1. (C) Sequences of the canine PolI promoter regions as predicted by computer analysis (SEQ ID NO:16). The region (nt −457 to +1) was cloned from genomic DNA of MDCK cells by using specific primers indicated by the arrows (solid line for nt −457 to +1 and broken line for nt −250 to +1). The cloned sequence was aligned with the canine genomic DNA sequence (GenBank accession No. NW_878945; SEQ ID NO:8).

Figure 7B:
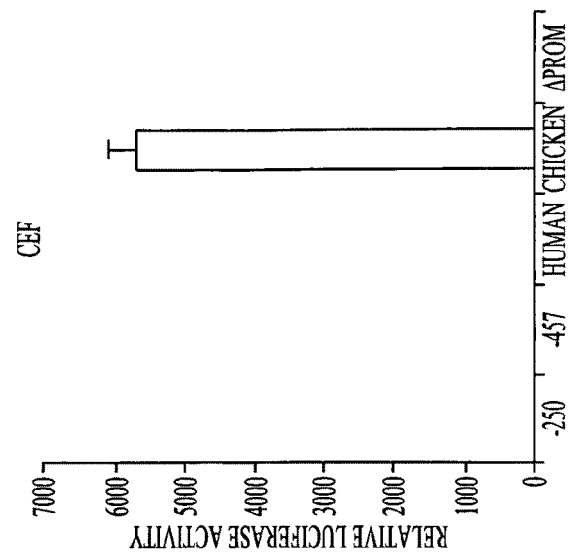
Figure 7B:
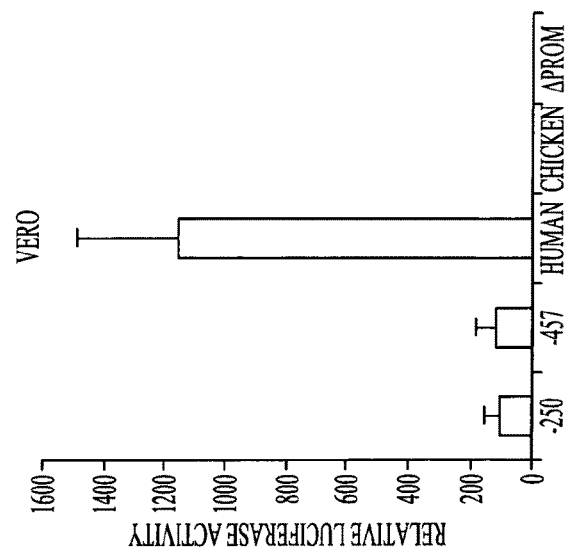
Figure 7C:
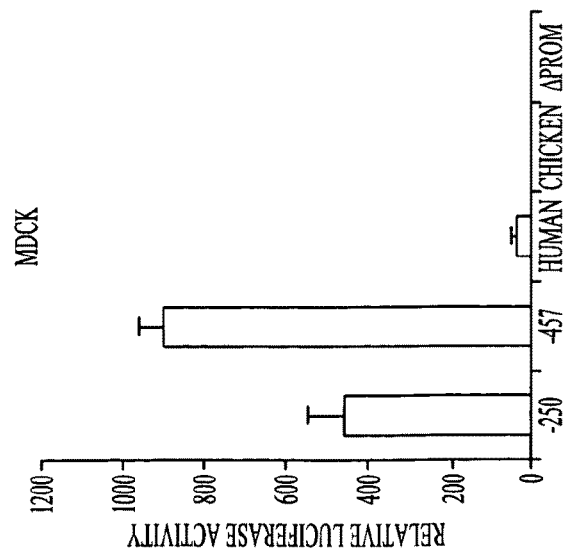

FIG. 7. RNA polymerase I promoter activities in MDCK, Vero cells, and CEF measured by the expression of a luciferase reporter gene. MDCK, Vero cells, and CEF were transfected with reporter plasmids encoding a firefly luciferase gene inserted between the 3' and 5' non-coding regions of the NP segment of A/Purto Rico/8/34 (PR8) under the control of the canine PolI promoter (pPolIC250-NP(0)Fluc(0) or pPolIC457-NP(0)Fluc(0)), the human PolI promoter (pPolI-NP(0)Fluc(0)), the chicken PolI promoter (pPolGG250-NP(0)Fluc(0)), or without a PolI promoter (pΔ-PolIprom-NP(0)Fluc(0)), together with the four plasmids that express PB2, PB1, PA, and NP from PR8. At 12 hours after transfection, cells were subjected to the Dual-luciferase assay (Promega). PolI promoter activities, represented as ratios of firefly luciferase to Renilla luciferase (as an internal control), are shown. The data presented are the mean (standard deviation) of triplicate samples.

DETAILED DESCRIPTION OF THE INVENTION

Definitions

As used herein, the terms "isolated and/or purified" refer to in vitro preparation, isolation and/or purification of a nucleic acid molecule such as a plasmid of the invention or a virus of the invention, so that it is not associated with in vivo substances, or is substantially purified from in vitro substances. An isolated virus preparation is generally obtained by in vitro culture and propagation and is substantially free from other infectious agents. As used herein, "substantially free" means below the level of detection for a particular infectious agent using standard detection methods for that agent. A "recombinant" virus is one which has been manipulated in vitro, e.g., using recombinant DNA techniques, to introduce changes to the viral genome, or otherwise artificially generated. As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

A "highly transfectable cell" as used herein is a cell where transfection efficiencies with a single plasmid reach about 95%, e.g., as measured by protein expression in transfected cells and/or where transfection with more than 5 plasmids with influenza viral genes for virus production of a nonattenuated influenza virus, yields a virus titer of at least about $10^6$ TCID$_{50}$/mL by day 2 post-transfection or of an attenuated virus yields a virus titer of about $10^2$ TCID$_{50}$/mL. Exemplary highly transfectable cells include but are not limited to 293T cells. In contrast, a "cell with reduced transfection efficiency" as used herein is a cell wherein transfection efficiencies with a single plasmid are less than about 50% and/or where transfection with more than 5 plasmids with influenza viral genes for virus production of a nonattenuated influenza virus, yields a virus titer of less than about $3\times10^5$ TCID$_{50}$/mL by 2 days after transfection. Exemplary cells with reduced transfection efficiency include but are not limited to Vero cells and MDCK cells.

Negative-Sense RNA Viruses

Negative-sense RNA viruses are classified into seven families (Rhabdoviridae, Paramyxoviridae, Filoviridae, Bornaviridae, Orthomyxoviridae, Bunyaviridae, and Arenaviridae) which include common human pathogens, such as respiratory syncytial virus, influenza virus, measles virus, and Ebola virus, as well as animal viruses with major economic impact on the poultry and cattle industries (e.g., Newcastle disease virus and Rinderpest virus). The first four families are characterized by nonsegmented genomes, while the latter three have genomes comprised of six-to-eight, three, or two negative-sense RNA segments, respectively. The common feature of negative-sense RNA viruses is the negative polarity of their RNA genome; i.e., the viral RNA (vRNA) is complementary to mRNA and therefore is not infectious by itself. In order to initiate viral transcription and replication, the vRNA has to be transcribed into a plus-sense mRNA or cRNA, respectively, by the viral polymerase complex and the nucleoprotein; for influenza A viruses, the viral polymerase complex is comprised of the three polymerase proteins PB2, PB1, and PA. During viral replication, cRNA serves as a template for the synthesis of new vRNA molecules. For all negative-stranded RNA viruses, non-coding regions at both the 5' and 3' termini of the vRNA and cRNA are critical for transcription and replication of the viral genome. Unlike cellular or viral mRNA transcripts, both cRNA and vRNA are neither capped at the 5' end nor polyadenylated at the very 3' end.

The basic functions of many viral proteins have been elucidated biochemically and/or in the context of viral infection. However, reverse genetics systems have dramatically increased our knowledge of negative-stranded segmented and non-segmented RNA viruses with respect to their viral replication and pathogenicity, as well as to the development of live attenuated virus vaccines. Reverse genetics, as the term is used in molecular virology, is defined as the generation of virus possessing a genome derived from cloned cDNAs (for a review, see Neumann et al., 2002).

Influenza Virus

Influenza A viruses possess a genome of eight single-stranded negative-sense viral RNAs (vRNAs) that encode a total of ten to eleven proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cDNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, the M segment of influenza B virus encodes two proteins, M1 and BM2, through a termination-reinitiation scheme of tandem cistrons, and the NA segment encodes the NA and NB proteins from a bicistronic mRNA. Influenza C virus, which has 7 vRNA segments, relies on spliced transcripts to produce M1 protein; the product of the unspliced mRNA is proteolytically cleaved to yield the CM2 protein. In addition, influenza C virus encodes a HA-esterase (HEF) rather than individual HA and NA proteins.

Thogotovirus

Thogotoviruses (THOV) represent a new genus in the family of Orthomyxoviridae. They are transmitted by ticks and have been found in domestic animals, including camels, goats, and cattle. Consequently, THOV can replicate in tick and vertebrate cells. The THOV genome comprises six segments of single-stranded, negative-sense RNA. The proteins encoded by the three largest segments show significant homology to the influenza virus polymerase proteins PB2, PB1, and PA. Segment 5 encodes a protein related to influenza virus NP. The THOV glycoprotein, which is encoded by segment 4, is not homologous to either influenza virus HA or NA, but it shows sequence similarity to the Baculovirus glycoprotein. The smallest segment is thought to encode a matrix protein and does not resemble any of the influenza virus proteins. Like influenza virus, both the 3' and 5' ends of the vRNA are required for promoter activity, and this activity is located in the terminal 14 and 15 nucleotides of the 3' and 5' ends of the vRNA, respectively.

The mRNA synthesis of THOV is primed by host cell-derived cap structures. However, in contrast to influenza virus, only the cap structures (without additional nucleotides) are cleaved from cellular mRNAs (Albo et al., 1996; Leahy et al., 1997; Weber et al., 1996). In vitro cleavage assays revealed that both the 5' and 3' ends of vRNA are required for endonuclease activity (Leahy et al., 1998), but addition of a model cRNA promoter does not stimulate endonuclease activity (Leahy et al., 1998), as has been shown for influenza virus (Hagen et al., 1994). A 'hook' structure has been proposed for THOV (Leahy et al., 1997; Weber et al., 1997), which is similar to the corkscrew structure proposed for influenza virus. This 'hook' structure, however, is only found in the THOV vRNA promoter. The cRNA promoter sequence does not allow the formation of base pairs between positions 2 and 9, and between 3 and 8 at the 5' end of the cRNA. Alterations at positions 3 or 8 to allow base-pairing between these nucleotides stimulates endonuclease activity, which is strong supporting evidence of the proposed 'hook' structure (Leahy et al., 1998). Moreover, this structure might be crucial for the regulation of the THOV life cycle; the vRNA promoter, forming the 'hook' structure, may stimulate PB2 endonuclease activity, thereby allowing transcription. The cRNA promoter, in contrast, may not form the 'hook' structure and may therefore be unable to stimulate endonuclease activity, thus resulting in replication.

Bunyaviridae

The family Bunyaviridae includes several viruses that cause hemorrhagic or encephalitic fevers in humans (e.g., Rift fever valley, Hantaan, La Crosse, and Crimean-Congo hemorrhagic fever). The spherical and enveloped virions contain three segments of single-stranded, negative-sense RNA (reviewed in Elliott, 1997). The largest segment (L) encodes the viral RNA polymerase protein (L protein), whereas the M segment encodes the two viral glycoproteins G1 and G2, and a nonstructural protein (NSm). The smallest segment (S) encodes the nucleocapsid protein (N) and a second nonstructural protein (NSs). Virus replication and transcription take place in the cytoplasm, and newly assembled virions bud through the membranes of the Golgi apparatus.

Bridgen & Elliott (1996) have established a reverse genetics system to generate infectious Bunyamwera virus entirely from cloned cDNAs. They followed a strategy first described by Schnell et al. (1994) for rabies virus: intracellular transcription of a cDNA coding for the positive-sense antigenomic RNA (but not for the negative-sense genomic RNA) in cells expressing the viral polymerase and nucleoprotein. Bridgen & Elliott (1996) infected HeLaT4+ cells with vaccinia virus expressing T7 polymerase and transfected these cells with plasmids expressing proteins encoded by the S, M, and L segments. They then transfected these cells with three plasmids encoding full-length anti-genomic cDNAs flanked by the T7 polymerase promoter and the hepatitis delta virus ribozyme. To increase the number of bunyavirus particles relative to the number of vaccinia virus particles, the authors used mosquito cells in which Bunyamwera but not Vaccinia virus replicates. This protocol can be used not only to genetically engineer Bunyaviridae, but also generate reassortant viruses that cannot easily be obtained by coinfecting cells with different Bunyaviridae strains.

To study bunyavirus promoter elements and the viral proteins that are required for transcription and replication, Dunn et al. (1995) cloned the CAT gene in the negative-sense orientation between the 5' and 3' nontranslated regions of the Bunyamwera S RNA segment. Cells were transfected with constructs expressing the proteins encoded by the L and S segment and were then transfected with in vitro transcribed RNA, which resulted in CAT activity. The bunyavirus S segment encodes two proteins, N and NSs, in overlapping reading frames. To determine whether both of these proteins are required for transcription and replication, constructs expressing only N or NSs were tested for CAT activity. N protein expression, together with L protein, resulted in CAT activity, whereas no CAT activity was detected with the NSs expression construct. Thus, the L and N proteins are sufficient for transcription and replication of a bunyavirus-like RNA.

As with influenza virus, the terminal sequences of bunyavirus RNAs are complementary and highly conserved. It has therefore been assumed that these sequence elements define the bunyaviral promoter and are crucial for promoter activity. Deletion of five nucleotides at the 3' end of the viral RNA drastically reduces CAT expression (Dunn et al., 1995). In contrast, addition of two nucleotides at the 5' end, or of 11 or 35 nucleotides at the 3' end does not abolish CAT expression (Dunn et al., 1995). Therefore, like the influenza virus polymerase complex, the bunyavirus polymerase protein can apparently start transcription and/or replication internally.

Recombinant Adenovirus and Retrovirus Vectors of the Invention

The use of the adenovirus and retrovirus vectors may significantly enhance the introduction of influenza virus sequences to cells for the generation of influenza virus, particularly in the cell lines that cannot be transfected with high efficiencies, including cell lines for the production of human vaccines (e.g., Vero cells). Accordingly, the use of the adenovirus or retrovirus vectors, e.g., helper-free stocks, of the invention may provide for the speedy generation of vaccine viruses, especially for pandemics in cell lines for the production of human vaccines. In one embodiment, the use of adenovirus vectors significantly increases the rescue efficiency of influenza virus in cell lines that cannot be transfected with high efficiencies, allowing the generation of viruses that are severely attenuated, and/or allowing for the generation of influenza virus in Vero or MDCK cell lines that cannot be transfected with high efficiencies. The invention disclosed herein is not limited to the use of adenovirus or retrovirus vectors to provide influenza virus but can be applied to any other negative strand RNA virus, e.g., Paramyxoviridae, Rhabdoviridae, Filoviridae, Reoviridae, Arenaviridae or Bunyaviridae.

The invention provides at least one of the following isolated (recombinant) adenovirus vectors, or a composition which includes one or more of the adenovirus vectors, which vectors include transcription cassettes. Those cassettes may include a transcription cassette comprising a PolI promoter operably linked to an influenza virus PA DNA, e.g., a full-length influenza virus PA cDNA, linked to a PolI transcription termination sequence, a transcription cassette comprising a PolI promoter operably linked to an influenza virus PB1 DNA, e.g., a full-length influenza virus PB1 cDNA, linked to a PolI transcription termination sequence, a transcription cassette comprising a PolI promoter operably linked to an influenza virus PB2 DNA, e.g., a full-length influenza virus PB2 cDNA, linked to a PolI transcription termination sequence, a transcription cassette comprising a PolI promoter operably linked to an influenza virus HA DNA, e.g., a full-length influenza virus HA cDNA, linked to a PolI transcription termination sequence, a transcription cassette comprising a PolI promoter operably linked to an influenza virus NP DNA, e.g., a full-length influenza virus NP cDNA, linked to a PolI transcription termination sequence, a transcription cassette comprising a PolI promoter operably linked to an influenza virus NA DNA, e.g., a full-length influenza virus NA cDNA, linked to a PolI transcription termination sequence, a transcription cassette comprising a PolI promoter operably linked to an influenza virus M DNA, e.g., a full-length influenza virus M cDNA, linked to a PolI transcription termination sequence, a transcription cassette comprising a PolI promoter operably linked to an influenza virus NS DNA, e.g., a full-length influenza virus NS cDNA, linked to a PolI transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, a transcription cassette comprising a PolII promoter operably linked to a DNA coding region for influenza virus NP linked to a PolII transcription termination sequence. In one embodiment, an adenovirus vector may include two transcription cassettes, each with different influenza virus sequences, e.g., NS and M sequences. In one embodiment, in place of PolI promoters and transcription termination sequences, the adenovirus vectors include RNA PolIII, T3 or T7 promoter and transcription termination sequences, or a PolII promoter-ribozyme and a ribozyme-PolII transcription termination sequence. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

The invention also provides at least one of the following isolated adenovirus vectors, or a composition which includes one or more of the adenovirus vectors, which vectors include transcription cassettes. Those cassettes may include an adenovirus vector comprising a transcription cassette comprising a PolI promoter operably linked to an influenza virus PA DNA, e.g., a full-length influenza virus PA cDNA, linked to a PolI transcription termination sequence, a transcription cassette comprising a PolI promoter operably linked to an influenza virus PB1 DNA, e.g., a full-length influenza virus PB1 cDNA, linked to a PolI transcription termination sequence, a transcription cassette comprising a PolI promoter operably linked to an influenza virus PB2 DNA, e.g., a full-length influenza virus PB2 cDNA, linked to a PolI transcription termination sequence, a transcription cassette comprising a PolI promoter operably linked to an influenza virus HA DNA, e.g., a full-length HA cDNA, linked to a PolI transcription termination sequence, a transcription cassette comprising a PolI promoter operably linked to an influenza virus NP DNA, e.g., a full-length influenza virus NP cDNA, linked to a PolI transcription termination sequence, a transcription cassette comprising a PolI promoter operably linked to an influenza virus NB and NA DNA, e.g., a full-length influenza virus NB and NA cDNA, linked to a PolI transcription termination sequence, a transcription cassette comprising a PolI promoter operably linked to an influenza virus M DNA, e.g., a full-length influenza virus M cDNA, linked to a PolI transcription termination sequence, and a transcription cassette comprising a PolI promoter operably linked to an influenza virus NS DNA, e.g., a full-length influenza virus NS cDNA, linked to a PolI transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and/or a transcription cassette comprising a PolII promoter operably linked to a DNA coding region for influenza virus NP linked to a PolII transcription termination sequence. In one embodiment, an adenovirus vector may include two transcription cassettes, each with different influenza virus sequences, e.g., NS and M sequences. In one embodiment, in place of PolI promoters and transcription termination sequences, the adenovirus vectors include RNA PolIII, SP6, T3 or T7 promoter and transcription termination sequences, or a PolII promoter-ribozyme and a ribozyme-PolII transcription termination sequence. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

The invention further includes adenovirus vectors with a transcription cassette comprising a PolI promoter and a PolI transcription termination sequence and a PolII promoter and a PolII transcription termination sequence, each operably linked to a DNA segment for influenza virus PA, e.g., a full-length influenza virus PA cDNA, a transcription cassette comprising a PolI promoter and a PolI transcription termination sequence and a PolII promoter and a PolII transcription termination sequence each operably linked to a DNA segment for influenza virus PB1, e.g., a full-length influenza virus PB1 cDNA, a transcription cassette comprising a PolI promoter and a PolI transcription termination sequence and a PolII promoter and a PolII transcription termination sequence each operably linked to a DNA segment for influenza virus PB2, e.g., a full-length influenza virus PB2 cDNA, a transcription cassette comprising a PolI promoter and a PolI transcription termination sequence and a PolII promoter and a PolII transcription termination sequence each operably linked to a DNA segment for influenza virus NP, e.g., a full-length influenza virus NP cDNA, a transcription cassette comprising a PolI promoter and a PolI transcription termination sequence and a PolII promoter and a PolII transcription termination sequence each operably linked to a DNA segment for influenza virus HA, e.g., a full-length influenza virus HA cDNA, a transcription cassette comprising a PolI promoter and a PolI transcription termination sequence and a PolII promoter and a PolII transcription termination sequence each operably linked to a DNA segment for influenza virus NA, e.g., a full-length influenza virus NA cDNA, a transcription cassette comprising a PolI promoter and a PolI transcription termination sequence and a PolII promoter and a PolII transcription termination sequence each operably linked to a DNA segment for influenza virus NS, e.g., a full-length influenza virus NS cDNA, and a transcription cassette comprising a PolI promoter and a PolI transcription termination sequence and a PolII promoter and a PolII transcription termination sequence each operably linked to a DNA segment for influenza virus M, e.g., a full-length influenza virus M cDNA. In one embodiment, an adenovirus vector may include two transcription cassettes, each with different influenza virus sequences, e.g., NS and M sequences. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

The invention further includes adenovirus vectors with a transcription cassette comprising a PolI promoter and a PolI transcription termination sequence and a PolII promoter and a PolII transcription termination sequence, each operably linked to a DNA segment for influenza virus PA, e.g., a full-length influenza virus PA cDNA, a transcription cassette comprising a PolI promoter and a PolI transcription termination sequence and a PolII promoter and a PolII transcription termination sequence each operably linked to a DNA segment for influenza virus PB1, e.g., a full-length influenza virus PB1 cDNA, a transcription cassette comprising a PolI promoter and a PolI transcription termination sequence and a PolII promoter and a PolII transcription termination sequence each operably linked to a DNA segment for influenza virus PB2, e.g., a full-length influenza virus PB2 cDNA, a transcription cassette comprising a PolI promoter and a PolI transcription termination sequence and a PolII promoter and a PolII transcription termination sequence each operably linked to a DNA segment for influenza virus NP, e.g., a full-length influenza virus NP cDNA, a transcription cassette comprising a PolI promoter and a PolI transcription termination sequence and a PolII promoter and a PolII transcription termination sequence each operably linked to a DNA segment for influenza virus HA, e.g., a full-length influenza virus HA cDNA, a transcription cassette comprising a PolI promoter and a PolI transcription termination sequence and a PolII promoter and a PolII transcription termination sequence each operably linked to a DNA segment for influenza virus NA and NB, e.g., a full-length influenza virus NA and NB cDNA, a transcription cassette comprising a PolI promoter and a PolI transcription termination sequence and a PolII promoter and a PolII transcription termination sequence each operably linked to a DNA segment for influenza virus NS, e.g., a full-length influenza virus NS cDNA, and a transcription cassette comprising a PolI promoter and a PolI transcription termination sequence and a PolII promoter and a PolII transcription termination sequence each operably linked to a DNA segment for influenza virus M, e.g., a full-length influenza virus M cDNA. In one embodiment, an adenovirus vector may include two transcription cassettes, each with different influenza virus sequences, e.g., NS and M sequences. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

Further provided are adenovirus vectors which include a transcription cassette comprising a PolI promoter operably linked to an influenza virus PA DNA, e.g., a full-length influenza virus PA cDNA, linked to a PolI transcription termination sequence, a transcription cassette comprising a PolI promoter operably linked to an influenza virus PB1 DNA, e.g., a full-length influenza virus PB1 cDNA, linked to a PolI transcription termination sequence, a transcription cassette comprising a PolI promoter operably linked to an influenza virus PB2 DNA, a full-length influenza virus PB2 cDNA, linked to a PolI transcription termination sequence, a transcription cassette comprising a PolI promoter operably linked to an influenza virus HEF DNA, e.g., a full-length influenza virus HEF cDNA, linked to a PolI transcription termination sequence, a transcription cassette comprising a PolI promoter operably linked to an influenza virus NP DNA, e.g., a full-length influenza virus NP cDNA, linked to a PolI transcription termination sequence, a PolI promoter operably linked to an influenza virus M DNA, e.g., a full-length influenza virus M cDNA, linked to a PolI transcription termination sequence, or a transcription cassette comprising a promoter operably linked to an influenza virus NS DNA, e.g., a full-length influenza virus NS cDNA, linked to a PolI transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and/or a transcription cassette comprising a PolII promoter operably linked to a DNA coding region for influenza virus NP linked to a PolII transcription termination sequence. In one embodiment, an adenovirus vector may include two transcription cassettes, each with different influenza virus sequences, e.g., NS and M sequences. In one embodiment, in place of PolI promoters and transcription termination sequences, the adenovirus vectors include RNA PolIII, T3 or T7 promoter and transcription termination sequences, or a PolII promoter-ribozyme and a ribozyme-PolII transcription termination sequence. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

In one embodiment, the invention provides isolated adenovirus vectors which include a transcription cassette comprising a PolI promoter and a PolI transcription termination sequence and a PolII promoter and a PolII transcription termination sequence, each operably linked to an influenza virus PA DNA, e.g., a full-length influenza virus PA cDNA, a transcription cassette comprising a PolI promoter and a PolI transcription termination sequence and a PolII promoter and a PolII transcription termination sequence, each operably linked to an influenza virus PB1 DNA, e.g., a full-length influenza virus PB1 cDNA, a transcription cassette comprising a PolI promoter and a PolI transcription termination sequence and a PolII promoter and a PolII transcription termination sequence, each operably linked to an influenza virus PB2 DNA, e.g., a full-length influenza virus PB2 cDNA, a transcription cassette comprising a PolI promoter and a PolI transcription termination sequence and a PolII promoter and a PolII transcription termination sequence, each operably linked to an influenza virus HEF DNA, e.g., a full-length influenza virus HEF cDNA, a transcription cassette comprising a PolI promoter and a PolI transcription termination sequence and a PolII promoter and a PolII transcription termination sequence, each operably linked to an influenza virus NP DNA, e.g., a full-length influenza virus NP cDNA, a transcription cassette comprising a PolI promoter and a PolI transcription termination sequence and a PolII promoter and a PolII transcription termination sequence, each operably linked to an influenza virus M DNA, e.g., a full-length influenza virus M cDNA, a transcription cassette comprising a PolI promoter and a PolI transcription termination sequence and a PolII promoter and a PolII transcription termination sequence, each operably linked to an influenza virus NS DNA, e.g., a full-length influenza virus NS cDNA. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

In one embodiment, the invention provides isolated adenovirus vectors, or a composition which includes one or more isolated adenovirus vectors, having a plurality of transcription cassettes: a transcription cassette comprising a PolI promoter operably linked to an influenza virus PA DNA, e.g., a full-length influenza virus PA cDNA, linked to a PolI transcription termination sequence, a transcription cassette comprising a PolI promoter operably linked to an influenza virus PB1 DNA, e.g., a full-length influenza virus PB1 cDNA, linked to a PolI transcription termination sequence, a transcription cassette comprising a PolI promoter operably linked to an influenza virus PB2 DNA, e.g., a full-length influenza virus PB2 cDNA, linked to a PolI transcription termination sequence, a transcription cassette comprising a PolI promoter operably linked to an influenza virus HA DNA, e.g., a full-length influenza virus HA cDNA, linked to a PolI transcription termination sequence, a transcription cassette comprising a PolI promoter operably linked to an influenza virus NP DNA, e.g., a full-length influenza virus NP cDNA, linked to a PolI transcription termination sequence, a transcription cassette comprising a PolI promoter operably linked to an influenza virus M DNA, e.g., a full-length influenza virus M cDNA, linked to a PolI transcription termination sequence, a transcription cassette comprising a PolI promoter operably linked to an influenza virus NS DNA, e.g., a full-length influenza virus NS cDNA, linked to a PolI transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, a transcription cassette comprising a PolII promoter operably linked to a DNA coding region for influenza virus NP linked to a PolII transcription termination sequence, and optionally one or more of the following: a transcription cassette comprising a PolII promoter and a PolII transcription termination operably linked to a DNA segment for influenza virus HA, e.g., a full-length influenza virus HA cDNA, a transcription cassette comprising a PolII promoter and a PolII transcription termination sequence operably linked to a DNA segment for influenza virus M, e.g., a full-length influenza virus M cDNA, and/or a transcription cassette comprising a PolII promoter sequence and a PolII transcription termination sequence operably linked to a DNA segment for influenza virus NS, e.g., a full-length influenza virus NS cDNA. Thus, in this embodiment, the set of adenovirus vectors or composition with a set of adenovirus vectors does not include NA sequences, i.e., it is a NAvirus. That is, the set of vectors or host cell infected with the set of vectors does not include sequences corresponding to NA coding or noncoding sequences for vRNA production or for vRNA production and mRNA production.

The invention also provides isolated adenovirus vectors having a transcription cassette comprising a PolII promoter linked to a ribozyme sequence linked to an influenza virus PA DNA, e.g., a full-length influenza virus PA cDNA, linked to a ribozyme sequence linked to a PolII transcription termination sequence, a transcription cassette comprising a PolII promoter linked to a ribozyme sequence linked to an influenza virus PB1 DNA, e.g., a full-length influenza virus PB1 cDNA, linked to a ribozyme sequence linked to a PolII transcription termination sequence, a transcription cassette comprising a PolII promoter linked to a ribozyme sequence linked to an influenza virus PB2 DNA, e.g., a full-length influenza virus PB2 cDNA, linked to a ribozyme sequence linked to a PolII transcription termination sequence, a transcription cassette comprising a PolII promoter linked to a ribozyme sequence linked to an influenza virus HA DNA, e.g., a full-length influenza virus HA cDNA, linked to a ribozyme sequence linked to a PolII transcription termination sequence, a transcription cassette comprising a PolII promoter linked to a ribozyme sequence linked to an influenza virus NP DNA, e.g., a full-length influenza virus NP cDNA, linked to a ribozyme sequence linked to a PolII transcription termination sequence, a transcription cassette comprising a PolII promoter linked to a ribozyme sequence linked to an influenza virus M DNA, e.g., a full-length influenza virus M cDNA, linked to a ribozyme sequence linked to a PolII transcription termination sequence, a transcription cassette comprising a PolII promoter linked to a ribozyme sequence linked to an influenza virus NS DNA, e.g., a full-length influenza virus NS cDNA, linked to a ribozyme sequence linked to a PolII transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, a transcription cassette comprising a PolII promoter operably linked to a DNA coding region for influenza virus NP linked to a PolII transcription termination sequence, and optionally one or more of the following: a transcription cassette comprising a PolII promoter and a PolII transcription termination operably linked to a DNA segment for influenza virus HA, e.g., a full-length influenza virus HA cDNA, a transcription cassette comprising a PolII promoter and a PolII transcription termination sequence operably linked to a DNA segment for influenza virus M, e.g., a full-length influenza virus M cDNA, and/or a transcription cassette comprising a PolII promoter sequence and a PolII transcription termination sequence operably linked to a DNA segment for influenza virus NS, e.g., a full-length influenza virus NS cDNA. In this embodiment, the set of adenovirus vectors or composition with a set of adenovirus vectors does not include NA coding sequences. That is, the set of vectors or host cell infected with the set of vectors does not include sequences corresponding to NA coding or noncoding sequences for vRNA production or for vRNA production and mRNA production.

The invention provides at least one of the following isolated (recombinant) retrovirus vectors, or a composition which includes one or more of the retrovirus vectors, which vectors include transcription cassettes. Those cassettes may include a transcription cassette comprising a PolI promoter operably linked to an influenza virus PA DNA, e.g., a full-length influenza virus PA cDNA, linked to a PolI transcription termination sequence, a transcription cassette comprising a PolI promoter operably linked to an influenza virus PB1 DNA, e.g., a full-length influenza virus PB1 cDNA, linked to a PolI transcription termination sequence, a transcription cassette comprising a PolI promoter operably linked to an influenza virus PB2 DNA, e.g., a full-length influenza virus PB2 cDNA, linked to a PolI transcription termination sequence, a transcription cassette comprising a PolI promoter operably linked to an influenza virus HA DNA, e.g., a full-length influenza virus HA cDNA, linked to a PolI transcription termination sequence, a transcription cassette comprising a PolI promoter operably linked to an influenza virus NP DNA, e.g., a full-length influenza virus NP cDNA, linked to a PolI transcription termination sequence, a transcription cassette comprising a PolI promoter operably linked to an influenza virus NA DNA, e.g., a full-length influenza virus NA cDNA, linked to a PolI transcription termination sequence, a transcription cassette comprising a PolI promoter operably linked to an influenza virus M DNA, e.g., a full-length influenza virus M cDNA, linked to a PolI transcription termination sequence, a transcription cassette comprising a PolI promoter operably linked to an influenza virus NS DNA, e.g., a full-length influenza virus NS cDNA, linked to a PolI transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, a transcription cassette comprising a PolII promoter operably linked to a DNA coding region for influenza virus NP linked to a PolII transcription termination sequence. In one embodiment, a retrovirus vector may include two transcription cassettes, each with different influenza virus sequences, e.g., NS and M sequences. In one embodiment, in place of PolI promoters and transcription termination sequences, the retrovirus vectors include RNA PolIII, T3 or T7 promoter and transcription termination sequences, or a PolII promoter-ribozyme and a ribozyme-PolII transcription termination sequence. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

The invention also provides at least one of the following isolated retrovirus vectors, or a composition which includes one or more of the retrovirus vectors, which vectors include transcription cassettes. Those cassettes may include a retrovirus vector comprising a transcription cassette comprising a PolI promoter operably linked to an influenza virus PA DNA, e.g., a full-length influenza virus PA cDNA, linked to a PolI transcription termination sequence, a transcription cassette comprising a PolI promoter operably linked to an influenza virus PB1 DNA, e.g., a full-length influenza virus PB1 cDNA, linked to a PolI transcription termination sequence, a transcription cassette comprising a PolI promoter operably linked to an influenza virus PB2 DNA, e.g., a full-length influenza virus PB2 cDNA, linked to a PolI transcription termination sequence, a transcription cassette comprising a PolI promoter operably linked to an influenza virus HA DNA, e.g., a full-length HA cDNA, linked to a PolI transcription termination sequence, a transcription cassette comprising a PolI promoter operably linked to an influenza virus NP DNA, e.g., a full-length influenza virus NP cDNA, linked to a PolI transcription termination sequence, a transcription cassette comprising a PolI promoter operably linked to an influenza virus NB and NA DNA, e.g., a full-length influenza virus NB and NA cDNA, linked to a PolI transcription termination sequence, a transcription cassette comprising a PolI promoter operably linked to an influenza virus M DNA, e.g., a full-length influenza virus M cDNA, linked to a PolI transcription termination sequence, and a transcription cassette comprising a PolI promoter operably linked to an influenza virus NS DNA, e.g., a full-length influenza virus NS cDNA, linked to a PolI transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and/or a transcription cassette comprising a PolII promoter operably linked to a DNA coding region for influenza virus NP linked to a PolII transcription termination sequence. In one embodiment, a retrovirus vector may include two transcription cassettes, each with different influenza virus sequences, e.g., NS and M sequences. In one embodiment, in place of PolI promoters and transcription termination sequences, the retrovirus vectors include RNA PolIII, T3 or T7 promoter and transcription termination sequences, or a PolII promoter-ribozyme and a ribozyme-PolII transcription termination sequence. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

The invention further includes retrovirus vectors with a transcription cassette comprising a PolI promoter and a PolI transcription termination sequence and a PolII promoter and a PolII transcription termination sequence, each operably linked to a DNA segment for influenza virus PA, e.g., a full-length influenza virus PA cDNA, a transcription cassette comprising a PolI promoter and a PolI transcription termination sequence and a PolII promoter and a PolII transcription termination sequence each operably linked to a DNA segment for influenza virus PB1, e.g., a full-length influenza virus PB1 cDNA, a transcription cassette comprising a PolI promoter and a PolI transcription termination sequence and a PolI promoter and a PolII transcription termination sequence each operably linked to a DNA segment for influenza virus PB2, e.g., a full-length influenza virus PB2 cDNA, a transcription cassette comprising a PolI promoter and a PolI transcription termination sequence and a PolII promoter and a PolII transcription termination sequence each operably linked to a DNA segment for influenza virus NP, e.g., a full-length influenza virus NP cDNA, a transcription cassette comprising a PolI promoter and a PolI transcription termination sequence and a PolII promoter and a PolII transcription termination sequence each operably linked to a DNA segment for influenza virus HA, e.g., a full-length influenza virus HA cDNA, a transcription cassette comprising a PolI promoter and a PolI transcription termination sequence and a PolII promoter and a PolII transcription termination sequence each operably linked to a DNA segment for influenza virus NA, e.g., a full-length influenza virus NA cDNA, a transcription cassette comprising a PolI promoter and a PolI transcription termination sequence and a PolII promoter and a PolII transcription termination sequence each operably linked to a DNA segment for influenza virus NS, e.g., a full-length influenza virus NS cDNA, and a transcription cassette comprising a PolI promoter and a PolI transcription termination sequence and a PolII promoter and a PolII transcription termination sequence each operably linked to a DNA segment for influenza virus M, e.g., a full-length influenza virus M cDNA. In one embodiment, an adenovirus vector may include two transcription cassettes, each with different influenza virus sequences, e.g., NS and M sequences. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

The invention further includes retrovirus vectors with a transcription cassette comprising a PolI promoter and a PolI transcription termination sequence and a PolII promoter and a PolII transcription termination sequence, each operably linked to a DNA segment for influenza virus PA, e.g., a full-length influenza virus PA cDNA, a transcription cassette comprising a PolI promoter and a PolI transcription termination sequence and a PolII promoter and a PolII transcription termination sequence each operably linked to a DNA segment for influenza virus PB1, e.g., a full-length influenza virus PB1 cDNA, a transcription cassette comprising a PolI promoter and a PolI transcription termination sequence and a PolI promoter and a PolII transcription termination sequence each operably linked to a DNA segment for influenza virus PB2, e.g., a full-length influenza virus PB2 cDNA, a transcription cassette comprising a PolI promoter and a PolI transcription termination sequence and a PolII promoter and a PolII transcription termination sequence each operably linked to a DNA segment for influenza virus NP, e.g., a full-length influenza virus NP cDNA, a transcription cassette comprising a PolI promoter and a PolI transcription termination sequence and a PolII promoter and a PolII transcription termination sequence each operably linked to a DNA segment for influenza virus HA, e.g., a full-length influenza virus HA cDNA, a transcription cassette comprising a PolI promoter and a PolI transcription termination sequence and a PolII promoter and a PolII transcription termination sequence each operably linked to a DNA segment for influenza virus NA and NB, e.g., a full-length influenza virus NA and NB cDNA, a transcription cassette comprising a PolI promoter and a PolI transcription termination sequence and a PolII promoter and a PolII transcription termination sequence each operably linked to a DNA segment for influenza virus NS, e.g., a full-length influenza virus NS cDNA, and a transcription cassette comprising a PolI promoter and a PolI transcription termination sequence and a PolII promoter and a PolII transcription termination sequence each operably linked to a DNA segment for influenza virus M, e.g., a full-length influenza virus M cDNA. In one embodiment, an adenovirus vector may include two transcription cassettes, each with different influenza virus sequences, e.g., NS and M sequences. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

Further provided are retrovirus vectors which include a transcription cassette comprising a PolI promoter operably linked to an influenza virus PA DNA, e.g., a full-length influenza virus PA cDNA, linked to a PolI transcription termination sequence, a transcription cassette comprising a PolI promoter operably linked to an influenza virus PB1 DNA, e.g., a full-length influenza virus PB1 cDNA, linked to a PolI transcription termination sequence, a transcription cassette comprising a PolI promoter operably linked to an influenza virus PB2 DNA, a full-length influenza virus PB2 cDNA, linked to a PolI transcription termination sequence, a transcription cassette comprising a PolI promoter operably linked to an influenza virus HEF DNA, e.g., a full-length influenza virus HEF cDNA, linked to a PolI transcription termination sequence, a transcription cassette comprising a PolI promoter operably linked to an influenza virus NP DNA, e.g., a full-length influenza virus NP cDNA, linked to a PolI transcription termination sequence, a PolI promoter operably linked to an influenza virus M DNA, e.g., a full-length influenza virus M cDNA, linked to a PolI transcription termination sequence, or a transcription cassette comprising a promoter operably linked to an influenza virus NS DNA, e.g., a full-length influenza virus NS cDNA, linked to a PolI transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and/or a transcription cassette comprising a PolII promoter operably linked to a DNA coding region for influenza virus NP linked to a PolII transcription termination sequence. In one embodiment, a retrovirus vector may include two transcription cassettes, each with different influenza virus sequences, e.g., NS and M sequences. In one embodiment, in place of PolI promoters and transcription termination sequences, the retrovirus vectors include RNA PolIII, T3 or T7 promoter and transcription termination sequences, or a PolII promoter-ribozyme and a ribozyme-PolII transcription termination sequence. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

In one embodiment, the invention provides isolated retrovirus vectors which include a transcription cassette comprising a PolI promoter and a PolI transcription termination sequence and a PolII promoter and a PolII transcription termination sequence, each operably linked to an influenza virus PA DNA, e.g., a full-length influenza virus PA cDNA, a transcription cassette comprising a PolI promoter and a PolI transcription termination sequence and a PolII promoter and a PolII transcription termination sequence, each operably linked to an influenza virus PB1 DNA, e.g., a full-length influenza virus PB1 cDNA, a transcription cassette comprising a PolI promoter and a PolI transcription termination sequence and a PolII promoter and a PolII transcription termination sequence, each operably linked to an influenza virus PB2 DNA, e.g., a full-length influenza virus PB2 cDNA, a transcription cassette comprising a PolI promoter and a PolI transcription termination sequence and a PolII promoter and a PolII transcription termination sequence, each operably linked to an influenza virus HEF DNA, e.g., a full-length influenza virus HEF cDNA, a transcription cassette comprising a PolI promoter and a PolI transcription termination sequence and a PolII promoter and a PolII transcription termination sequence, each operably linked to an influenza virus NP DNA, e.g., a full-length influenza virus NP cDNA, a transcription cassette comprising a PolI promoter and a PolI transcription termination sequence and a PolII promoter and a PolII transcription termination sequence, each operably linked to an influenza virus M DNA, e.g., a full-length influenza virus M cDNA, a transcription cassette comprising a PolI promoter and a PolI transcription termination sequence and a PolII promoter and a PolII transcription termination sequence, each operably linked to an influenza virus NS DNA, e.g., a full-length influenza virus NS cDNA. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

In one embodiment, the invention provides isolated retrovirus vectors, or a composition which includes one or more isolated retrovirus vectors, having a plurality of transcription cassettes: a transcription cassette comprising a PolI promoter operably linked to an influenza virus PA DNA, e.g., a full-length influenza virus PA cDNA, linked to a PolI transcription termination sequence, a transcription cassette comprising a PolI promoter operably linked to an influenza virus PB1 DNA, e.g., a full-length influenza virus PB1 cDNA, linked to a PolI transcription termination sequence, a transcription cassette comprising a PolI promoter operably linked to an influenza virus PB2 DNA, e.g., a full-length influenza virus PB2 cDNA, linked to a PolI transcription termination sequence, a transcription cassette comprising a PolI promoter operably linked to an influenza virus HA DNA, e.g., a full-length influenza virus HA cDNA, linked to a PolI transcription termination sequence, a transcription cassette comprising a PolI promoter operably linked to an influenza virus NP DNA, e.g., a full-length influenza virus NP cDNA, linked to a PolI transcription termination sequence, a transcription cassette comprising a PolI promoter operably linked to an influenza virus M DNA, e.g., a full-length influenza virus M cDNA, linked to a PolI transcription termination sequence, a transcription cassette comprising a PolI promoter operably linked to an influenza virus NS DNA, e.g., a full-length influenza virus NS cDNA, linked to a PolI transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, a transcription cassette comprising a PolII promoter operably linked to a DNA coding region for influenza virus NP linked to a PolII transcription termination sequence, and optionally one or more of the following: a transcription cassette comprising a PolII promoter and a PolII transcription termination operably linked to a DNA segment for influenza virus HA, e.g., a full-length influenza virus HA cDNA, a transcription cassette comprising a PolII promoter and a PolII transcription termination sequence operably linked to a DNA segment for influenza virus M, e.g., a full-length influenza virus M cDNA, and/or a transcription cassette comprising a PolII promoter sequence and a PolII transcription termination sequence operably linked to a DNA segment for influenza virus NS, e.g., a full-length influenza virus NS cDNA. Thus, in this embodiment, the set of retrovirus vectors or composition with a set of retrovirus vectors does not include NA sequences, i.e., it is a NA virus. That is, the set of vectors or host cell infected with the set of vectors does not include sequences corresponding to NA coding or noncoding sequences for vRNA production or for vRNA production and mRNA production.

The invention also provides isolated retrovirus vectors having a transcription cassette comprising a PolII promoter linked to a ribozyme sequence linked to an influenza virus PA DNA, e.g., a full-length influenza virus PA cDNA, linked to a ribozyme sequence linked to a PolII transcription termination sequence, a transcription cassette comprising a PolII promoter linked to a ribozyme sequence linked to an influenza virus PB1 DNA, e.g., a full-length influenza virus PB1 cDNA, linked to a ribozyme sequence linked to a PolII transcription termination sequence, a transcription cassette comprising a PolII promoter linked to a ribozyme sequence linked to an influenza virus PB2 DNA, e.g., a full-length influenza virus PB2 cDNA, linked to a ribozyme sequence linked to a PolII transcription termination sequence, a transcription cassette comprising a PolII promoter linked to a ribozyme sequence linked to an influenza virus HA DNA, e.g., a full-length influenza virus HA cDNA, linked to a ribozyme sequence linked to a PolII transcription termination sequence, a transcription cassette comprising a PolII promoter linked to a ribozyme sequence linked to an influenza virus NP DNA, e.g., a full-length influenza virus NP cDNA, linked to a ribozyme sequence linked to a PolII transcription termination sequence, a transcription cassette comprising a PolII promoter linked to a ribozyme sequence linked to an influenza virus M DNA, e.g., a full-length influenza virus M cDNA, linked to a ribozyme sequence linked to a PolII transcription termination sequence, a transcription cassette comprising a PolII promoter linked to a ribozyme sequence linked to an influenza virus NS DNA, e.g., a full-length influenza virus NS cDNA, linked to a ribozyme sequence linked to a PolII transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, a transcription cassette comprising a PolII promoter operably linked to a DNA coding region for influenza virus NP linked to a PolII transcription termination sequence, and optionally one or more of the following: a transcription cassette comprising a PolII promoter and a PolII transcription termination operably linked to a DNA segment for influenza virus HA, e.g., a full-length influenza virus HA cDNA, a transcription cassette comprising a PolII promoter and a PolII transcription termination sequence operably linked to a DNA segment for influenza virus M, e.g., a full-length influenza virus M cDNA, and/or a transcription cassette comprising a PolII promoter sequence and a PolII transcription termination sequence operably linked to a DNA segment for influenza virus NS, e.g., a full-length influenza virus NS cDNA. In this embodiment, the set of retrovirus vectors or composition with a set of retrovirus vectors does not include NA coding sequences. That is, the set of vectors or host cell infected with the set of vectors does not include sequences corresponding to NA coding or noncoding sequences for vRNA production or for vRNA production and mRNA production.

Exemplary Compositions and Host Cells of the Invention

The invention provides a composition or host cell comprising a plurality, e.g., at least six (for influenza C virus) and seven (for influenza A and B viruses), adenovirus or retrovirus vectors which vectors include transcription cassettes for vRNA production, i.e., a transcription cassette comprising a PolI promoter operably linked to an influenza virus PA DNA, e.g., a full-length influenza virus PA cDNA, linked to a PolI transcription termination sequence, a transcription cassette comprising a PolI promoter operably linked to an influenza virus PB1 DNA, e.g., a full-length influenza virus PB1 cDNA, linked to a PolI transcription termination sequence, a transcription cassette comprising a PolI promoter operably linked to an influenza virus PB2 DNA, e.g., a full-length influenza virus PB2 cDNA, linked to a PolI transcription termination sequence, a transcription cassette comprising a PolI promoter operably linked to an influenza virus HA DNA, e.g., a full-length influenza virus HA cDNA, linked to a PolI transcription termination sequence, a transcription cassette comprising a PolI promoter operably linked to an influenza virus NP cDNA, e.g., a full-length influenza virus NP DNA, linked to a PolI transcription termination sequence, a transcription cassette comprising a PolI promoter operably linked to an influenza virus NA DNA, e.g., a full-length influenza virus NA cDNA, linked to a PolI transcription termination sequence, a transcription cassette comprising a PolI promoter operably linked to an influenza virus M DNA, e.g., a full-length influenza virus M cDNA, linked to a PolI transcription termination sequence, and/or a transcription cassette comprising a PolI promoter operably linked to an influenza virus NS DNA, e.g., a full-length influenza virus NS cDNA, linked to a PolI transcription termination sequence; and transcription cassettes for mRNA production, i.e., a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and/or a transcription cassette comprising a PolII promoter operably linked to a DNA coding region for influenza virus NP linked to a PolII transcription termination sequence, wherein the composition or host cell may have any combination of the vectors. In one embodiment, each PolI promoter is the same. In one embodiment, each PolII promoter is the same. In one embodiment, each PolI transcription terminator sequence is the same. In one embodiment, each PolII transcription terminator sequence is the same.

The invention further provides a composition or host cell comprising a plurality of adenovirus vectors with transcription cassettes for vRNA production selected from a transcription cassette comprising a PolI promoter operably linked to an influenza virus PA DNA, e.g., a full-length influenza virus PA cDNA, linked to a PolI transcription termination sequence, a transcription cassette comprising a PolI promoter operably linked to an influenza virus PB1 DNA, e.g., a full-length influenza virus PB1 cDNA, linked to a PolI transcription termination sequence, a transcription cassette comprising a PolI promoter operably linked to an influenza virus PB2 DNA, e.g., a full-length influenza virus PB2 cDNA, linked to a PolI transcription termination sequence, a transcription cassette comprising a PolI promoter operably linked to an influenza virus HA DNA, e.g., a full-length influenza virus HA cDNA, linked to a PolI transcription termination sequence, a transcription cassette comprising a PolI promoter operably linked to an influenza virus NP DNA, e.g., a full-length influenza virus NP cDNA, linked to a PolI transcription termination sequence, a transcription cassette comprising a PolI promoter operably linked to an influenza virus M DNA, e.g., a full-length influenza virus M cDNA, linked to a PolI transcription termination sequence, and/or a transcription cassette comprising a PolI promoter operably linked to an influenza virus NS DNA, e.g., a full-length influenza virus NS cDNA, linked to a PolI transcription termination sequence, and optionally includes a transcription cassette comprising a PolI promoter operably linked to an influenza virus NA DNA, e.g., a full-length influenza virus NA cDNA, linked to a PolI transcription termination sequence; and includes one or more adenovirus vectors with transcription cassettes for mRNA production selected from a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and/or a transcription cassette comprising a PolII promoter operably linked to a DNA coding region for influenza virus NP linked to a PolII transcription termination sequence, wherein the composition or host cell may have any combination of the vectors. In one embodiment, each PolI promoter is the same. In one embodiment, each PolII promoter is the same. In one embodiment, each PolI transcription terminator sequence is the same. In one embodiment, each PolII transcription terminator sequence is the same.

The invention provides a composition or host cell comprising a plurality of vectors that may include a transcription cassette comprising a PolI promoter operably linked to an influenza virus PA DNA, e.g., a full-length influenza virus PA cDNA, linked to a PolI transcription termination sequence, a transcription cassette comprising a PolI promoter operably linked to an influenza virus PB1 DNA, e.g., a full-length influenza virus PB1 cDNA, linked to a PolI transcription termination sequence, a transcription cassette comprising a PolI promoter operably linked to an influenza virus PB2 DNA, e.g., a full-length influenza virus PB2 cDNA, linked to a PolI transcription termination sequence, a transcription cassette comprising a PolI promoter operably linked to an influenza virus HA DNA, e.g., a full-length influenza virus HA cDNA, linked to a PolI transcription termination sequence, a transcription cassette comprising a PolI promoter operably linked to an influenza virus NP DNA, e.g., a full-length influenza virus NP cDNA, linked to a PolI transcription termination sequence, a transcription cassette comprising a PolI promoter operably linked to an influenza virus NA DNA, e.g., a full-length influenza virus NA cDNA, linked to a PolI transcription termination sequence, a transcription cassette comprising a PolI promoter operably linked to an influenza virus M DNA, e.g., a full-length influenza virus M cDNA, linked to a PolI transcription termination sequence, a transcription cassette comprising a PolI promoter operably linked to an influenza virus NS DNA, e.g., a full-length influenza virus NS cDNA, linked to a PolI transcription termination sequence, a transcription cassette comprising a PolI promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, a transcription cassette comprising a PolII promoter operably linked to a DNA coding region for influenza virus NP linked to a PolII transcription termination sequence, wherein the composition or host cell may have any combination of the vectors. In one embodiment, an adenovirus vector may include two transcription cassettes, each with different influenza virus sequences, e.g., NS and M sequences. In one embodiment, in place of PolI promoters and transcription termination sequences, the adenovirus vectors include RNA PolIII, T3 or T7 promoter and transcription termination sequences, or a PolII promoter-ribozyme and a ribozyme-PolII transcription termination sequence. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

The invention also provides a composition or host cell comprising a plurality of vectors that may include an adenovirus vector comprising a transcription cassette comprising a PolI promoter operably linked to an influenza virus PA DNA, e.g., a full-length influenza virus PA cDNA, linked to a PolI transcription termination sequence, a transcription cassette comprising a PolI promoter operably linked to an influenza virus PB1 DNA, e.g., a full-length influenza virus PB1 cDNA, linked to a PolI transcription termination sequence, a transcription cassette comprising a PolI promoter operably linked to an influenza virus PB2 DNA, e.g., a full-length influenza virus PB2 cDNA, linked to a PolI transcription termination sequence, a transcription cassette comprising a PolI promoter operably linked to an influenza virus HA DNA, e.g., a full-length HA cDNA, linked to a PolI transcription termination sequence, a transcription cassette comprising a PolI promoter operably linked to an influenza virus NP DNA, e.g., a full-length influenza virus NP cDNA, linked to a PolI transcription termination sequence, a transcription cassette comprising a PolI promoter operably linked to an influenza virus NB and NA DNA, e.g., a full-length influenza virus NB and NA cDNA, linked to a PolI transcription termination sequence, a transcription cassette comprising a PolI promoter operably linked to an influenza virus M DNA, e.g., a full-length influenza virus M cDNA, linked to a PolI transcription termination sequence, and/or a transcription cassette comprising a PolI promoter operably linked to an influenza virus NS DNA, e.g., a full-length influenza virus NS cDNA, linked to a PolI transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and/or a transcription cassette comprising a PolII promoter operably linked to a DNA coding region for influenza virus NP linked to a PolII transcription termination sequence, wherein the composition or host cell may have any combination of the vectors. In one embodiment, an adenovirus vector may include two transcription cassettes, each with different influenza virus sequences, e.g., NS and M sequences. In one embodiment, in place of PolI promoters and transcription termination sequences, the adenovirus vectors include RNA PolIII, T3 or T7 promoter and transcription termination sequences, or a PolII promoter-ribozyme and a ribozyme-PolII transcription termination sequence. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

The invention further includes a composition or host cell comprising a plurality of adenovirus vectors that may include vectors with a transcription cassette comprising a PolI promoter and a PolI transcription termination sequence and a PolI promoter and a PolII transcription termination sequence, each operably linked to a DNA segment for influenza virus PA, e.g., a full-length influenza virus PA cDNA, a transcription cassette comprising a PolI promoter and a PolI transcription termination sequence and a PolII promoter and a PolII transcription termination sequence each operably linked to a DNA segment for influenza virus PB1, e.g., a full-length influenza virus PB1 cDNA, a transcription cassette comprising a PolI promoter and a PolI transcription termination sequence and a PolI promoter and a PolII transcription termination sequence each operably linked to a DNA segment for influenza virus PB2, e.g., a full-length influenza virus PB2 cDNA, a transcription cassette comprising a PolI promoter and a PolI transcription termination sequence and a PolII promoter and a PolII transcription termination sequence each operably linked to a DNA segment for influenza virus NP, e.g., a full-length influenza virus NP cDNA, a transcription cassette comprising a PolI promoter and a PolI transcription termination sequence and a PolII promoter and a PolII transcription termination sequence each operably linked to a DNA segment for influenza virus HA, e.g., a full-length influenza virus HA cDNA, a transcription cassette comprising a PolI promoter and a PolI transcription termination sequence and a PolII promoter and a PolII transcription termination sequence each operably linked to a DNA segment for influenza virus NA, e.g., a full-length influenza virus NA cDNA, a transcription cassette comprising a PolI promoter and a PolI transcription termination sequence and a PolII promoter and a PolII transcription termination sequence each operably linked to a DNA segment for influenza virus NS, e.g., a full-length influenza virus NS cDNA, and/or a transcription cassette comprising a PolI promoter and a PolI transcription termination sequence and a PolII promoter and a PolII transcription termination sequence each operably linked to a DNA segment for influenza virus M, e.g., a full-length influenza virus M cDNA, wherein the composition or host cell may have any combination of the vectors. In one embodiment, an adenovirus vector may include two transcription cassettes, each with different influenza virus sequences, e.g., NS and M sequences. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

The invention further includes a composition or host cell comprising a plurality of adenovirus vectors that may include vectors with a transcription cassette comprising a PolI promoter and a PolI transcription termination sequence and a PolII promoter and a PolII transcription termination sequence, each operably linked to a DNA segment for influenza virus PA, e.g., a full-length influenza virus PA cDNA, a transcription cassette comprising a PolI promoter and a PolI transcription termination sequence and a PolII promoter and a PolII transcription termination sequence each operably linked to a DNA segment for influenza virus PB1, e.g., a full-length influenza virus PB1 cDNA, a transcription cassette comprising a PolI promoter and a PolI transcription termination sequence and a PolII promoter and a PolII transcription termination sequence each operably linked to a DNA segment for influenza virus PB2, e.g., a full-length influenza virus PB2 cDNA, a transcription cassette comprising a PolI promoter and a PolI transcription termination sequence and a PolII promoter and a PolII transcription termination sequence each operably linked to a DNA segment for influenza virus NP, e.g., a full-length influenza virus NP cDNA, a transcription cassette comprising a PolI promoter and a PolI transcription termination sequence and a PolII promoter and a PolII transcription termination sequence each operably linked to a DNA segment for influenza virus HA, e.g., a full-length influenza virus HA cDNA, a transcription cassette comprising a PolI promoter and a PolI transcription termination sequence and a PolII promoter and a PolII transcription termination sequence each operably linked to a DNA segment for influenza virus NA and NB, e.g., a full-length influenza virus NA and NB cDNA, a transcription cassette comprising a PolI promoter and a PolI transcription termination sequence and a PolII promoter and a PolII transcription termination sequence each operably linked to a DNA segment for influenza virus NS, e.g., a full-length influenza virus NS cDNA, and/or a transcription cassette comprising a PolI promoter and a PolI transcription termination sequence and a PolII promoter and a PolII transcription termination sequence each operably linked to a DNA segment for influenza virus M, e.g., a full-length influenza virus M cDNA, wherein the composition or host cell may have any combination of the vectors. In one embodiment, an adenovirus vector may include two transcription cassettes, each with different influenza virus sequences, e.g., NS and M sequences. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

Further provided is a composition or host cell comprising a plurality of vectors including adenovirus vectors that may include a transcription cassette comprising a PolI promoter operably linked to an influenza virus PA DNA, e.g., a full-length influenza virus PA cDNA, linked to a PolI transcription termination sequence, a transcription cassette comprising a PolI promoter operably linked to an influenza virus PB1 DNA, e.g., a full-length influenza virus PB1 cDNA, linked to a PolI transcription termination sequence, a transcription cassette comprising a PolI promoter operably linked to an influenza virus PB2 DNA, a full-length influenza virus PB2 cDNA, linked to a PolI transcription termination sequence, a transcription cassette comprising a PolI promoter operably linked to an influenza virus HEF DNA, e.g., a full-length influenza virus HEF cDNA, linked to a PolI transcription termination sequence, a transcription cassette comprising a PolI promoter operably linked to an influenza virus NP DNA, e.g., a full-length influenza virus NP cDNA, linked to a PolI transcription termination sequence, a PolI promoter operably linked to an influenza virus M DNA, e.g., a full-length influenza virus M cDNA, linked to a PolI transcription termination sequence, or a transcription cassette comprising a promoter operably linked to an influenza virus NS DNA, e.g., a full-length influenza virus NS cDNA, linked to a PolI transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and/or a transcription cassette comprising a PolII promoter operably linked to a DNA coding region for influenza virus NP linked to a PolII transcription termination sequence, wherein the composition or host cell may have any combination of the vectors. In one embodiment, an adenovirus vector may include two transcription cassettes, each with different influenza virus sequences, e.g., NS and M sequences. In one embodiment, in place of PolI promoters and transcription termination sequences, the adenovirus vectors include RNA PolIII, T3 or T7 promoter and transcription termination sequences, or a PolII promoter-ribozyme and a ribozyme-PolII transcription termination sequence. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

In one embodiment, the invention provides a composition or host cell comprising vectors that include isolated adenovirus vectors which include a transcription cassette comprising a PolI promoter and a PolI transcription termination sequence and a PolII promoter and a PolII transcription termination sequence, each operably linked to an influenza virus PA DNA, e.g., a full-length influenza virus PA cDNA, a transcription cassette comprising a PolI promoter and a PolI transcription termination sequence and a PolII promoter and a PolII transcription termination sequence, each operably linked to an influenza virus PB1 DNA, e.g., a full-length influenza virus PB1 cDNA, a transcription cassette comprising a PolI promoter and a PolI transcription termination sequence and a PolII promoter and a PolII transcription termination sequence, each operably linked to an influenza virus PB2 DNA, e.g., a full-length influenza virus PB2 cDNA, a transcription cassette comprising a PolI promoter and a PolI transcription termination sequence and a PolII promoter and a PolII transcription termination sequence, each operably linked to an influenza virus HEF DNA, e.g., a full-length influenza virus HEF cDNA, a transcription cassette comprising a PolI promoter and a PolI transcription termination sequence and a PolII promoter and a PolII transcription termination sequence, each operably linked to an influenza virus NP DNA, e.g., a full-length influenza virus NP cDNA, a transcription cassette comprising a PolI promoter and a PolI transcription termination sequence and a PolII promoter and a PolII transcription termination sequence, each operably linked to an influenza virus M DNA, e.g., a full-length influenza virus M cDNA, a transcription cassette comprising a PolI promoter and a PolI transcription termination sequence and a PolII promoter and a PolII transcription termination sequence, each operably linked to an influenza virus NS DNA, e.g., a full-length influenza virus NS cDNA, wherein the composition or host cell may have any combination of the vectors. In one embodiment, the influenza DNA is a cDNA with a native (naturally occurring) influenza virus sequence.

In one embodiment, the influenza DNA is a cDNA that has been manipulated in vitro, e.g., by inserting, deleting or substituting, or a combination thereof, one or more nucleotides in, for example, the coding region.

In one embodiment, the invention provides a composition or host cell comprising isolated adenovirus vectors having a plurality of transcription cassettes: a transcription cassette comprising a PolI promoter operably linked to an influenza virus PA DNA, e.g., a full-length influenza virus PA cDNA, linked to a PolI transcription termination sequence, a transcription cassette comprising a PolI promoter operably linked to an influenza virus PB1 DNA, e.g., a full-length influenza virus PB1 cDNA, linked to a PolI transcription termination sequence, a transcription cassette comprising a PolI promoter operably linked to an influenza virus PB2 DNA, e.g., a full-length influenza virus PB2 cDNA, linked to a PolI transcription termination sequence, a transcription cassette comprising a PolI promoter operably linked to an influenza virus HA DNA, e.g., a full-length influenza virus HA cDNA, linked to a PolI transcription termination sequence, a transcription cassette comprising a PolI promoter operably linked to an influenza virus NP DNA, e.g., a full-length influenza virus NP cDNA, linked to a PolI transcription termination sequence, a transcription cassette comprising a PolI promoter operably linked to an influenza virus M DNA, e.g., a full-length influenza virus M cDNA, linked to a PolI transcription termination sequence, a transcription cassette comprising a PolI promoter operably linked to an influenza virus NS DNA, e.g., a full-length influenza virus NS cDNA, linked to a PolI transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, a transcription cassette comprising a PolII promoter operably linked to a DNA coding region for influenza virus NP linked to a PolII transcription termination sequence, and optionally one or more of the following: a transcription cassette comprising a PolII promoter and a PolII transcription termination operably linked to a DNA segment for influenza virus HA, e.g., a full-length influenza virus HA cDNA, a transcription cassette comprising a PolII promoter and a PolII transcription termination sequence operably linked to a DNA segment for influenza virus M, e.g., a full-length influenza virus M cDNA, and/or a transcription cassette comprising a PolII promoter sequence and a PolII transcription termination sequence operably linked to a DNA segment for influenza virus NS, e.g., a full-length influenza virus NS cDNA, wherein the composition or host cell may have any combination of the vectors. Thus, in this embodiment, the set of adenovirus vectors or composition with a set of adenovirus vectors does not include NA sequences, i.e., it is a NAvirus. That is, the set of vectors or host cell infected with the set of vectors does not include sequences corresponding to NA coding or noncoding sequences for vRNA production or for vRNA production and mRNA production.

The invention also provides a composition or host cell comprising vectors that include isolated adenovirus vectors having a transcription cassette comprising a PolII promoter linked to a ribozyme sequence linked to an influenza virus PA DNA, e.g., a full-length influenza virus PA cDNA, linked to a ribozyme sequence linked to a PolII transcription termination sequence, a transcription cassette comprising a PolII promoter linked to a ribozyme sequence linked to an influenza virus PB1 DNA, e.g., a full-length influenza virus PB1 cDNA, linked to a ribozyme sequence linked to a PolII transcription termination sequence, a transcription cassette comprising a PolII promoter linked to a ribozyme sequence linked to an influenza virus PB2 DNA, e.g., a full-length influenza virus PB2 cDNA, linked to a ribozyme sequence linked to a PolII transcription termination sequence, a transcription cassette comprising a PolII promoter linked to a ribozyme sequence linked to an influenza virus HA DNA, e.g., a full-length influenza virus HA cDNA, linked to a ribozyme sequence linked to a PolII transcription termination sequence, a transcription cassette comprising a PolII promoter linked to a ribozyme sequence linked to an influenza virus NP DNA, e.g., a full-length influenza virus NP cDNA, linked to a ribozyme sequence linked to a PolII transcription termination sequence, a transcription cassette comprising a PolII promoter linked to a ribozyme sequence linked to an influenza virus M DNA, e.g., a full-length influenza virus M cDNA, linked to a ribozyme sequence linked to a PolII transcription termination sequence, a transcription cassette comprising a PolII promoter linked to a ribozyme sequence linked to an influenza virus NS DNA, e.g., a full-length influenza virus NS cDNA, linked to a ribozyme sequence linked to a PolII transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, a transcription cassette comprising a PolII promoter operably linked to a DNA coding region for influenza virus NP linked to a PolII transcription termination sequence, and optionally one or more of the following: a transcription cassette comprising a PolII promoter and a PolII transcription termination operably linked to a DNA segment for influenza virus HA, e.g., a full-length influenza virus HA cDNA, a transcription cassette comprising a PolII promoter and a PolII transcription termination sequence operably linked to a DNA segment for influenza virus M, e.g., a full-length influenza virus M cDNA, and/or a transcription cassette comprising a PolII promoter sequence and a PolII transcription termination sequence operably linked to a DNA segment for influenza virus NS, e.g., a full-length influenza virus NS cDNA, wherein the composition or host cell may have any combination of the vectors. In this embodiment, the set of adenovirus vectors or composition with a set of adenovirus vectors does not include NA coding sequences. That is, the set of vectors or host cell infected with the set of vectors does not include sequences corresponding to NA coding or noncoding sequences for vRNA production or for vRNA production and mRNA production.

The invention provides a composition or host cell comprising retroviral vectors that may include a transcription cassette comprising a PolI promoter operably linked to an influenza virus PA DNA, e.g., a full-length influenza virus PA cDNA, linked to a PolI transcription termination sequence, a transcription cassette comprising a PolI promoter operably linked to an influenza virus PB1 DNA, e.g., a full-length influenza virus PB1 cDNA, linked to a PolI transcription termination sequence, a transcription cassette comprising a PolI promoter operably linked to an influenza virus PB2 DNA, e.g., a full-length influenza virus PB2 cDNA, linked to a PolI transcription termination sequence, a transcription cassette comprising a PolI promoter operably linked to an influenza virus HA DNA, e.g., a full-length influenza virus HA cDNA, linked to a PolI transcription termination sequence, a transcription cassette comprising a PolI promoter operably linked to an influenza virus NP DNA, e.g., a full-length influenza virus NP cDNA, linked to a PolI transcription termination sequence, a transcription cassette comprising a PolI promoter operably linked to an influenza virus NA DNA, e.g., a full-length influenza virus NA cDNA, linked to a PolI transcription termination sequence, a transcription cassette comprising a PolI promoter operably linked to an influenza virus M DNA, e.g., a full-length influenza virus M cDNA, linked to a PolI transcription termination sequence, a transcription cassette comprising a PolI promoter operably linked to an influenza virus NS DNA, e.g., a full-length influenza virus NS cDNA, linked to a PolI transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, a transcription cassette comprising a PolII promoter operably linked to a DNA coding region for influenza virus NP linked to a PolII transcription termination sequence, wherein the composition or host cell may have any combination of the vectors. In one embodiment, a retrovirus vector may include two transcription cassettes, each with different influenza virus sequences, e.g., NS and M sequences. In one embodiment, in place of PolI promoters and transcription termination sequences, the retrovirus vectors include RNA PolIII, T3 or T7 promoter and transcription termination sequences, or a PolII promoter-ribozyme and a ribozyme-PolII transcription termination sequence. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

The invention also provides a composition or host cell that may include a plurality of retrovirus vectors having transcription cassettes that include a transcription cassette comprising a PolI promoter operably linked to an influenza virus PA DNA, e.g., a full-length influenza virus PA cDNA, linked to a PolI transcription termination sequence, a transcription cassette comprising a PolI promoter operably linked to an influenza virus PB1 DNA, e.g., a full-length influenza virus PB1 cDNA, linked to a PolI transcription termination sequence, a transcription cassette comprising a PolI promoter operably linked to an influenza virus PB2 DNA, e.g., a full-length influenza virus PB2 cDNA, linked to a PolI transcription termination sequence, a transcription cassette comprising a PolI promoter operably linked to an influenza virus HA DNA, e.g., a full-length HA cDNA, linked to a PolI transcription termination sequence, a transcription cassette comprising a PolI promoter operably linked to an influenza virus NP DNA, e.g., a full-length influenza virus NP cDNA, linked to a PolI transcription termination sequence, a transcription cassette comprising a PolI promoter operably linked to an influenza virus NB and NA DNA, e.g., a full-length influenza virus NB and NA cDNA, linked to a PolI transcription termination sequence, a transcription cassette comprising a PolI promoter operably linked to an influenza virus M DNA, e.g., a full-length influenza virus M cDNA, linked to a PolI transcription termination sequence, and a transcription cassette comprising a PolI promoter operably linked to an influenza virus NS DNA, e.g., a full-length influenza virus NS cDNA, linked to a PolI transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and/or a transcription cassette comprising a PolII promoter operably linked to a DNA coding region for influenza virus NP linked to a PolII transcription termination sequence, wherein the composition or host cell may have any combination of the vectors. In one embodiment, a retrovirus vector may include two transcription cassettes, each with different influenza virus sequences, e.g., NS and M sequences. In one embodiment, in place of PolI promoters and transcription termination sequences, the retrovirus vectors include RNA PolIII, T3 or T7 promoter and transcription termination sequences, or a PolII promoter-ribozyme and a ribozyme-PolII transcription termination sequence. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

The invention further includes a composition or host cell comprising vectors including retrovirus vectors with a transcription cassette comprising a PolI promoter and a PolI transcription termination sequence and a PolII promoter and a PolII transcription termination sequence, each operably linked to a DNA segment for influenza virus PA, e.g., a full-length influenza virus PA cDNA, a transcription cassette comprising a PolI promoter and a PolI transcription termination sequence and a PolII promoter and a PolII transcription termination sequence each operably linked to a DNA segment for influenza virus PB1, e.g., a full-length influenza virus PB1 cDNA, a transcription cassette comprising a PolI promoter and a PolI transcription termination sequence and a PolII promoter and a PolII transcription termination sequence each operably linked to a DNA segment for influenza virus PB2, e.g., a full-length influenza virus PB2 cDNA, a transcription cassette comprising a PolI promoter and a PolI transcription termination sequence and a PolII promoter and a PolII transcription termination sequence each operably linked to a DNA segment for influenza virus NP, e.g., a full-length influenza virus NP cDNA, a transcription cassette comprising a PolI promoter and a PolI transcription termination sequence and a PolII promoter and a PolII transcription termination sequence each operably linked to a DNA segment for influenza virus HA, e.g., a full-length influenza virus HA cDNA, a transcription cassette comprising a PolI promoter and a PolI transcription termination sequence and a PolII promoter and a PolII transcription termination sequence each operably linked to a DNA segment for influenza virus NA, e.g., a full-length influenza virus NA cDNA, a transcription cassette comprising a PolI promoter and a PolI transcription termination sequence and a PolII promoter and a PolII transcription termination sequence each operably linked to a DNA segment for influenza virus NS, e.g., a full-length influenza virus NS cDNA, and a transcription cassette comprising a PolI promoter and a PolI transcription termination sequence and a PolII promoter and a PolII transcription termination sequence each operably linked to a DNA segment for influenza virus M, e.g., a full-length influenza virus M cDNA, wherein the composition or host cell may have any combination of the vectors. In one embodiment, an adenovirus vector may include two transcription cassettes, each with different influenza virus sequences, e.g., NS and M sequences. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

The invention further includes a composition or host cell comprising vectors that include retrovirus vectors with a transcription cassette comprising a PolI promoter and a PolI transcription termination sequence and a PolII promoter and a PolII transcription termination sequence, each operably linked to a DNA segment for influenza virus PA, e.g., a full-length influenza virus PA cDNA, a transcription cassette comprising a PolI promoter and a PolI transcription termination sequence and a PolII promoter and a PolII transcription termination sequence each operably linked to a DNA segment for influenza virus PB1, e.g., a full-length influenza virus PB1 cDNA, a transcription cassette comprising a PolI promoter and a PolI transcription termination sequence and a PolII promoter and a PolII transcription termination sequence each operably linked to a DNA segment for influenza virus PB2, e.g., a full-length influenza virus PB2 cDNA, a transcription cassette comprising a PolI promoter and a PolI transcription termination sequence and a PolII promoter and a PolII transcription termination sequence each operably linked to a DNA segment for influenza virus NP, e.g., a full-length influenza virus NP cDNA, a transcription cassette comprising a PolI promoter and a PolI transcription termination sequence and a PolII promoter and a PolII transcription termination sequence each operably linked to a DNA segment for influenza virus HA, e.g., a full-length influenza virus HA cDNA, a transcription cassette comprising a PolI promoter and a PolI transcription termination sequence and a PolII promoter and a PolII transcription termination sequence each operably linked to a DNA segment for influenza virus NA and NB, e.g., a full-length influenza virus NA and NB cDNA, a transcription cassette comprising a PolI promoter and a PolI transcription termination sequence and a PolII promoter and a PolII transcription termination sequence each operably linked to a DNA segment for influenza virus NS, e.g., a full-length influenza virus NS cDNA, and a transcription cassette comprising a PolI promoter and a PolI transcription termination sequence and a PolII promoter and a PolII transcription termination sequence each operably linked to a DNA segment for influenza virus M, e.g., a full-length influenza virus M cDNA, wherein the composition or host cell may have any combination of the vectors. In one embodiment, an adenovirus vector may include two transcription cassettes, each with different influenza virus sequences, e.g., NS and M sequences. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

Further provided is a composition or host cell comprising vectors that include retrovirus vectors which include a transcription cassette comprising a PolI promoter operably linked to an influenza virus PA DNA, e.g., a full-length influenza virus PA cDNA, linked to a PolI transcription termination sequence, a transcription cassette comprising a PolI promoter operably linked to an influenza virus PB1 DNA, e.g., a full-length influenza virus PB1 cDNA, linked to a PolI transcription termination sequence, a transcription cassette comprising a PolI promoter operably linked to an influenza virus PB2 DNA, a full-length influenza virus PB2 cDNA, linked to a PolI transcription termination sequence, a transcription cassette comprising a PolI promoter operably linked to an influenza virus HEF DNA, e.g., a full-length influenza virus HEF cDNA, linked to a PolI transcription termination sequence, a transcription cassette comprising a PolI promoter operably linked to an influenza virus NP DNA, e.g., a full-length influenza virus NP cDNA, linked to a PolI transcription termination sequence, a PolI promoter operably linked to an influenza virus M DNA, e.g., a full-length influenza virus M cDNA, linked to a PolI transcription termination sequence, or a transcription cassette comprising a promoter operably linked to an influenza virus NS DNA, e.g., a full-length influenza virus NS cDNA, linked to a PolI transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, and/or a transcription cassette comprising a PolII promoter operably linked to a DNA coding region for influenza virus NP linked to a PolII transcription termination sequence, wherein the composition or host cell may have any combination of the vectors. In one embodiment, a retrovirus vector may include two transcription cassettes, each with different influenza virus sequences, e.g., NS and M sequences. In one embodiment, in place of PolI promoters and transcription termination sequences, the retrovirus vectors include RNA PolIII, T3 or T7 promoter and transcription termination sequences, or a PolIII promoter-ribozyme and a ribozyme-PolII transcription termination sequence. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

In one embodiment, the invention provides a composition or host cell comprising vectors that include retrovirus vectors which include a transcription cassette comprising a PolI promoter and a PolI transcription termination sequence and a PolII promoter and a PolII transcription termination sequence, each operably linked to an influenza virus PA DNA, e.g., a full-length influenza virus PA cDNA, a transcription cassette comprising a PolI promoter and a PolI transcription termination sequence and a PolII promoter and a PolII transcription termination sequence, each operably linked to an influenza virus PB1 DNA, e.g., a full-length influenza virus PB1 cDNA, a transcription cassette comprising a PolI promoter and a PolI transcription termination sequence and a PolII promoter and a PolII transcription termination sequence, each operably linked to an influenza virus PB2 DNA, e.g., a full-length influenza virus PB2 cDNA, a transcription cassette comprising a PolI promoter and a PolI transcription termination sequence and a PolII promoter and a PolII transcription termination sequence, each operably linked to an influenza virus HEF DNA, e.g., a full-length influenza virus HEF cDNA, a transcription cassette comprising a PolI promoter and a PolI transcription termination sequence and a PolII promoter and a PolII transcription termination sequence, each operably linked to an influenza virus NP DNA, e.g., a full-length influenza virus NP cDNA, a transcription cassette comprising a PolI promoter and a PolI transcription termination sequence and a PolII promoter and a PolII transcription termination sequence, each operably linked to an influenza virus M DNA, e.g., a full-length influenza virus M cDNA, a transcription cassette comprising a PolI promoter and a PolI transcription termination sequence and a PolII promoter and a PolII transcription termination sequence, each operably linked to an influenza virus NS DNA, e.g., a full-length influenza virus NS cDNA, wherein the composition or host cell may have any combination of the vectors. In one embodiment, the influenza DNA is a cDNA with a native (naturally occurring) influenza virus sequence. In one embodiment, the influenza DNA is a cDNA that has been manipulated in vitro, e.g., by inserting, deleting or substituting, or a combination thereof, one or more nucleotides in, for example, the coding region.

In one embodiment, the invention provides a composition or host cell comprising vectors that include retrovirus vectors having a plurality of transcription cassettes: a transcription cassette comprising a PolI promoter operably linked to an influenza virus PA DNA, e.g., a full-length influenza virus PA cDNA, linked to a PolI transcription termination sequence, a transcription cassette comprising a PolI promoter operably linked to an influenza virus PB1 DNA, e.g., a full-length influenza virus PB1 cDNA, linked to a PolI transcription termination sequence, a transcription cassette comprising a PolI promoter operably linked to an influenza virus PB2 DNA, e.g., a full-length influenza virus PB2 cDNA, linked to a PolI transcription termination sequence, a transcription cassette comprising a PolI promoter operably linked to an influenza virus HA DNA, e.g., a full-length influenza virus HA cDNA, linked to a PolI transcription termination sequence, a transcription cassette comprising a PolI promoter operably linked to an influenza virus NP DNA, e.g., a full-length influenza virus NP cDNA, linked to a PolI transcription termination sequence, a transcription cassette comprising a PolI promoter operably linked to an influenza virus M DNA, e.g., a full-length influenza virus M cDNA, linked to a PolI transcription termination sequence, a transcription cassette comprising a PolI promoter operably linked to an influenza virus NS DNA, e.g., a full-length influenza virus NS cDNA, linked to a PolI transcription termination sequence, a transcription cassette comprising a PolI promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, a transcription cassette comprising a PolII promoter operably linked to a DNA coding region for influenza virus NP linked to a PolII transcription termination sequence, and optionally one or more of the following: a transcription cassette comprising a PolII promoter and a PolII transcription termination operably linked to a DNA segment for influenza virus HA, e.g., a full-length influenza virus HA cDNA, a transcription cassette comprising a PolII promoter and a PolII transcription termination sequence operably linked to a DNA segment for influenza virus M, e.g., a full-length influenza virus M cDNA, and/or a transcription cassette comprising a PolII promoter sequence and a PolII transcription termination sequence operably linked to a DNA segment for influenza virus NS, e.g., a full-length influenza virus NS cDNA, wherein the composition or host cell may have any combination of the vectors. Thus, in this embodiment, the set of retrovirus vectors or composition with a set of retrovirus vectors does not include NA sequences, i.e., it is a NAvirus. That is, the set of vectors or host cell infected with the set of vectors does not include sequences corresponding to NA coding or noncoding sequences for vRNA production or for vRNA production and mRNA production.

The invention also provides a composition or host cell comprising vectors including isolated retrovirus vectors having a transcription cassette comprising a PolII promoter linked to a ribozyme sequence linked to an influenza virus PA DNA, e.g., a full-length influenza virus PA cDNA, linked to a ribozyme sequence linked to a PolII transcription termination sequence, a transcription cassette comprising a PolII promoter linked to a ribozyme sequence linked to an influenza virus PB1 DNA, e.g., a full-length influenza virus PB1 cDNA, linked to a ribozyme sequence linked to a PolII transcription termination sequence, a transcription cassette comprising a PolII promoter linked to a ribozyme sequence linked to an influenza virus PB2 DNA, e.g., a full-length influenza virus PB2 cDNA, linked to a ribozyme sequence linked to a PolII transcription termination sequence, a transcription cassette comprising a PolII promoter linked to a ribozyme sequence linked to an influenza virus HA DNA, e.g., a full-length influenza virus HA cDNA, linked to a ribozyme sequence linked to a PolII transcription termination sequence, a transcription cassette comprising a PolII promoter linked to a ribozyme sequence linked to an influenza virus NP DNA, e.g., a full-length influenza virus NP cDNA, linked to a ribozyme sequence linked to a PolII transcription termination sequence, a transcription cassette comprising a PolII promoter linked to a ribozyme sequence linked to an influenza virus M DNA, e.g., a full-length influenza virus M cDNA, linked to a ribozyme sequence linked to a PolII transcription termination sequence, a transcription cassette comprising a PolII promoter linked to a ribozyme sequence linked to an influenza virus NS DNA, e.g., a full-length influenza virus NS cDNA, linked to a ribozyme sequence linked to a PolII transcription termination sequence, a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, a transcription cassette comprising a PolII promoter operably linked to a DNA coding region for influenza virus PB2 linked to a PolII transcription termination sequence, a transcription cassette comprising a PolII promoter operably linked to a DNA coding region for influenza virus NP linked to a PolII transcription termination sequence, and optionally one or more of the following: a transcription cassette comprising a PolII promoter and a PolII transcription termination operably linked to a DNA segment for influenza virus HA, e.g., a full-length influenza virus HA cDNA, a transcription cassette comprising a PolII promoter and a PolII transcription termination sequence operably linked to a DNA segment for influenza virus M, e.g., a full-length influenza virus M cDNA, and/or a transcription cassette comprising a PolII promoter sequence and a PolII transcription termination sequence operably linked to a DNA segment for influenza virus NS, e.g., a full-length influenza virus NS cDNA, wherein the composition or host cell may have any combination of the vectors. In this embodiment, the set of retrovirus vectors or composition with a set of retrovirus vectors does not include NA coding sequences. That is, the set of vectors or host cell infected with the set of vectors does not include sequences corresponding to NA coding or noncoding sequences for vRNA production or for vRNA production and mRNA production.

In one embodiment, the HA in a transcription cassette is a type A HA. In another embodiment, the HA in a transcription cassette is a type B HA. In one embodiment, the RNA PolI promoter is a human RNA PolI promoter. In one embodiment, the NA cDNA in a transcription cassette is a type B NA cDNA, i.e., one having NA and NB. In one embodiment, the composition further includes a transcription cassette comprising a PolI promoter operably linked to an influenza virus M cDNA, e.g., one having M1 and BM2, linked to a PolI transcription termination sequence.

In one embodiment, the cell is stably or transiently transfected with vectors encoding all but HA and NA sequences. Those cells are then infected with the adenovirus or retrovirus vectors of the invention having HA sequences. In another embodiment, the cell is stably or transiently transfected with vectors encoding all but HA sequences. Those cells are then infected with the adenovirus or retrovirus vectors of the invention having HA sequences.

Exemplary Methods

The invention provides a method to prepare influenza virus using recombinant adenovirus or retrovirus vectors as described herein. In one embodiment, the method includes contacting a cell with recombinant adenovirus or retrovirus vectors having a transcription cassette comprising a PolI promoter operably linked to an influenza virus PA DNA, e.g., a full-length influenza virus PA cDNA, linked to a PolI transcription termination sequence, a transcription cassette comprising a PolI promoter operably linked to an influenza virus PB1 DNA, e.g., a full-length influenza virus PB1 cDNA, linked to a PolI transcription termination sequence, a transcription cassette comprising a PolI promoter operably linked to an influenza virus PB2 DNA, e.g., a full-length influenza virus PB2 cDNA, linked to a PolI transcription termination sequence, a transcription cassette comprising a PolI promoter operably linked to an influenza virus HA DNA, e.g., a full-length influenza virus HA cDNA, linked to a PolI transcription termination sequence, a transcription cassette comprising a PolI promoter operably linked to an influenza virus NP DNA, e.g., a full-length influenza virus NP cDNA, linked to a PolI transcription termination sequence, a transcription cassette comprising a PolI promoter operably linked to an influenza virus NA DNA, e.g., a full-length influenza virus NA cDNA, linked to a PolI transcription termination sequence, and/or a transcription cassette comprising a PolI promoter operably linked to an influenza virus M DNA, e.g., a full-length influenza virus M cDNA, linked to a PolI transcription termination sequence and/or a transcription cassette comprising a PolI promoter operably linked to an influenza virus NS DNA, e.g., a full-length influenza virus NS cDNA, linked to a PolI transcription termination sequence, a transcription cassette comprising a PolII promoter operably linked to a DNA coding region for influenza virus PA, a transcription cassette comprising a PolII promoter operably linked to a DNA coding region for influenza virus PB1, a transcription cassette comprising a PolII promoter operably linked to a DNA coding region for influenza virus PB2, and/or a transcription cassette comprising a PolII promoter operably linked to a DNA coding region for influenza virus NP.

In one embodiment, a method to prepare influenza virus includes contacting a host cell with recombinant adenovirus or retrovirus vectors that include a transcription cassette comprising a PolI promoter and a PolI transcription termination sequence and a PolI promoter and a PolI transcription termination sequence, each linked to an influenza virus HA DNA, e.g., a full-length influenza virus HA cDNA, a transcription cassette comprising a PolI promoter and a PolI transcription termination sequence and a PolII promoter and a PolII transcription termination sequence, each operably linked to an influenza virus NA DNA, e.g., a full-length influenza virus NA cDNA, a transcription cassette comprising a PolI promoter and a PolI transcription termination sequence and a PolII promoter and a PolII transcription termination sequence, each operably linked to an influenza virus M cDNA, e.g., a full-length influenza virus M cDNA, a transcription cassette comprising a PolI promoter and a PolI transcription termination sequence and a PolII promoter and a PolII transcription termination sequence each operably linked to an influenza virus NS DNA, e.g., a full-length influenza virus NS cDNA, from a transcription cassette comprising a PolI promoter and a PolI transcription termination sequence and a PolII promoter and a PolII transcription termination sequence, each operably linked to a influenza virus PA DNA, e.g., a full-length influenza virus PA cDNA, a transcription cassette comprising a PolI promoter and a PolI transcription termination sequence and a PolII promoter and a PolII transcription termination sequence, each operably linked to influenza virus PB1 DNA, e.g., a full-length influenza virus PB1 cDNA, a transcription cassette comprising a PolI promoter and a PolI transcription termination sequence and a PolII promoter and a PolII transcription termination sequence each operably linked to influenza virus PB2 DNA, e.g., a full-length influenza virus PB2 cDNA, and a transcription cassette comprising a PolI promoter and a PolI transcription termination sequence and a PolII promoter and a PolII transcription termination sequence, each operably linked to influenza virus NP DNA, e.g., a full-length influenza virus NP cDNA.

In another embodiment, the invention provides a method to prepare influenza virus which includes contacting a cell with a recombinant adenovirus or retrovirus vectors which include a transcription cassette comprising a PolI promoter and a PolI transcription termination sequence and a PolII promoter and a PolII transcription termination sequence each operably linked to an influenza virus PA DNA, e.g., a full-length influenza virus PA cDNA, a transcription cassette comprising a PolI promoter and a PolI transcription termination sequence and a PolII promoter and PolII transcription termination sequence each operably linked to an influenza virus PB1 DNA, e.g., a full-length influenza virus PB1 cDNA, a transcription cassette comprising a PolI promoter and a PolI transcription termination sequence and a PolII promoter and a PolII transcription termination sequence each operably linked to an influenza virus PB2 DNA, e.g., a full-length influenza virus PB2 cDNA, a transcription cassette comprising a PolI promoter and a PolI transcription termination sequence and a PolII promoter and a PolII transcription termination sequence each operably linked to an influenza virus HEF DNA, e.g., a full-length influenza virus HEF cDNA, a transcription cassette comprising a PolI promoter and a PolI transcription termination sequence and a PolII promoter and a PolII transcription termination sequence each operably linked to an influenza virus NP DNA, e.g., a full-length influenza virus NP cDNA, a transcription cassette comprising a PolI promoter and a PolI transcription termination sequence and a PolII promoter and a PolII transcription termination sequence each operably linked to an influenza virus M DNA, e.g., a full-length influenza virus M cDNA, and a PolI and a transcription cassette comprising a PolI promoter and a PolI transcription termination sequence each operably linked to an influenza virus NS cDNA, e.g., a full-length influenza virus NS cDNA.

The invention also provides a method to prepare an attenuated influenza virus. The method includes contacting a host cell with a plurality of adenovirus vectors having a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2 cDNA, e.g., a full-length influenza virus PB2 cDNA, linked to a PolI transcription termination sequence, a transcription cassette comprising a PolI promoter operably linked to an influenza virus HA cDNA, e.g., a full-length influenza virus HA cDNA, linked to a PolI transcription termination sequence, a transcription cassette comprising a PolI promoter operably linked to an influenza virus NP cDNA, e.g., a full-length influenza virus NP cDNA, linked to a PolI transcription termination sequence, and/or a transcription cassette comprising a PolI promoter operably linked to an influenza virus M cDNA, e.g., a full-length influenza virus M cDNA, linked to a PolI transcription termination sequence and/or a transcription cassette comprising a PolI promoter operably linked to an influenza virus NS cDNA, e.g., a full-length influenza virus NS cDNA, linked to a PolI transcription termination sequence; and a plurality of adenovirus vectors having a transcription cassette comprising a PolII promoter operably linked to a DNA coding region for influenza virus PA, a transcription cassette comprising a PolII promoter operably linked to a DNA coding region for influenza virus PB1, a transcription cassette comprising a PolII promoter operably linked to a DNA coding region for influenza virus PB2, and/or a transcription cassette comprising a PolII promoter operably linked to a DNA coding region for influenza virus NP.

In one embodiment, a method to prepare an attenuated influenza virus includes contacting a cell with a plurality of retrovirus vectors which include a transcription cassette comprising a PolI promoter operably linked to an influenza virus HA cDNA, e.g., a full-length influenza virus HA cDNA, linked to a PolI transcription termination sequence, a transcription cassette comprising a PolI promoter operably linked to an influenza virus M cDNA, e.g., a full-length influenza virus M cDNA, linked to a PolI transcription termination sequence, a transcription cassette comprising a PolI promoter operably linked to an influenza virus NS cDNA, e.g., a full-length influenza virus NS cDNA, linked to a PolI transcription termination sequence, a transcription cassette comprising a PolI promoter operably linked to an influenza virus PA cDNA, e.g., a full-length influenza virus PA cDNA, linked to a PolI transcription termination sequence, a transcription cassette comprising a PolI promoter operably linked to an influenza virus PB1 cDNA, e.g., a full-length influenza virus PB1 cDNA, linked to a PolI transcription termination sequence, a transcription cassette comprising a PolI promoter operably linked to an influenza virus PB2, e.g., a full-length influenza virus PB2 cDNA, and a PolI transcription termination sequence, and a transcription cassette comprising a PolI promoter operably linked to an influenza virus NP cDNA, e.g., a full-length influenza virus NP cDNA, linked to a PolI transcription termination sequence.

In one embodiment, the method of the invention includes contacting a cell with a vector comprising a transcription cassette comprising a promoter linked to 5' influenza virus sequences comprising 5' influenza virus noncoding sequences and optionally adjacent portions of the coding sequence (see PCT/US03/04233, which is incorporated by reference herein), linked to a DNA of interest linked to 3' influenza virus sequences comprising 3' influenza virus non-coding sequences and optionally adjacent portions of the coding sequence, linked to a transcription termination sequence (see PCT/US03/04233). In one embodiment, the DNA of interest is in the sense orientation. In another embodiment, the DNA of interest is in the negative sense (antigenic relative to influenza virus packaging sequence) orientation. The DNA of interest may include an open reading frame encoding an immunogenic polypeptide or peptide of a pathogen or a therapeutic polypeptide or peptide. The DNA of interest may be operably linked to a PolI promoter and a PolI transcription termination sequence, and/or the DNA of interest is operably linked to a PolII promoter and a PolII transcription termination sequence.

Cell Lines and Influenza Viruses that can be Used in the Present Invention

According to the present invention, any cell which supports efficient replication of influenza virus can be employed in the invention, including mutant cells which express reduced or decreased levels of one or more sialic acids which are receptors for influenza virus. Viruses obtained by the methods can be made into a reassortant virus.

Preferably, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity is preferably tested in cells that are at the same passage level as those used for vaccine production. The vaccine virus is preferably purified by a process that has been shown to give consistent results (see, e.g., World Health Organization, 1982).

It is preferred to establish a complete characterization of the cell lines to be used, so that appropriate tests for purity of the final product can be included. Data that can be used for the characterization of a cell to be used in the present invention includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. Preferably, the passage level, or population doubling, of the host cell used is as low as possible.

It is preferred that the virus produced in the cell is highly purified prior to vaccine or gene therapy formulation. Generally, the purification procedures will result in the extensive removal of cellular DNA, other cellular components, and adventitious agents. Procedures that extensively degrade or denature DNA can also be used. See, e.g., Mizrahi, 1990.

Vaccines

A vaccine of the invention may comprise immunogenic proteins including glycoproteins of any pathogen, e.g., an immunogenic protein from one or more bacteria, viruses, yeast or fungi. Thus, in one embodiment, the influenza viruses of the invention may be vaccine vectors for influenza virus or other viral pathogens including but not limited to lentiviruses such as HIV, hepatitis B virus, hepatitis C virus, herpes viruses such as CMV or HSV or foot and mouth disease virus.

A complete virion vaccine is concentrated by ultrafiltration and then purified by zonal centrifugation or by chromatography. It is inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976; Webster et al., 1977); or a nonionic detergent such as that commercialized under the name TRITON X100. The hemagglutinin may also be isolated after treatment of the virions with a protease such as bromelin, then purified by a method such as that described by Grand and Skehel (1972).

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done.

Inactivated Vaccines. Inactivated influenza virus vaccines of the invention are provided by inactivating replicated virus of the invention using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines. In general, the responses to SV and surface antigen (i.e., purified HA or NA) vaccines are similar. An experimental inactivated WV vaccine containing an NA antigen immunologically related to the epidemic virus and an unrelated HA appears to be less effective than conventional vaccines (Ogra et al., 1977). Inactivated vaccines containing both relevant surface antigens are preferred.

Live Attenuated Virus Vaccines. Live, attenuated influenza virus vaccines, can also be used for preventing or treating influenza virus infection, according to known method steps. Attenuation is preferably achieved in a single step by transfer of attenuated genes from an attenuated donor virus to a replicated isolate or reasserted virus according to known methods (see, e.g., Murphy, 1993). Since resistance to influenza A virus is mediated by the development of an immune response to the HA and NA glycoproteins, the genes coding for these surface antigens must come from the circulating wild-type strains. The attenuated genes are derived from the attenuated parent. In this approach, genes that confer attenuation preferably do not code for the HA and NA glycoproteins. Otherwise, these genes could not be transferred to reassortants bearing the surface antigens of the clinical virus isolate.

Many donor viruses have been evaluated for their ability to reproducibly attenuate influenza viruses. As a non-limiting example, the A/Ann Arbor(AA)/6/60 (H2N2) cold adapted (ca) donor virus can be used for attenuated vaccine production (see, e.g., Edwards, 1994; Murphy, 1993). Reassortant progeny are then selected at 25° C. (restrictive for replication of virulent virus), in the presence of an H2N2 antiserum, which inhibits replication of the viruses bearing the surface antigens of the attenuated A/AA/6/60 (H2N2) ca donor virus.

A large series of H1N1 and H3N2 reassortants have been evaluated in humans and found to be satisfactorily: (a) infectious, (b) attenuated for seronegative children and immunologically primed adults, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible adults and children.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced, for example, into the PB2 polymerase gene (Subbarao et al., 1993) or the NS gene. Thus, new donor viruses can also be generated bearing attenuating mutations introduced by site-directed mutagenesis, and such new donor viruses can be used in the production of live attenuated reassortant H1N1 and H3N2 vaccine candidates in a manner analogous to that described above for the A/AA/6/60 ca donor virus.

It is preferred that such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking infectivity to the degree that the vaccine causes minimal change of inducing a serious pathogenic condition in the vaccinated mammal.

The virus can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and DNA screening (such as probe hybridization or PCR) to confirm that donor genes encoding the antigenic determinants (e.g., HA or NA genes) are not present in the attenuated viruses. See, e.g., Robertson et al., 1988; Kilbourne, 1969; Aymard-Henry et al., 1985; Robertson et al., 1992.

Pharmaceutical Compositions

Pharmaceutical compositions of the present invention, suitable for inoculation or for parenteral or oral administration, comprise attenuated or inactivated influenza viruses, optionally further comprising sterile aqueous or non-aqueous solutions, suspensions, and emulsions. The compositions can further comprise auxiliary agents or excipients, as known in the art. See, e.g., Berkow et al., 1987; Avery's Drug Treatment, 1987; Osol, 1980. The composition of the invention is generally presented in the form of individual doses (unit doses).

Conventional vaccines generally contain about 0.1 to 200 µg, preferably 10 to 15 µg, of hemagglutinin from each of the strains entering into their composition. The vaccine forming the main constituent of the vaccine composition of the invention may comprise a virus of type A, B or C, or any combination thereof, for example, at least two of the three types, at least two of different subtypes, at least two of the same type, at least two of the same subtype, or a different isolate(s) or reassortant(s). Human influenza virus type A includes H1N1, H2N2 and H3N2 subtypes.

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents. See, e.g., Berkow et al., 1992; Avery's, 1987; and Osol, 1980.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized. Examples of materials suitable for use in vaccine compositions are provided in Osol (1980).

Heterogeneity in a vaccine may be provided by mixing replicated influenza viruses for at least two influenza virus strains, such as 2-50 strains or any range or value therein. Influenza A or B virus strains having a modern antigenic composition are preferred. According to the present invention, vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines, are provided before any symptom of a pathogen infection becomes manifest. The prophylactic administration of the composition serves to prevent or attenuate any subsequent infection. When provided prophylactically, the gene therapy compositions of the invention, are provided before any symptom of a disease becomes manifest. The prophylactic administration of the composition serves to prevent or attenuate one or more symptoms associated with the disease.

When provided therapeutically, an attenuated or inactivated viral vaccine is provided upon the detection of a symptom of actual infection. The therapeutic administration of the compound(s) serves to attenuate any actual infection. See, e.g., Berkow et al., 1992; and Avery, 1987. When provided therapeutically, a gene therapy composition is provided upon the detection of a symptom or indication of the disease. The therapeutic administration of the compound(s) serves to attenuate a symptom or indication of that disease.

Thus, an attenuated or inactivated vaccine composition of the present invention may thus be provided either before the onset of infection (so as to prevent or attenuate an anticipated infection) or after the initiation of an actual infection. Similarly, for gene therapy, the composition may be provided before any symptom of a disorder or disease is manifested or after one or more symptoms are detected.

A composition is said to be "pharmacologically acceptable" if its administration can be tolerated by a recipient patient. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of patients. Protection may be limited to mitigating the severity or rapidity of onset of symptoms of the influenza virus infection.

Pharmaceutical Administration

A composition of the present invention may confer resistance to one or more pathogens, e.g., one or more influenza virus strains, by either passive immunization or active immunization. In active immunization, an inactivated or attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a symptom or condition of the disease, or in the total or partial immunity of the individual to the disease. As used herein, a gene therapy composition is said to prevent or attenuate a disease if its administration results either in the total or partial attenuation (i.e., suppression) of a symptom or condition of the disease, or in the total or partial immunity of the individual to the disease.

At least one inactivated or attenuated influenza virus, or composition thereof, of the present invention may be administered by any means that achieve the intended purposes, using a pharmaceutical composition as previously described.

For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. A preferred mode of using a pharmaceutical composition of the present invention is by intramuscular or subcutaneous application. See, e.g., Berkow et al., 1992; and Avery, 1987.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired biological effect. It is understood that the effective dosage will be dependent upon the age, sex, health, and weight of the recipient, kind of concurrent treatment, if any, frequency of treatment, and the nature of the effect wanted. The ranges of effective doses provided below are not intended to limit the invention and represent preferred dose ranges. However, the most preferred dosage will be tailored to the individual subject, as is understood and determinable by one of skill in the art. See, e.g., Berkow et al., 1992; Avery's, 1987; and Ebadi, 1985.

The dosage of an attenuated virus vaccine for a mammalian (e.g., human) or avian adult organism can be from about $10^3$-$10^7$ plaque forming units (PFU)/kg, or any range or value therein. The dose of inactivated vaccine can range from about 0.1 to 200, e.g., 50 μg of hemagglutinin protein. However, the dosage should be a safe and effective amount as determined by conventional methods, using existing vaccines as a starting point.

The dosage of immunoreactive HA in each dose of replicated virus vaccine can be standardized to contain a suitable amount, e.g., 1-50 μg or any range or value therein, or the amount recommended by the U.S. Public Heath Service (PHS), which is usually 15 μg, per component for older children 3 years of age, and 7.5 μg per component for older children <3 years of age. The quantity of NA can also be standardized, however, this glycoprotein can be labile during the processor purification and storage. Each 0.5-ml dose of vaccine preferably contains approximately 1-50 billion virus particles, and preferably 10 billion particles.

The invention will be further described by the following nonlimiting example.

Example I

Figure 1B:
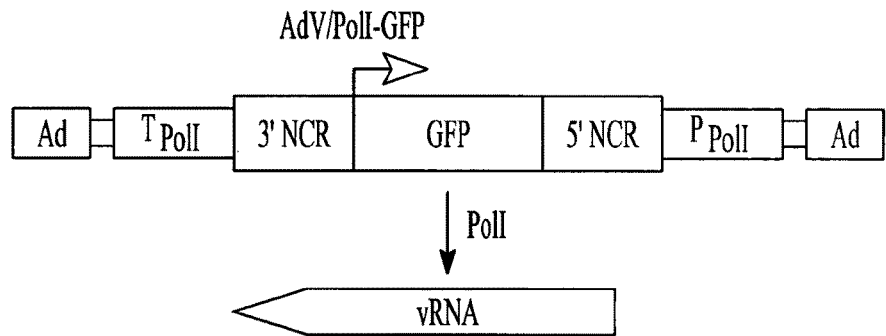

AdV-mediated synthesis of influenza vRNA. In plasmid-based reverse genetics systems, plasmids possessing the cDNA of viral genes under the control of the human PolI promoter and the mouse PolI terminator have been used for vRNA synthesis (Neumann et al., 1999). The cDNA corresponding to the transcriptional region in pPolI-GFP (FIG. 1A; Neumann et al., 2000) was cloned into pAd/PL-DEST (Invitrogen), which contains E1 and E3-deleted human adenovirus type 5 genome sequence as a viral vector backbone, by means of the Gateway system using LR clonase (Invitrogen). Transfection of the resultant plasmid into 293A cells produced AdV for the synthesis of a reporter vRNA (AdV/PolI-GFP; FIG. 1B).

To test whether AdV/PolI-GFP can produce the reporter vRNA in Vero cells, that AdV was transduced into cells. These cells were simultaneously transfected with four plasmids to express the A/WSN/33(H1N1, WSN) viral polymerase subunits (PB2, PB1, and PA) and NP, which are necessary and sufficient for vRNA transcription and replication and which form the viral ribonucleoprotein complexes (vRNPs) with vRNA. The multiplicity of infection (MOI) used was 50, an MOI at which >99% of the cells express a transduced gene (data not shown). Forty-eight hours later, GFP-expressing cells were detected (FIG. 2B), whereas no GFP expression was detected in mock-transfected cells (FIG. 2A). AdV/PolI-GFP transduction of Vero cells thus resulted in the synthesis of the reporter vRNA.

To provide the vRNP components entirely from AdVs, four additional helper-free AdVs were prepared for the expression of the polymerase subunits and NP (AdV/CMV-PB2, -PB1, -PA, and -NP) by cloning the cDNAs corresponding to the open reading frames of each WSN viral protein into pAd/CMV/V5-DEST (Invitrogen). Cotransduction of these AdVs into Vero cells with AdV/PolI-GFP (MOI=50) resulted in highly efficient GFP expression 48 hours post-transduction (FIG. 2C). These results show that AdV transduction achieves functional vRNP formation at a much higher efficiency than does plasmid transfection in Vero cells.

To determine the optimal ratio of AdVs for protein expression to vRNA synthesis, AdV/PolI-GFP was transduced into Vero cells at different MOIs together To determine the optimal ratio of AdVs for protein expression to vRNA synthesis, AdV/PolI-GFP was transduced into Vero cells at different MOIs together with AdV/CMV-PB2, -PB1, -PA, and -NP (MOI=50). The results showed that 5-fold fewer AdVs for vRNA synthesis than for viral protein expression are sufficient for efficient functional vRNP formation (data not shown).

Influenza virus generation entirely from AdVs. To generate infectious influenza virus entirely from AdVs, PolI transcription cassettes for all eight WSN vRNAs (Neumann et al., 1999) were cloned into pAd/PL-DEST and eight AdVs were made for the synthesis of each vRNA segment. Vero cells were cotransduced with a total of 12 AdVs, eight AdVs for the vRNA synthesis (MOI=10) and four AdVs for the viral protein expression (MOI=50). To compare the efficiency of virus generation, two methods of plasmid-based reverse genetics were performed: the 12-plasmid system (Neumann et al., 2002) and the 3-plasmid system (Neumann et al., 2005). At 72 hours after AdV transduction or plasmid transfection, culture supernatants were harvested and subjected to plaque assay on MDCK cells to determine the amounts of virus generated. Influenza virus was detected in the supernatant of cells transduced with 12 AdVs (FIG. 3), demonstrating the capacity of this AdV-mediated reverse genetics system for influenza virus generation. The virus yield from the 12-AdV transduced cells was approximately 1000-fold higher than that from the 12-plasmid transfected cells and comparable to that from the 3-plasmid transfected cells (FIG. 3).

Figure 1C:
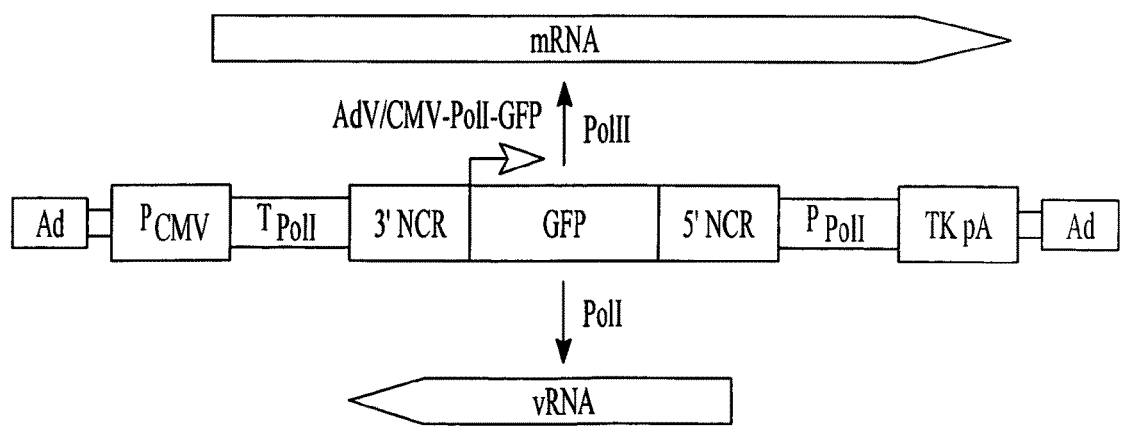

Influenza virus generation from eight AdVs based on the PolI-PolII bidirectional transcription system. To reduce the number of AdVs required for virus generation, the PolI-PolII bidirectional transcription approach, which allows the simultaneous synthesis of vRNA and mRNA from one template (Hoffmann et al., 2000), was tested for its applicability for the AdV-mediated reverse genetics system. By cloning the transcriptional region in pPolI-GFP into pAd/CMV/V5-DEST, AdV/CMV-PolI-GFP was generated (FIG. 1C). Vero cells transduced only with this AdV (MOI=50) expressed GFP at a relatively low level 48 hours post-transduction (FIG. 2D). Cotransduction with AdV/CMVTPB2, -PB1, -PA, and -NP enhanced the GFP expression level in individual cells (FIG. 2E). These results indicate that AdV/CMV-PolI-GFP transduction induces the synthesis of both the reporter vRNA and mRNA.

To generate infectious influenza virus from eight AdVs, PolI transcription cassettes for all eight WSN vRNAs were cloned into pAd/CMV/V5-DEST and eight AdVs containing the bidirectional transcription cassette were made for each vRNA segment. Vero cells were cotransduced with these AdVs (MOI=50). The virus yields were determined 72 hours post-transduction by plaque assay on MDCK cells. The amount of virus generated in Vero cells with the eight AdVs was approximately 10,000-, 10-, and 10-fold higher than that from the 12-plasmid (P=0.032), 3-plasmid (P=0.045), and 12-AdV (P=0.035) systems, respectively (FIG. 3).

Summary

Here, it is demonstrated that the limitation of transfection efficiency of target cells is overcome by using AdV as a gene transfer vehicle. Influenza vRNA was efficiently transcribed (FIGS. 2C and E) and influenza virus generated with high efficiency in Vero cells transduced with AdV possessing the PolI promoter and terminator (FIG. 3). Moreover, the 8 AdV transduction system, based on the PolI-PolII bidirectional transcription system (Hoffmann et al., 2000), achieved a statistically significant increase in virus yield compared to the other systems, including the recently established 3-plasmid transfection system (Neumann et al., 2005). Given the relative ease of preparation, the 8 AdV transduction system appears ideal for the efficient generation of influenza vaccine seed strains. This AdV-mediated reverse genetics system could also contribute to basic studies of influenza virus.

Example II

H5N1 influenza A viruses continue to cause fatal human infections. The epidemic regions have expanded from Asia to Europe and Africa, raising concerns over a possible pandemic (Horimoto et al., 2005). Currently, pre-pandemic H5N1 vaccines are being stockpiled in many countries. These inactivated vaccines were produced from viruses propagated in chicken embryonated eggs following inoculation of the vaccine seed virus, generated by cloned cDNA-based reverse genetics in a 12-plasmid (Foder et al., 1999; Neumann et al., 1999) or 8-plasmid (Hoffman et al., 2000) system, in an African green monkey Vero cell line (Horimoto et al., 2006; Nicolson et al., 2005; Subbarao et al., 2003; Webby et al., 2004; Wood et al., 2004) that is approved for human vaccine production (e.g., polio and rabies vaccines, see, Montagnon et al., 1999). However, the generation of the H5N1 vaccine seed viruses in this cell line is not optimal due to its low plasmid transfection efficiency. In a pandemic situation, vaccines whose antigenicities match the circulating strain(s) need to be rapidly produced. Therefore, a more robust reverse genetics system is desirable for pandemic vaccine preparedness.

Besides Vero cells, a limited number of other cells are approved for human vaccine production, for example, Madin-Darby canine kidney (MDCK) cells and chicken embryonic fibroblasts (CEF). A modified reverse genetics system that uses the chicken RNA polymerase I (PolI) promoter also supports the generation of influenza virus in CEF (Massin et al., 2005), with an efficiency of virus generation comparable to the human PolI system in Vero cells. MDCK cells also support the efficient growth of influenza virus and are used as a substrate for the production of seasonal influenza vaccines (Brands et al., 1999; Govorkova et al., 1999; Halperin et al., 2002). In MDCK cells, however, reverse genetics with the human PolI promoter does not work well, due to the host species specificity of the PolI promoter. Recently, another reverse genetics system with T7 RNA polymerase I was shown to support influenza virus generation in MDCK cells (de Wit et al., 2007); although, the efficiency of virus generation was inconsistent. In the present study, an alternative reverse genetics system was established that was driven by canine PolI and that generated recommended H5N1 vaccine seed viruses in MDCK cells with high efficiency.

Figures 6A, 6B:
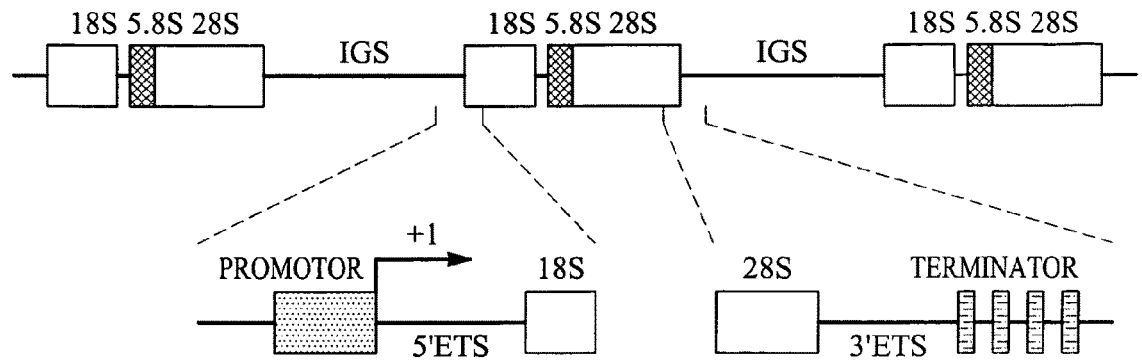

Eukaryotic ribosomal DNA consists of well-conserved 18, 5.8, and 28S rRNA genes, clustering head-to-tail repeats (FIG. 6A). The 18S and 28S rRNA genes are separated by intergenic spacer regions (IGS), which contain the PolI promoter and terminator sequences. The PolI promoter region is located next to a 5'-external transcribed spacer (5' ETS), approximately 3.5 kb upstream of the 18S rRNA gene in the human genome. Although the IGS sequences are not highly conserved among eukaryotes, the sequences around the transcription initiation sites are relatively conserved (Pauli et al., 2000) (FIG. 6B).

To identify the canine PolI promoter region, the canine chromosome that contains the 18, 5.8, and 28S rRNA genes was searched in the database of the dog genome (Lindblad-Toh et al., 2005) (NCBI Dog Genome Resources: see the URL at www.ncbi.nlm.nih.gov/genome/guide/dog/), and the predicted canine rRNA genes were found on a chromosome, designated *Canis familiaris* chromosome Un genomic contig, whole genome shotgun sequence (GenBank accession no. NW_878945: herein refer to as ChromUN). A homology search of the PolI transcription initiation site (nt −8 to +11; +1 is refer to as the transcription initiation site) approximately 3.5 kb upstream of the 18S rRNA gene (5' end of the predicted 5' ETS) in ChromUN with the human PolI transcription initiation site was performed by using the GENETYX-Win software (Genetyx Corp., Tokyo). Through these analyses, it was predicted that the PolI transcription initiation site sequence was positioned from 28164 to 28182 on ChromUN (FIG. 6B). The upstream regions (consisting of 457 or 250 nt) from the predicted transcription initiation site were amplified, which most likely contained the canine PolI promoter sequence, by a standard PCR using an MDCK cell DNA template and specific primer pairs designed according to the database information (FIG. 6C). The PCR products were then cloned into pCR-Blunt II-TOPO® (Invitrogen) and sequenced. The cloned sequence possessed 94.2% homology with the corresponding region of the ChromUN sequence (FIG. 6C).

To determine whether the cloned regions functioned as a canine PolI promoter in MDCK cells, the synthesis of viral RNA under the control of this region was examined. To this end, a plasmid was prepared that contained viral RNA downstream of the predicted canine PolI promoter region; the human PolI promoter sequence (nt −1 to −425) of pHH21 (Neumann et al., 1999) was replaced with the predicted canine PolI promoter sequences (nt −1 to −250 or nt −1 to −457; designated as pPolIC250 or pPolIC457 plasmids, respectively). For comparison, the chicken PolI promoter region was cloned from chicken genomic DNA (Massin et al., 2005), and pPolIGG was constructed, which synthesizes viral RNA. Finally, a series of reporter plasmids, in which the open reading frame of the firefly luciferase gene was inserted between the 3' and 5' non-coding regions of the NP segment of A/Purto Rico/8/34 (PR8) (NP(0)Fluc(0)) was prepared with pHH21, pPolIC250, pPolIC457, and pPolIGG, and designated as pPolI-NP(0)Fluc(0), pPolIC250-NP(0)Fluc(0), pPolIC457-NP(0)Fluc(0), and pPolIGG-NP(0)Fluc(0), respectively. As a negative control, a plasmid lacking the PolI promoter region (pΔPolIprom-NP(0)Fluc(0)) was also prepared.

For the luciferase reporter assay, each of the plasmids was cotransfected with PB2-, PB1-, PA-, and NP-expressing plasmids (Ozawa et al., 2007) into MDCK, Vero cells, or CEF. After 12 h of transfection, cells were harvested and lysed, and their luciferase activities measured and standardized against the activity of *Renilla* luciferase as an internal control by using a Dual-luciferase assay kit (Promega) (FIG. 7). MDCK cell lysates transfected with pPolIC250-NP(0)Fluc(0) or pPolIC457-NP(0)Fluc(0) exhibited more than 10-fold higher luciferase activity, compared to those with pPolI-NP(0)Fluc (0) or pPolI GG-NP(0)Fluc(0) ($p<0.02$: student t-test). By contrast, the lysates of Vero and CEF cells transfected with pPolIC250-NP(0)Fluc(0) or pPolIC457-NP(0)Fluc(0) exhibited significantly lower luciferase activity, compared to those with pPolI-NP(0)Fluc(0) ($p<0.02$) and pPolIGG-NP(0)Fluc (0) ($p<0.002$), respectively. None of the cell lysates transfected with the control pAPolIprom-NP(0)Fluc(0) showed any detectable luciferase activity. These data demonstrated that the region we cloned contained the functional canine PolI promoter.

To authenticate the canine PolI promoter, the generation of the wild-type PR8 virus in MDCK cells was attempted using reverse genetics. The eight viral genes of the PR8 (UW) strain (Horimoto et al., 2007) were cloned into the pPolIC250 or pPolIC457 plasmids (pPolIC250-PB2, -PB1, -PA, -HA, -NP, -NA, -M, -NS, or pPolIC457-PB2, -PB1, -PA, -HA, -NP, -NA, -M, -NS, respectively). Then MDCK cells were transfected with a set of 8 segments of pPolIC250 or pPolIC457 together with plasmids expressing PB2, PB1, PA, and NP, resulting in the generation the virus with titers between $1.3 \times 10^2$ and $2.5 \times 10^3$ PFU/ml without exogenous trypsin (Table 1).

TABLE 1

Efficiency of PR8 generation in MDCK cells

| Experiment No. | Infectivity titer (PFU/ml)[a] | | | |
|---|---|---|---|---|
| | pPolIC250(PR8)[b] | | pPolIC457(PR8)[c] | |
| | Trypsin (−)[d] | Trypsin(+)[e] | Trypsin(−)[d] | Trypsin(+)[e] |
| 1 | $2.5 \times 10^2$ | $1.9 \times 10^4$ | $1.3 \times 10^2$ | $3.0 \times 10^4$ |
| 2 | $2.5 \times 10^3$ | $7.8 \times 10^4$ | $1.4 \times 10^2$ | $5.0 \times 10^3$ |
| 3 | $4.6 \times 10^2$ | $1.3 \times 10^4$ | $1.5 \times 10^3$ | $1.4 \times 10^4$ |

[a]At 48 hours after transfection, virus titers in the supernatant were determined by plaque assays in MDCK cells.
[b]pPolIC250(PR8) is a combination of pPolIC250-PB2, -PB1, -PA, -HA, -NP, -NA, -M, and -NS
[c]pPolIC457(PR8) is a combination of pPolIC457-PB2, -PB1, -PA, -HA, -NP, -NA, -M, and -NS
[d]Cells were cultured with trypsin-free OPTI-MEM.
[e]Cells were cultured with OPTI-MEM containing trypsin.
Results are of three independent experiments.

When MDCK cells were transfected with these sets of plasmids in the presence of trypsin, virus titers of more than $5 \times 10^3$ PFU/mL were detected. No significant differences in virus yields were observed between sets of pPolIC250 and pPolIC457 plasmids. By contrast, no viruses were detected on transfection of MDCK cells with a series of pPolI (human promoter) or pPolIGG (chicken promoter) plasmids (data not shown), in agreement with the results of the luciferase assay (FIG. 7). The generation of virus in MDCK cells with the plasmids possessing the canine PolI promoter was robust, with consistent virus generation of more than $10^2$ PFU/mL without exogenous trypsin in all experiments (n=6). However, occasionally, virus was not generated with plasmids possessing the chicken PolI promoter in CEF. Massin et al. (2005) reported the generation of PR8 virus by reverse genetics with the chicken PolI promoter in the presence of trypsin, resulting in virus production of $10^2$ to $10^3$ PFU/mL on day 3 after transfection in CEF. Less efficient virus generation by reverse genetics with the human PolI promoter in Vero cells has also been reported; Fodor et al. (1999) generated A/WSN/33 (WSN) virus with titers of 10-20 PFU/mL on day 4 after transfection by using the 12-plasmid system. Because MDCK cells are a suitable substrate for influenza virus replication (Govorkova et al., 1999), the canine PolI-driven reverse genetics system in MDCK cells likely supports higher efficiency of virus generation than do the human PolI or chicken PolI-driven systems in Vero cells and CEF.

Next, an H5N1 vaccine seed virus was generated, as recommended by the World Health Organization (PR8/H5N1 6:2 reassortant; virus possessing HA and NA genes from an H5N1 virus and the remaining genes from PR8 (UW) strain, Horimoto et al., 2002) using the canine PolI-driven system. For this purpose, HA (with a modified cleavage site; RERRRKKR (SEQ ID NO:9) to RETR (SEQ ID NO:10)) and NA genes, both derived from A/Vietnam/1194/2004 (H5N1; VN1194) (Horimoto et al., 2006) were cloned into pPolIC250 plasmids (pPolIC250-1194HA, and -1194NA, respectively). These two plasmids were then cotransfected with six PR8 RNA-synthesizing plasmids and four additional plasmids expressing PB2, PB1, PA, and NP into MDCK cells, resulting in the generation of virus with titers of approximately $10^2$ PFU/mL in the absence of trypsin and of more than $10^6$ PFU/ml in the presence of trypsin (Table 2).

TABLE 2

Efficiency of PR8/VN1194 6:2 reassortant virus generation in MDCK cells

| Experiment No. | Infectivity Titer[a] pPolIC250(PR8/VN1194)[b] Trypsin(−)[c] | Trypsin(+)[d] |
|---|---|---|
| 1 | $1.3 \times 10^2$ | $3.2 \times 10^6$ |
| 2 | $1.1 \times 10^2$ | $1.2 \times 10^6$ |
| 3 | $1.3 \times 10^2$ | $3.6 \times 10^6$ |

[a]At 48 hours after transfection, virus titers in the supernatant were determined by plaque assays in MDCK cells.
[b]pPolIC250(PR8/VN1194) is a combination of pPolIC250-PB2, -PB1, -PA, -NP, -M, -NS, -1194HA, and -1194NA
[c]Cells were cultured with trypsin-free OPTI-MEM.
[d]Cells were cultured with OPTI-MEM containing trypsin.
Results are of three independent experiments.

By contrast, in Vero cells and in CEF, this PR8/H5N1 reassortant was also generated by transfection with the human PolI or the chicken PolI system, respectively, but to a substantially lesser degree; the virus generation was not consistent and even when virus was generated, the titers were less than 10 PFU/mL in either system. Taken together, PR8/H5N1 vaccine seed viruses can be generated more efficiently by canine PolI-driven reverse genetics in MDCK cells than by human or chicken PolI-driven systems in Vero cells or CEF.

The recently described T7 RNA polymerase I-driven reverse genetics system (de Wit et al., 2007) allows the generation of influenza viruses in MDCK cells although its robustness is not clear, as the results in the original publication depict large error bars. However, it is unlikely that this system will generate vaccine seed viruses efficiently in Vero or MDCK cells, since even in 293T cells with high transfection efficiency, PR8 virus was poorly generated (less than 10 50% tissue culture infectious dose ($TCID_{50}$)/mL). Currently, PolI-based reverse genetics is used to produce H5N1 vaccine seed viruses (Horimoto et al., 2006; Nicolson et al., 2005; Subbarao et al., 2003; Webby et al., 2004; Wood et al., 2004). Since the present results indicate that the canine PolI-based system is more efficient than the human or chicken PolI-based systems, the canine system may be preferable.

Previously, a reverse genetics system was established with a reduced number of plasmids to overcome the low transfection efficiency of certain cells that are approved for vaccine production (e.g., Vero cells). This system generated A/WSN/33 (H1N1) virus in Vero cells with high viral yields ($10^6$ to $10^7$ ($TCID_{50}$)/ml (Neumann et al., 2005). Therefore, a similar strategy could be applied to the canine PolI-driven system, possibly further improving its efficiency in MDCK cells. In addition, an adenoviral vector-mediated reverse genetics system (Example I) with the canine PolI promoter may also be suitable for influenza vaccine production.

In conclusion, application of the canine PolI-driven reverse genetic system in MDCK cells would improve production of seasonal, pre-pandemic, and pandemic influenza vaccines.

REFERENCES

Albo et al., *J. Virol.,* 70:9013 (1996).
*Avery's Drug Treatment: Principles and Practice of Clinical Pharmacology and Therapeutics,* 3rd edition, ADIS Press, Ltd., Williams and Wilkins, Baltimore, Md. (1987).
Aymard-Henry et al., *Virology: A Practical Approach,* Oxford IRL Press, Oxford, 119-150 (1985).
Bachmeyer, *Intervirology,* 5:260 (1975).
Berkow et al., eds., *The Merck Manual,* 16th edition, Merck & Co., Rahway, N.J. (1992).
Brands et al., *Dev. Biol. Stand.,* 98:93 (1999).
Bridgen et al., *Proc. Natl. Acad. Sci. U.S.A,* 93:15400 (1996).
Bruhl et al., *Vaccine,* 19:1149 (2000).
Claas et al., *Lancet,* 351:472 (1998).
de Wit et al., *J. Gen. Virol.,* 88:1281 (2007).
Dunn et al., *Virology,* 211:133 (1995).
Edwards, *J. Infect. Dis.,* 169: 68 (1994).
Elliott, *Mol. Med.,* 3:572 (1997).
Fodor et al., J. Virol., 73:9679 (1999)
Fouchier et al., *Proc. Natl. Acad. Sci. USA,* 101:1356 (2004).
Gerdil, *Vaccine,* 21:1776 (2003).
Goto et al., *Virology,* 238:265 (1997).
Govorkova et al., *Dev. Biol. Stand.,* 98:39 (1999).
Grand and Skehel, *Nature, New Biology,* 238:145 (1972).
Hagen et al., *J. Virol.,* 68:1509 (1994).
Halperin et al., *Vaccine,* 20:1240 (2002).
Hoffman et al., *Proc. Natl. Acad. Sci. USA,* 97:6108 (2000).
Hoffman et al., *Proc. Natl. Acad. Sci. USA,* 99:11411 (2002).
Hoffmann et al., *Virology,* 267:310 (2000).
Horimoto et al., *Nat. Rev. Microbiol.,* 3:591 (2005).
Horimoto et al., *Vaccine,* 24:3669 (2006).
Horimoto et al., *Virology,* 366:23 (2007).
Kilbourne, *Bull. M2 World Health Org.,* 41: 653 (1969).
Kistner et al., *Dev. Biol. Stand.,* 98:101 (1999).
Kistner et al., *Vaccine,* 16:960 (1998).
Kistner et al., *Wien Klin. Wochenschr.,* 111:207 (1999).
Koopsman et al., *Lancet,* 363:587 (2004).
Laver & Webster, *Virology,* 69:511 (1976).
Leahy et al., *J. Virol.* 71:8347 (1997).
Leahy et al., *J. Virol.,* 71:8352 (1997).
Leahy et al., *J. Virol.,* 72:2305 (1998).
Lindblad-Toh et al., *Nature* 438:803 (2005).
Massin et al., *J. Virol.,* 79:13811 (2005).
Mizrahi, (ed.), *Viral Vaccines*, Wiley-Liss, New York, 39-67 (1990).
Montagnon et al., *Dev. Biol. Stand,* 98:137 (1999).

Murphy, *Infect. Dis. Clin. Pract.*, 2: 174 (1993).
Neumann et al., *Adv. Virus Res.*, 53:265 (1999).
Neumann et al., *Curr. Top. Microbiol. Immunol.*, 283:43 (2004).
Neumann et al., *J. Gen. Virol.*, 83:2635 (2002).
Neumann et al., *J. Virol.*, 74:547 (2000).
Neumann et al., *J. Virol.*, 76:406 (2002).
Neumann et al., *Proc. Natl. Acad. Sci. USA*, 102:16825 (2005).
Neumann et al., *Proc. Natl. Acad. Sci. USA*, 96:9345 (1999).
Neumann et al., *Rev. Med. Virol.*, 12:13 (2002).
Nicolson et al., *Vaccine*, 23:2943 (2005).
Ogra et al., *J. Infect. Dis.*, 134: 499 (1977).
Osol (ed.), *Remington's Pharmaceutical Sciences*, Mack Publishing Co., Easton, Pa. 1324-1341 (1980).
Ozaki et al., *J. Virol.*, 78:1851 (2004).
Ozawa et al., *J. Virol.*, 81:30 (2007).
Palache et al., *Dev. Biol. Stand.*, 98:115 (1999).
Paule et al., *Nucleic Acids Res.*, 28:1283 (2000).
Peiris et al., *Lancet*, 363:617 (2004).
Potter in *Textbook of Influenza*, eds. Nicholson, K. G., Webster, R. G. & Hey, A. J.; Maiden: Blackwell Scientific Publication, pp. 3-18 (1998).
Robertson et al., *Biologicals*, 20:213 (1992).
Robertson et al., *Giornale di Igiene e Medicina Preventiva*, 29:4 (1988).
Schnell et al., *EMBO J.*, 13:4195 (1994).
Subbarao et al., *J. Virol.*, 67:7223 (1993).
Subbarao et al., *Science*, 279:393 (1998).
Subbarao et al., *Virology*, 305:192 (2003).
Takada et al., *J. Virol.*, 73:8303 (1999).
Thompson et al., *Jama*, 289:179 (2003).
Webby et al., *Lancet*, 363:1099 (2004).
Weber et al., *Arch. Virol*, 142:1029 (1997).
Weber et al., *J. Virol.*, 70:8361 (1996).
WHO, Cumulative Number of Confirmed Human Cases of Avian Influenza A (H5N1) since 28 Jan. 2004.
Wood et al., *Nat. Rev. Microbiol.*, 2:842 (2004).
World Health Organization TSR No. 673 (1982).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. An isolated host cell infected with a plurality of helper-free recombinant adenovirus vectors effective for infectious influenza virus production, wherein the adenovirus vectors include adenovirus vectors for influenza virus vRNA production and adenovirus vectors for influenza virus mRNA production, wherein (a) the vectors for influenza vRNA production comprise an adenovirus vector comprising a PolI promoter operably linked to an influenza virus PA DNA linked to a PolI transcription termination sequence, an adenovirus vector comprising a PolI promoter operably linked to an influenza virus PB1 DNA linked to a PolI transcription termination sequence, an adenovirus vector comprising a PolI promoter operably linked to an influenza virus PB2 DNA linked to a PolI transcription termination sequence, an adenovirus vector comprising a PolI promoter operably linked to an influenza virus HA DNA linked to a PolI transcription termination sequence, an adenovirus vector comprising a PolI promoter operably linked to an influenza virus NP DNA linked to a PolI transcription termination sequence, an adenovirus vector comprising a PolI promoter operably linked to an influenza virus NA DNA linked to a PolI transcription termination sequence, an adenovirus vector comprising a PolI promoter operably linked to an influenza virus M DNA linked to a PolI transcription termination sequence, and an adenovirus vector comprising a PolI promoter operably linked to an influenza virus NS DNA linked to a PolI transcription termination sequence; and wherein the adenovirus vectors for mRNA production comprise an adenovirus vector comprising a PolII promoter operably linked to a DNA segment encoding influenza virus PA, an adenovirus vector comprising a PolII promoter operably linked to a DNA segment encoding influenza virus PB1, an adenovirus vector comprising a PolII promoter operably linked to a DNA segment encoding influenza virus PB2, and an adenovirus vector comprising a PolII promoter operably linked to a DNA segment encoding influenza virus NP;

(b) the vectors for influenza vRNA production comprise an adenovirus vector comprising a PolI promoter operably linked to an influenza virus PA DNA linked to a PolI transcription termination sequence, an adenovirus vector comprising a PolI promoter operably linked to an influenza virus PB1 DNA linked to a PolI transcription termination sequence, an adenovirus vector comprising a PolI promoter operably linked to an influenza virus PB2 DNA linked to a PolI transcription termination sequence, an adenovirus vector comprising a PolI promoter operably linked to an influenza virus HA DNA linked to a PolI transcription termination sequence, an adenovirus vector comprising a PolI promoter operably linked to an influenza virus NP DNA linked to a PolI transcription termination sequence, an adenovirus vector comprising a PolI promoter operably linked to an influenza virus NA and NB DNA linked to a PolI transcription termination sequence, an adenovirus vector comprising a PolI promoter operably linked to an influenza virus M DNA linked to a PolI transcription termination sequence, and an adenovirus vector comprising a PolI promoter operably linked to an influenza virus NS DNA linked to a PolI transcription termination sequence; and wherein the vectors for mRNA production comprise an adenovirus vector comprising a PolII promoter operably linked to a DNA segment encoding influenza virus PA, an adenovirus vector comprising a PolII promoter operably linked to a DNA segment encoding influenza virus PB1, an adenovirus vector comprising a PolII promoter operably linked to a DNA segment encoding influenza virus PB2, and an adenovirus vector comprising a PolII promoter operably linked to a DNA segment encoding influenza virus NP; or (c) the vectors for influenza vRNA production comprise an adenovirus vector comprising a PolI promoter operably linked to an influenza virus PA DNA linked to a PolI transcription termination sequence, an adenovirus vector comprising a PolI promoter operably linked to an influenza virus PB1 DNA linked to a PolI transcription termination sequence, an adenovirus vector comprising a PolI promoter operably linked to an influenza virus PB2 DNA linked to a PolI transcription termination sequence, an adenovirus vector comprising a PolI promoter operably linked to an influenza virus HA DNA linked to a PolI transcription termination sequence, an adenovirus vector comprising a PolI promoter operably linked to an influenza virus NP DNA linked to a PolI transcription termination sequence, an adenovirus vector comprising a PolI promoter operably linked to an influenza virus M DNA linked to a PolI transcription termination sequence, and an adenovirus vector comprising a PolI promoter operably linked to an influenza virus NS DNA linked to a PolI transcription termination sequence; wherein the adenovirus vectors for mRNA production comprise an adenovirus vector comprising a PolII promoter operably linked to a DNA segment encoding influenza virus PA, an adenovirus vector comprising a PolII promoter operably linked to a DNA segment encoding influenza virus PB1, an adenovirus vector comprising a PolII promoter operably linked to a DNA segment encoding influenza virus PB2, and an adenovirus vector comprising a PolII promoter operably linked to a DNA segment encoding influenza virus NP; wherein the host cell with the vectors in (c) does not include sequences corresponding to influenza virus NA coding or noncoding sequences for vRNA production or for vRNA production and mRNA NA production.

2. An isolated host cell infected with a plurality of helper-free adenovirus vectors effective for influenza virus production, wherein (a) the adenovirus vectors comprise an adenovirus vector comprising a PolII promoter linked to a PolI transcription termination sequence linked to an influenza virus PA DNA linked to a PolI promoter linked to a PolII transcription termination sequence, an adenovirus vector comprising a PolII promoter linked to a PolI transcription termination sequence linked to an influenza virus PB1 DNA linked to a PolI promoter linked to a PolII transcription termination sequence, an adenovirus vector comprising a PolII promoter linked to a PolI transcription termination sequence linked to an influenza virus PB2 DNA linked to a PolI promoter linked to a PolII transcription termination sequence, an adenovirus vector comprising a PolII promoter linked to a PolI transcription termination sequence linked to an influenza virus HA DNA linked to a PolI promoter linked to a PolII transcription termination sequence, an adenovirus vector comprising a PolII promoter linked to a PolI transcription termination sequence linked to an influenza virus NP DNA linked to a PolI promoter linked to a PolII transcription termination sequence, an adenovirus vector comprising a PolII promoter linked to a PolI transcription termination sequence linked to an influenza virus NA DNA linked to a PolI promoter linked to a PolII transcription termination sequence, an adenovirus vector comprising a PolII promoter linked to a PolI transcription termination sequence linked to an influenza virus M DNA linked to a PolI promoter linked to PolII transcription termination sequence, and an adenovirus vector comprising a PolII promoter linked to a PolI transcription termination sequence linked to an influenza virus NS DNA linked to a PolI promoter linked to PolII transcription termination sequence; or (b) the adenovirus vectors comprise an adenovirus vector comprising a PolII promoter linked to a PolI transcription termination sequence linked to an influenza virus PA DNA linked to a PolI promoter linked to a PolII transcription termination sequence, an adenovirus vector comprising a PolII promoter linked to a PolI transcription termination sequence linked to an influenza virus PB1 DNA linked to a PolI promoter linked to a PolII transcription termination sequence, an adenovirus vector comprising a PolII promoter linked to a PolI transcription termination sequence linked to an influenza virus PB2 DNA linked to a PolI promoter linked to a PolII transcription termination sequence, an adenovirus vector comprising a PolII promoter linked to a PolI transcription termination sequence linked to an influenza virus HA DNA linked to a PolI promoter linked to a PolII transcription termination sequence, an adenovirus vector comprising a PolII promoter linked to a PolI transcription termination sequence linked to an influenza virus NP DNA linked to a PolI promoter linked to a PolII transcription termination sequence, an adenovirus vector comprising a PolII promoter linked to a PolI transcription termination sequence linked to an influenza virus NA and NB DNA linked to a PolI promoter linked to a PolII transcription termination sequence, an adenovirus vector comprising a PolII promoter linked to a PolI transcription termination sequence linked to an influenza virus M DNA linked to a PolI promoter linked to PolII transcription termination sequence, and an adenovirus vector comprising a PolII promoter linked to a PolI transcription termination sequence linked to an influenza virus NS DNA linked to a PolI promoter linked to PolII transcription termination sequence.

3. The host cell of claim 1 further comprising an adenovirus vector for influenza virus vRNA production comprising a PolI promoter operably linked to 5' non-coding influenza virus sequences linked to a heterologous DNA of interest in antigenomic orientation linked to 3' non-coding influenza virus sequences linked to a PolI transcription termination sequence.

4. The host cell of claim 2 further comprising an adenovirus vector for influenza virus vRNA and mRNA production comprising a PolII promoter linked to a PolI transcription termination sequence linked to 5' non-coding influenza virus sequences linked to a heterologous DNA of interest linked to 3' non-coding influenza virus sequences linked to a PolI promoter linked to a PolII transcription termination sequence.

5. The host cell of claim 1 or 2 wherein the PolI promoter is a human or a canine PolI promoter.

6. The host cell of claim 1 or 2 which is a Vero cell.

7. The host cell of claim 1 or 2 which is a MDCK cell.

8. The host cell of claim 1 or 2 wherein the host cell is sequentially infected with the adenovirus vectors.

9. The host cell of claim 1 or 2 wherein the M DNA has sequences for a mutant M2 which lacks or has reduced activity relative to the corresponding wild-type M2 protein, wherein the mutation is in the transmembrane domain in the M2 protein.

10. The host cell of claim 1 or 2 wherein the NA and NB DNA has sequences for a functional NA protein and a mutant NB gene.

11. The host cell of claim 10 wherein the sequences for the mutant NB gene comprise at least two mutations relative to a corresponding NB gene which encodes a functional NB protein, one of which mutations is not in a region of the NB gene corresponding to the transmembrane domain.

12. The host cell of claim 1 or 2 which produces a reassortant influenza virus.

13. The host cell of claim 12 wherein the reassortant is a 6:2 reassortant.

14. The host cell of claim 12 wherein the reassortant is a 7:1 reassortant.

15. A method to prepare influenza virus, comprising: infecting an isolated host cell with a plurality of helper-free adenovirus vectors for influenza virus vRNA production and for influenza virus mRNA production, wherein (a) the vectors for influenza vRNA production comprise an adenovirus vector comprising a PolI promoter operably linked to an influenza virus PA DNA linked to a PolI transcription termination sequence, an adenovirus vector comprising a PolI promoter operably linked to an influenza virus PB1 DNA linked to a PolI transcription termination sequence, an adenovirus vector comprising a PolI promoter operably linked to an influenza virus PB2 DNA linked to a PolI transcription termination sequence, an adenovirus vector comprising a PolI promoter operably linked to an influenza virus HA DNA linked to a PolI transcription termination sequence, an adenovirus vector comprising a PolI promoter operably linked to an influenza virus NP DNA linked to a PolI transcription termination sequence, an adenovirus vector comprising a PolI promoter operably linked to an influenza virus NA DNA linked to a PolI transcription termination sequence, an adenovirus vector comprising a PolI promoter operably linked to an influenza virus M DNA linked to a PolI transcription termination sequence, and an adenovirus vector comprising a PolI promoter operably linked to an influenza virus NS DNA linked to a PolI transcription termination sequence, an adenovirus vector comprising a PolII promoter operably linked to a DNA segment encoding influenza virus PA, an adenovirus vector comprising a PolII promoter operably linked to a DNA segment encoding influenza virus PB1, an adenovirus vector comprising a PolII promoter operably linked to a DNA segment encoding influenza virus PB2, and an adenovirus vector comprising a PolII promoter operably linked to a DNA segment encoding influenza virus NP;

(b) the vectors for influenza vRNA production comprise an adenovirus vector comprising a PolI promoter operably linked to an influenza virus PA DNA linked to a PolI transcription termination sequence, an adenovirus vector comprising a PolI promoter operably linked to an influenza virus PB1 DNA linked to a PolI transcription termination sequence, an adenovirus vector comprising a PolI promoter operably linked to an influenza virus PB2 DNA linked to a PolI transcription termination sequence, an adenovirus vector comprising a PolI promoter operably linked to an influenza virus HA DNA linked to a PolI transcription termination sequence, an adenovirus vector comprising a PolI promoter operably linked to an influenza virus NP DNA linked to a PolI transcription termination sequence, an adenovirus vector comprising a PolI promoter operably linked to an influenza virus NA and NB DNA linked to a PolI transcription termination sequence, an adenovirus vector comprising a PolI promoter operably linked to an influenza virus M DNA linked to a PolI transcription termination sequence, and an adenovirus vector comprising a PolI promoter operably linked to an influenza virus NS DNA linked to a PolI transcription termination sequence, an adenovirus vector comprising a PolII promoter operably linked to a DNA segment encoding influenza virus PA, an adenovirus vector comprising a PolII promoter operably linked to a DNA segment encoding influenza virus PB1, an adenovirus vector comprising a PolII promoter operably linked to a DNA segment encoding influenza virus PB2, and an adenovirus vector comprising a PolII promoter operably linked to a DNA segment encoding influenza virus NP; or (c) the vectors for influenza vRNA production comprise an adenovirus vector comprising a PolI promoter operably linked to an influenza virus PA DNA linked to a PolI transcription termination sequence, an adenovirus vector comprising a PolI promoter operably linked to an influenza virus PB1 DNA linked to a PolI transcription termination sequence, an adenovirus vector comprising a PolI promoter operably linked to an influenza virus PB2 DNA linked to a PolI transcription termination sequence, an adenovirus vector comprising a PolI promoter operably linked to an influenza virus HA DNA linked to a PolI transcription termination sequence, an adenovirus vector comprising a PolI promoter operably linked to an influenza virus NP DNA linked to a PolI transcription termination sequence, an adenovirus vector comprising a PolI promoter operably linked to an influenza virus M DNA linked to a PolI transcription termination sequence, and an adenovirus vector comprising a PolI promoter operably linked to an influenza virus NS DNA linked to a PolI transcription termination sequence; wherein the adenovirus vectors for mRNA production comprise an adenovirus vector comprising a PolII promoter operably linked to a DNA segment encoding influenza virus PA, an adenovirus vector comprising a PolII promoter operably linked to a DNA segment encoding influenza virus PB1, an adenovirus vector comprising a PolII promoter operably linked to a DNA segment encoding influenza virus PB2, and an adenovirus vector comprising a PolII promoter operably linked to a DNA segment encoding influenza virus NP; wherein the host cell with the vectors in (c) does not include sequences corresponding to influenza virus NA coding or noncoding sequences for vRNA production or for vRNA production and mRNA NA production.

16. A method to prepare influenza virus, comprising: infecting an isolated host cell with a plurality of adenovirus vectors comprising a PolII promoter linked to a PolI transcription termination sequence linked to an influenza virus PA DNA linked to a PolI promoter linked to a PolII transcription termination sequence, an adenovirus vector comprising a PolII promoter linked to a PolI transcription termination sequence linked to an influenza virus PB1 DNA linked to a PolI promoter linked to a PolII transcription termination sequence, an adenovirus vector comprising a PolII promoter linked to a PolI transcription termination sequence linked to an influenza virus PB2 DNA linked to a PolI promoter linked to a PolII transcription termination sequence, an adenovirus vector comprising a PolII promoter linked to a PolI transcription termination sequence linked to an influenza virus HA DNA linked to a PolI promoter linked to a PolII transcription termination sequence, an adenovirus vector comprising a PolII promoter linked to a PolI transcription termination sequence linked to an influenza virus NP DNA linked to a PolI promoter linked to a PolII transcription termination sequence, an adenovirus vector comprising a PolII promoter linked to a PolI transcription termination sequence linked to an influenza virus NA DNA linked to a PolI promoter linked to a PolII transcription termination sequence, an adenovirus vector comprising a PolII promoter linked to a PolI transcription termination sequence linked to an influenza virus M DNA linked to a PolI promoter linked to PolII transcription termination sequence, and an adenovirus vector comprising a PolII promoter linked to a PolI transcription termination sequence linked to an influenza virus NS DNA linked to a PolI promoter linked to PolII transcription termination sequence in an amount effective to yield infectious influenza virus; or a plurality of adenovirus vectors comprising an adenovirus vector comprising a PolII promoter linked to a PolI transcription termination sequence linked to an influenza virus PA DNA linked to a PolI promoter linked to a PolII transcription termination sequence, an adenovirus vector comprising a PolII promoter linked to a PolI transcription termination sequence linked to an influenza virus PB1 DNA linked to a PolI promoter linked to a PolII transcription termination sequence, an adenovirus vector comprising a PolII promoter linked to a PolI transcription termination sequence linked to an influenza virus PB2 DNA linked to a PolI promoter linked to a PolII transcription termination sequence, an adenovirus vector comprising a PolII promoter linked to a PolI transcription termination sequence linked to an influenza virus HA DNA linked to a PolI promoter linked to a PolII transcription termination sequence, an adenovirus vector comprising a PolII promoter linked to a PolI transcription termination sequence linked to an influenza virus NP DNA linked to a PolI promoter linked to a PolII transcription termination sequence, an adenovirus vector comprising a PolII promoter linked to a PolI transcription termination sequence linked to an influenza virus NA and NB DNA linked to a PolI promoter linked to a PolII transcription termination sequence, an adenovirus vector comprising a PolII promoter linked to a PolI transcription termination sequence linked to an influenza virus M DNA linked to a PolI promoter linked to PolII transcription termination sequence and an adenovirus vector comprising a PolII promoter linked to a PolI transcription termination sequence linked to an influenza virus NS DNA linked to a PolI promoter linked to PolII transcription termination sequence.

17. The method of claim 15 or 16 further comprising isolating the influenza virus.

18. The method of claim 15 or 16 wherein the host cell is a Vero cell.

19. The method of claim 15 or 16 wherein the host cell is a MDCK cell.

20. The method of claim 15 or 16 wherein the PolI promoter is a human or canine PolI promoter.

21. A method to prepare an influenza virus, comprising: culturing the host cell of claim 3 or 4 in an amount effective to yield influenza virus, and isolating the virus.

22. The host cell of claim 1 or 2 wherein the HA is an influenza A virus HA.

23. The host cell of claim 22 wherein the HA is a H5 HA.

24. The host cell of claim 1 or 2 wherein the HA is an influenza B virus HA.

25. The method of claim 15 or 16 wherein the HA is an influenza A virus HA.

26. The method of claim 25 wherein the HA is a H5 HA.

27. The method of claim 15 or 16 wherein the HA is an influenza B virus HA.

28. The method of claim 15 wherein the M DNA has sequences for a mutant M2 which lacks or has reduced activity relative to the corresponding wild-type M2 protein, wherein the mutation is in the transmembrane domain in the M2 protein.

29. The method of claim 16 wherein the NA and NB DNA has sequences for a functional NA but not for a functional NB.

* * * * *